US009920106B2

(12) United States Patent
Johansen et al.

(10) Patent No.: US 9,920,106 B2
(45) Date of Patent: Mar. 20, 2018

(54) GLP-1 COMPOUNDS

(75) Inventors: Nils Langeland Johansen, Koebenhavn O (DK); Jesper Lau, Farum (DK); Kjeld Madsen, Vaerloese (DK); Thomas Kruse Hansen, Herlev (DK); Jeppe Sturis, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 1395 days.

(21) Appl. No.: 13/473,154

(22) Filed: May 16, 2012

(65) Prior Publication Data

US 2012/0289453 A1 Nov. 15, 2012

Related U.S. Application Data

(63) Continuation of application No. 11/454,804, filed on Jun. 16, 2006, now abandoned, which is a continuation of application No. PCT/DK2004/000886, filed on Dec. 17, 2004.

(60) Provisional application No. 60/587,181, filed on Jul. 12, 2004, provisional application No. 60/531,053, filed on Dec. 19, 2003.

(30) Foreign Application Priority Data

Dec. 18, 2003 (DK) .................. 2003 01885
Jul. 9, 2004 (DK) .................. 2004 01090

(51) Int. Cl.
*A61K 38/00* (2006.01)
*A61P 9/10* (2006.01)
*C07K 14/47* (2006.01)
*C07K 14/575* (2006.01)
*C07K 14/605* (2006.01)

(52) U.S. Cl.
CPC ...... *C07K 14/57563* (2013.01); *C07K 14/605* (2013.01); *A61K 38/00* (2013.01)

(58) Field of Classification Search
CPC . A61K 38/00; C07K 14/57563; C07K 14/605
See application file for complete search history.

(56) References Cited

U.S. PATENT DOCUMENTS

| 3,862,167 | A | 1/1975 | Ueno et al. | |
|---|---|---|---|---|
| 5,545,618 | A | 8/1996 | Buckley et al. | |
| 6,506,730 | B1 | 1/2003 | Lee et al. | |
| 6,864,069 | B2 * | 3/2005 | Pan | C07K 14/605 435/320.1 |
| 6,903,186 | B1 | 6/2005 | Dong | |
| 6,924,264 | B1 * | 8/2005 | Prickett | A61K 47/60 514/11.7 |
| 2003/0195154 | A1 | 10/2003 | Walker et al. | |
| 2005/0208587 | A1 * | 9/2005 | Cardoso | C07K 14/005 435/7.1 |
| 2008/0113905 | A1 | 5/2008 | DiMarchi et al. | |

FOREIGN PATENT DOCUMENTS

| BR | PI0613926 A2 | 2/2011 |
|---|---|---|
| BR | PI0907182 A2 | 2/2012 |
| DK | 2003/01885 | 12/2003 |
| DK | 2004/01090 | 7/2004 |
| EP | 2275439 A2 | 1/2011 |
| WO | 91/11457 A1 | 8/1991 |
| WO | 96/21469 | 7/1996 |
| WO | 97/03106 A1 | 1/1997 |
| WO | 98/08871 | 3/1998 |
| WO | 99/43706 | 9/1999 |
| WO | 00/12116 A1 | 3/2000 |
| WO | 00/16797 A2 | 3/2000 |
| WO | 00/34331 | 6/2000 |
| WO | 00/66629 | 11/2000 |
| WO | 01/04156 | 1/2001 |
| WO | 01/04156 A1 | 1/2001 |
| WO | 0151071 | 7/2001 |
| WO | 02098446 A1 | 12/2002 |
| WO | 03/040309 A2 | 5/2003 |
| WO | 2004/022004 | 3/2004 |
| WO | 2004/093823 A2 | 11/2004 |
| WO | 2005/058954 A1 | 6/2005 |

OTHER PUBLICATIONS

U.S. Appl. No. 60/408,696.
U.S. Appl. No. 60/439,369.
Knudsen L B et al. Potent Derivatives of Glucagon-like Peptide-1 with Pharmacokinetic Properties Suitable for Once Daily Administration, "J. Med. Chem." Year 2000, vol. 43, pp. 1664-1669.
United Kingdom House of Lords Decisions,Judgments—*Conor Medsystems Incorporated* (Respondents) v *Angiotech Pharmaceuticals Incorporated and others* (Appellants) Year 2008, pp. 1-16.
Deacon, C.F. et al, Diabetologia, "Dipeptidyl Peptidase . . . ", 1998, vol. 41, No. -, pp. 271-278.
Greenwald, Journal of the Controlled Release, "-", 2001, vol. 74, No. -, pp. 159-171.
Hinds, K D et al, Advanced Drug Delivery Reviews, "Effects of PEG Conjugation on Insulin Properties", 2002, vol. 54, pp. 505-530.
Meester et al., -, "Cellular Peptidases in Immune Functions and Diseases 2, 2000, Kluwer Academic/Plenum Publishers, Chapter: Natural Substrates of Dipeptidyl Peptidase IV", 2000, vol. -, No. -, pp. -.
Roberts, M.J et al., Advanced Drug Delivery Reviews, "Chemistry for Peptide and Protein Pegylation", 2002, vol. 54, No. -, pp. 459-476.
Soltero and Ekwurlbe, Innovations in Pharmaceutical Technology, "-", 2001, vol. 1, No. -, pp. 106-110.
Still, J. Gordon, Diabetes Metabolism Research Reviews, "-", 2002, vol. 18, No. suppl1, pp. 29-37.
Veronese F. M, Biomaterials, "Peptide and Protein Pegylation: A Review of Porblems and Solutions", 2001, vol. 22, No. 5, pp. 405-417.
Watanabe et al., Journal of Endocrinology, "-", 1994, vol. 140 , No. -, pp. 45-52.
Zalipsky and Harris, -, "Textbook: Poly(Ethylene Glycol), 1997, American Chemical Society, Chapter 1: Introduction to Chemistry and Biological Application of Poly(Ethylene Glycol)", 1997, vol. -, No. Chapt1, pp. -.
Testing the NPL retreival.
Holst, Current Medicinal Chemistry, "-", 1999, vol. 6, No. -, pp. 1005-1017.
Nauck et al., Drug News & Perspectives, "-", 2003, vol. 16, No. 7, pp. 413-422.

\* cited by examiner

*Primary Examiner* — Marcela M Cordero Garcia
(74) *Attorney, Agent, or Firm* — Jianjie Hu

(57) ABSTRACT

Novel GLP-1 compounds and their therapeutic use.

43 Claims, No Drawings

SEQUENCE LISTING

```
<160> NUMBER OF SEQ ID NOS: 5

<210> SEQ ID NO 1
<211> LENGTH: 31
<212> TYPE: PRT
<213> ORGANISM: homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: heloderma suspectum
<220> FEATURE:
<221> NAME/KEY: MOD RES
<222> LOCATION: (39)..(39)
<223> OTHER INFORMATION: Amidation of carboxy group

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: Xaa = L-histidine, D-histidine, desamino-
      histidine, 2-amino-histidine, beta-hydroxy-histidine,
      homohistidine, N-alpha-acetyl-histidine, alpha-fluoromethyl-
      histidine, alpha-methyl-histidine, 2-, 3-, or 4-pyridylalanine
<220> FEATURE:
<221> NAME/KEY: MISC_FEATURE
<222> LOCATION: (2)..(2)
<223> OTHER INFORMATION: Xaa is Ala, D-Ala, Gly, Val, Leu, Ile, Lys,
      Aib, (1-aminocyclopropyl) carboxylic acid, (1-aminocyclobutyl)
      carboxylic acid, (1-aminocyclopentyl) carboxylic acid,
      (1-aminocyclohexyl) carboxylic acid,
<220> FEATURE:
<221> NAME/KEY: MISC_FEATURE
<222> LOCATION: (2)..(2)
<223> OTHER INFORMATION: cont. (1-aminocycloheptyl) carboxylic acid or
      (1-aminocyclooctyl) carboxylic acid.
<220> FEATURE:
<221> NAME/KEY: MISC_FEATURE
<222> LOCATION: (10)..(10)
<223> OTHER INFORMATION: Xaa is Val or Leu.
<220> FEATURE:
<221> NAME/KEY: MISC_FEATURE
<222> LOCATION: (12)..(12)
<223> OTHER INFORMATION: Xaa at position 12 is Ser, Lys or Arg.
<220> FEATURE:
<221> NAME/KEY: MISC_FEATURE
<222> LOCATION: (13)..(13)
<223> OTHER INFORMATION: Xaa at position 13 is Tyr or Gln.
<220> FEATURE:
<221> NAME/KEY: MISC_FEATURE
<222> LOCATION: (14)..(14)
<223> OTHER INFORMATION: Xaa at position 14 is Leu or Met.
<220> FEATURE:
<221> NAME/KEY: MISC_FEATURE
<222> LOCATION: (16)..(16)
<223> OTHER INFORMATION: Xaa at position 16 is Gly, Glu or Aib.
<220> FEATURE:
<221> NAME/KEY: MISC_FEATURE
<222> LOCATION: (17)..(17)
<223> OTHER INFORMATION: Xaa at position 17 is Gln, Glu, Lys or Arg.
<220> FEATURE:
<221> NAME/KEY: MISC_FEATURE
<222> LOCATION: (19)..(19)
<223> OTHER INFORMATION: Xaa at position 19 is Ala or Val.
<220> FEATURE:
<221> NAME/KEY: MISC_FEATURE
<222> LOCATION: (20)..(20)
<223> OTHER INFORMATION: Xaa is Lys, Glu or Arg.
<220> FEATURE:
<221> NAME/KEY: MISC_FEATURE
<222> LOCATION: (21)..(21)
<223> OTHER INFORMATION: Xaa at position 21 is Glu or Leu.
<220> FEATURE:
<221> NAME/KEY: MISC_FEATURE
<222> LOCATION: (24)..(24)
<223> OTHER INFORMATION: Xaa at position 24 is Ala, Glu or Arg.
<220> FEATURE:
<221> NAME/KEY: MISC_FEATURE
<222> LOCATION: (27)..(27)
<223> OTHER INFORMATION: Xaa at position 27 is Val or Lys.
<220> FEATURE:
<221> NAME/KEY: MISC_FEATURE
<222> LOCATION: (28)..(28)
<223> OTHER INFORMATION: Xaa at position 28 is Lys, Glu, Asn or Arg.
<220> FEATURE:
<221> NAME/KEY: MISC_FEATURE
<222> LOCATION: (29)..(29)
<223> OTHER INFORMATION: Xaa at position 29 is Gly or Aib.
<220> FEATURE:
<221> NAME/KEY: MISC_FEATURE
<222> LOCATION: (30)..(30)
<223> OTHER INFORMATION: Xaa at position 30 is Arg, Gly or Lys.
<220> FEATURE:
<221> NAME/KEY: MISC_FEATURE
<222> LOCATION: (31)..(31)
<223> OTHER INFORMATION: Xaa at position 31 is Gly, Ala, Glu, Pro, Lys,
      or is absent
<220> FEATURE:
<221> NAME/KEY: MISC_FEATURE
```

-continued

```
<222> LOCATION: (32)..(32)
<223> OTHER INFORMATION: Xaa at position 32 is Lys, Ser, or is absent.
      Amidation may occur at this position.
<220> FEATURE:
<221> NAME/KEY: MISC_FEATURE
<222> LOCATION: (33)..(33)
<223> OTHER INFORMATION: Xaa at position 33 is Ser, Lys, or is absent.
      Amidation may occur at this position.
<220> FEATURE:
<221> NAME/KEY: MISC_FEATURE
<222> LOCATION: (34)..(34)
<223> OTHER INFORMATION: Xaa at position 34 is Gly, or is absent.
      Amidation may occur at this position.
<220> FEATURE:
<221> NAME/KEY: MISC_FEATURE
<222> LOCATION: (35)..(35)
<223> OTHER INFORMATION: Xaa at position 35 is Ala, or is absent.
      Amidation may occur at this position.
<220> FEATURE:
<221> NAME/KEY: MISC_FEATURE
<222> LOCATION: (36)..(36)
<223> OTHER INFORMATION: Xaa at position 36 is Pro, or is absent.
      Amidation may occur at this position.
<220> FEATURE:
<221> NAME/KEY: MISC_FEATURE
<222> LOCATION: (37)..(37)
<223> OTHER INFORMATION: Xaa at position 37 is Pro, or is absent.
      Amidation may occur at this position.
<220> FEATURE:
<221> NAME/KEY: MISC_FEATURE
<222> LOCATION: (38)..(38)
<223> OTHER INFORMATION: Xaa at position 38 is Pro, or is absent.
      Amidation may occur at this position.
<220> FEATURE:
<221> NAME/KEY: MISC_FEATURE
<222> LOCATION: (39)..(39)
<223> OTHER INFORMATION: Xaa at position 39 is Ser, or is absent.
      Amidation may occur at this position.

<400> SEQUENCE: 3

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa
        35

<210> SEQ ID NO 4
<211> LENGTH: 32
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, N-alpha-acetyl-histidine,
      alpha-fluoromethyl-histidine,
<220> FEATURE:
<221> NAME/KEY: MISC_FEATURE
<222> LOCATION: (1)..(1)
<223> OTHER INFORMATION: cont. alpha-methyl-histidine, 3-pyridylalanine,
      2-pyridylalanine, or 4-pyridylalanine
<220> FEATURE:
<221> NAME/KEY: MISC_FEATURE
<222> LOCATION: (2)..(2)
<223> OTHER INFORMATION: Xaa at position 2 is Ala, D-Ala, Gly, Val, Leu,
      Ile, Lys, Aib, (1-aminocyclopropyl) carboxylic acid,
      (1-aminocyclobutyl) carboxylic acid, (1-aminocyclopentyl)
      carboxylic acid, (1-aminocyclohexyl) carboxylic acid,
<220> FEATURE:
<221> NAME/KEY: MISC_FEATURE
<222> LOCATION: (2)..(2)
```

```
<223> OTHER INFORMATION: cont. (1-aminocycloheptyl) carboxylic acid or
      (1-aminocyclooctyl) carboxylic acid.
<220> FEATURE:
<221> NAME/KEY: MISC_FEATURE
<222> LOCATION: (12)..(12)
<223> OTHER INFORMATION: Xaa at position 12 is Ser, Lys or Arg.
<220> FEATURE:
<221> NAME/KEY: MISC_FEATURE
<222> LOCATION: (16)..(16)
<223> OTHER INFORMATION: Xaa at position 16 is Gly, Glu or Aib.
<220> FEATURE:
<221> NAME/KEY: MISC_FEATURE
<222> LOCATION: (17)..(17)
<223> OTHER INFORMATION: Xaa at position 17 is Gln, Glu, Lys or Arg.
<220> FEATURE:
<221> NAME/KEY: MISC_FEATURE
<222> LOCATION: (20)..(20)
<223> OTHER INFORMATION: Xaa at position 20 is Lys, Glu or Arg.
<220> FEATURE:
<221> NAME/KEY: MISC_FEATURE
<222> LOCATION: (24)..(24)
<223> OTHER INFORMATION: Xaa at position 24 is Ala, Glu or Arg.
<220> FEATURE:
<221> NAME/KEY: MISC_FEATURE
<222> LOCATION: (28)..(28)
<223> OTHER INFORMATION: Xaa at position 28 is Lys, Glu or Arg.
<220> FEATURE:
<221> NAME/KEY: MISC_FEATURE
<222> LOCATION: (29)..(29)
<223> OTHER INFORMATION: Xaa at position 29 is Gly or Aib.
<220> FEATURE:
<221> NAME/KEY: MISC_FEATURE
<222> LOCATION: (30)..(30)
<223> OTHER INFORMATION: Xaa at position 30 is Arg or Lys.
<220> FEATURE:
<221> NAME/KEY: MISC_FEATURE
<222> LOCATION: (31)..(31)
<223> OTHER INFORMATION: Xaa at position 31 is Gly, Ala, Glu or Lys.
<220> FEATURE:
<221> NAME/KEY: MISC_FEATURE
<222> LOCATION: (32)..(32)
<223> OTHER INFORMATION: Xaa at position 32 is Lys, or is absent.

<400> SEQUENCE: 4

Xaa Xaa Glu Gly Thr Phe Thr Ser Asp Val Ser Xaa Tyr Leu Glu Xaa
1               5                   10                  15

Xaa Ala Ala Xaa Glu Phe Ile Xaa Trp Leu Val Xaa Xaa Xaa Xaa Xaa
            20                  25                  30

<210> SEQ ID NO 5
<211> LENGTH: 44
<212> TYPE: PRT
<213> ORGANISM: Artificial Sequence
<220> FEATURE:
<223> OTHER INFORMATION: synthetic
<220> FEATURE:
<221> NAME/KEY: MOD RES
<222> LOCATION: (44)..(44)
<223> OTHER INFORMATION: Amidation of carboxyl group

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
            35                  40
```

GLP-1 COMPOUNDS

CROSS-REFERENCE TO RELATED PATENT APPLICATIONS

This application is a continuation of U.S. application Ser. No. 11/454,804, filed Jun. 16, 2006, which is a continuation of International Patent Application No. PCT/DK2004/000886 filed Dec. 17, 2004 and claims priority of U.S. Patent Application Nos. 60/531,053, filed Dec. 19, 2003, and 60/587,181, filed Jul. 12, 2004 and Danish Patent Application Nos. PA 2003 01885, filed Dec. 18, 2003 and PA 2004 01090, filed Jul. 9, 2004; the contents of all above-named applications are incorporated herein by reference.

FIELD OF THE INVENTION

The present invention relates to novel GLP-1 compounds, to pharmaceutical compositions comprising these compounds and to the use of the compounds for the treatment of diseases related to diabetes.

BACKGROUND OF THE INVENTION

Diabetes mellitus is a metabolic disorder in which the ability to utilize glucose is partly or completely lost. About 5% of all people suffer from diabetes and the disorder approaches epidemic proportions. Since the introduction of insulin in the 1920's, continuous efforts have been made to improve the treatment of diabetes mellitus.

One peptide expected to become very important in the treatment of diabetes is glucagon-like peptide-1 (GLP-1). Human GLP-1 is a 37 amino acid residue peptide originating from pre-proglucagon which is synthesized i.a. in the L-cells in the distal ileum, in the pancreas and in the brain. GLP-1 is an important gut hormone with regulatory function in glucose metabolism and gastrointestinal secretion and metabolism. GLP-1 stimulates insulin secretion in a glucose-dependant manner, stimulates insulin biosynthesis, promotes beta cell rescue, decreases glucagon secretion, gastric emptying and food intake. Human GLP-1 is hydrolysed to GLP-1(7-37) and GLP-1(7-36)-amide which are both insulinotropic peptides. A simple system is used to describe fragments and analogues of this peptide. Thus, for example, [Gly$^8$]GLP-1(7-37) designates an analogue of GLP-1(7-37) formally derived from GLP-1(7-37) by substituting the naturally occurring amino acid residue in position 8 (Ala) by Gly. Similarly, (N$^{\epsilon 34}$-tetradecanoyl)[Lys$^{34}$] GLP-1(7-37) designates GLP-1(7-37) wherein the ε-amino group of the Lys residue in position 34 has been tetradecanoylated. PCT publications WO 98/08871 and WO 99/43706 disclose stable derivatives of GLP-1 analogues, which have a lipophilic substituent. These stable derivatives of GLP-1 analogues have a protracted profile of action compared to the corresponding GLP-1 analogues.

In the last decade a number of peptides have been isolated from the venom of the Gila monster lizards (*Heloderma suspectum* and *Heloderma horridum*). Exendin-4 is a 39 amino acid residue peptide isolated from the venom of *Heloderma suspectum*, and this peptide shares 52% homology with GLP-1(7-37) in the overlapping region. Exendin-4 is a potent GLP-1 receptor agonist which has been shown to stimulate insulin release and ensuing lowering of the blood glucose level when injected into dogs. The group of exendin-4(1-39), certain fragments thereof, analogs thereof and derivatives thereof, are potent insulinotropic agents. Most importantly the group of exendin-4(1-39), insulinotropic fragments thereof, insulinotropic analogs thereof and insulinotropic derivatives thereof.

Common to GLP-1 and exendins are that an extensive amount of variants have been synthesized and studied in particular in relation the plasma half-life. Low plasma half-lifes may be due to chemical stability towards peptidases (mainly dipeptidyl aminopeptidase IV) and to renal clearance. However, these analogues and derivatives of insulionotropic peptides lack a satisfactory bioavailability when administered by the pulmonary route, i.e. when administered to the lower respiratory tract such as through the bronchioles or alveoli.

WO 00/66629 discloses modified exendin agonists which have been coupled to polyethyleneglycol via a lysine residue to decrease renal clearance.

WO 03/40309 discloses peptide acting as both GLP-1 receptor agonists and glucagon receptor antagonists. Among the disclosed peptides are two peptides which have been coupled to polyethyleneglycol via a C-terminal cycleine residue.

WO 2004/093823 discloses polyethylene glycolated GLOP-1 peptides.

Pulmonary administration of GLP-1 peptides have been disclosed in WO 01/51071 and WO 00/12116.

The insulinotropic peptides derived from GLP-1 and Exendin-4 stimulated insulin release only when plasma glucose levels are high, the risk of hypoglycemic events is reduced. Thus, the peptides are particularly useful for patients with diabetes who no longer respond to OHA's (oral hyperglycemic agents) and who should from a strict medical point of view be administered insulin. Patients and to some extent also doctors are often not keen on initiating insulin treatment before this is absolutely necessary, presumably because of the fear of hypoglycemic events or the fear of injections/needles. Thus, there is a need for insulinotropic peptides which are sufficiently potent and which can be administered by the pulmonary route. Thus, it is an object of the present invention to provide insulinotropic peptides which have sufficient pulmonary bioavailability to serve as an alternative to peptides for parenteral administration. Insulinotropic peptides having pulmonary bioavailability is a balance between potency and bioavailability. It is also an object of the present invention to provide insulinotropic peptides which are less prone to aggregation, a well known problem associated with the glucagon-like peptides. Being less prone to aggregation facilitates economical manufacturing processes as well as enabling the compounds to be administered by medical infusion pumps.

DEFINITIONS

In the present specification, the following terms have the indicated meaning:

The term "polypeptide" and "peptide" as used herein means a compound composed of at least five constituent amino acids connected by peptide bonds. The constituent amino acids may be from the group of the amino acids encoded by the genetic code and they may natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib α-aminoisobutyric acid), Abu (α-aminobutyric acid), Tle (tert-butylglycine), β-alanine, 3-aminomethyl benzoic acid, anthranilic acid.

The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. A simple system is often used to describe analogues: For example [Arg$^{34}$]GLP-1(7-37)Lys designates a GLP-1(7-37) analogue wherein the naturally occurring lysine at position 34 has been substituted with arginine and wherein a lysine has been added to the terminal amino acid residue, i.e. to the Gly$^{37}$. All amino acids for which the optical isomer is not stated is to be understood to mean the L-isomer.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. An example of a derivative of GLP-1(7-37) is N$^{\epsilon 26}$-((4S)-4-(hexadecanoylamino)-butanoyl)[Arg$^{34}$, Lys$^{26}$]GLP-1-(7-37).

The term "insulinotropic agent" as used herein means a compound which is an agonist of the human GLP-1 receptor, i.e. a compound which stimulates the formation of cAMP in a suitable medium containing the human GLP-1 receptor (one such medium disclosed below). The potency of an insulinotropic agent is determined by calculating the EC$_{50}$ value from the dose-response curve as described below.

Baby hamster kidney (BHK) cells expressing the cloned human GLP-1 receptor (BHK-467-12A) were grown in DMEM media with the addition of 100 IU/mL penicillin, 100 µg/mL streptomycin, 5% fetal calf serum and 0.5 mg/mL Geneticin G-418 (Life Technologies). The cells were washed twice in phosphate buffered saline and harvested with Versene. Plasma membranes were prepared from the cells by homogenisation with an Ultraturrax in buffer 1 (20 mM HEPES-Na, 10 mM EDTA, pH 7.4). The homogenate was centrifuged at 48,000×g for 15 min at 4° C. The pellet was suspended by homogenization in buffer 2 (20 mM HEPES-Na, 0.1 mM EDTA, pH 7.4), then centrifuged at 48,000×g for 15 min at 4° C. The washing procedure was repeated one more time. The final pellet was suspended in buffer 2 and used immediately for assays or stored at −80° C.

The functional receptor assay was carried out by measuring cyclic AMP (cAMP) as a response to stimulation by the insulinotropic agent. cAMP formed was quantified by the AlphaScreen™ cAMP Kit (Perkin Elmer Life Sciences). Incubations were carried out in half-area 96-well microtiter plates in a total volume of 50 µL buffer 3 (50 mM Tris-HCl, 5 mM HEPES, 10 mM MgCl$_2$, pH 7.4) and with the following additions: 1 mM ATP, 1 µM GTP, 0.5 mM 3-isobutyl-1-methylxanthine (IBMX), 0.01% Tween-20, 0.1% BSA, 6 µg membrane preparation, 15 µg/mL acceptor beads, 20 µg/mL donor beads preincubated with 6 nM biotinyl-cAMP. Compounds to be tested for agonist activity were dissolved and diluted in buffer 3. GTP was freshly prepared for each experiment. The plate was incubated in the dark with slow agitation for three hours at room temperature followed by counting in the Fusion™ instrument (Perkin Elmer Life Sciences). Concentration-response curves were plotted for the individual compounds and EC$_{50}$ values estimated using a four-parameter logistic model with Prism v. 4.0 (GraphPad, Carlsbad, Calif.).

The term "GLP-1 peptide" as used herein means GLP-1 (7-37) (SEQ ID No 1), a GLP-1(7-37) analogue, a GLP-1 (7-37) derivative or a derivative of a GLP-1(7-37) analogue. In one embodiment the GLP-1 peptide is an insulinotropic agent.

The term "exendin-4 peptide" as used herein means exendin-4(1-39) (SEQ ID No 2), an exendin-4(1-39) analogue, an exendin-4(1-39) derivative or a derivative of an exendin-4(1-39) analogue. In one embodiment the exendin-4 peptide is an insulinotropic agent.

The term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV. In one embodiment a DPP-IV protected peptide is more resistant to DPP-IV than GLP-1(7-37) or Exendin-4(1-39).

Resistance of a Peptide to Degradation by Dipeptidyl Aminopeptidase IV is Determined by the Following Degradation Assay:

Aliquots of the peptide (5 nmol) are incubated at 37° C. with 1 µL of purified dipeptidyl aminopeptidase IV corresponding to an enzymatic activity of 5 mU for 10-180 minutes in 100 µL of 0.1 M triethylamine-HCl buffer, pH 7.4. Enzymatic reactions are terminated by the addition of 5 µL of 10% trifluoroacetic acid, and the peptide degradation products are separated and quantified using HPLC analysis. One method for performing this analysis is: The mixtures are applied onto a Vydac C18 widepore (30 nm pores, 5 µm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

The term "mPEGyl" means a polydisperse or monodisperse radical of the structure

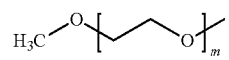

wherein m is an integer larger than 1. Thus, a mPEGyl wherein m is 90 has a molecular weight of 3991 Da, i.e. approx 4 kDa. Likewise, a mPEGyl with an average molecular weight of 20 kDa has an average m of 454. Due to the process for producing mPEGyl these molecules often have a distribution of molecular weights. This distribution is described by the polydispersity index.

The term "polydispersity index" as used herein means the ratio between the weight average molecular weight and the number average molecular weight, as known in the art of polymer chemistry (see e.g. "Polymer Synthesis and Characterization", J.a: Nairn, University of Utah, 2003). The polydispersity index is a number which is greater than or equal to one, and it may be estimated from Gel Permeation Chromatographic data. When the polydispersity index is one the product is monodisperse, and is thus made up of a single molecular weight. When the polydispersity index is greater than one it is a measure of the polydispersity of that polymer, i.e. how broad the distribution of polymers with different molecular weights is.

The term "$C_{1-6}$-alkyl" as used herein means a saturated, branched, straight or cyclic hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl, cyclohexane and the like.

The term "pharmaceutically acceptable" as used herein means suited for normal pharmaceutical applications, i.e. giving rise to no adverse events in patients etc.

The term "heavy atom" as used herein means an atom having a molar weight equal to or larger than carbon, e.g. C, N, O and S.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active compound or a salt thereof together with pharmaceutical excipients such as buffer, preservative, and optionally a tonicity modifier and/or a stabilizer. Thus a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

DESCRIPTION OF THE INVENTION

In one aspect the present invention relates to a compound having the structure of the formula (I):

Insulinotropic agent(-Y—C*)$_f$-Q                  (I)

wherein

Insulinotropic agent is a radical derived from an insulinotropic peptide which binds to the human GLP-1 receptor, or a radical derived from a peptide in which 22 positions out of the first 30 are identical to those found in corresponding positions in GLP-1 or found in corresponding positions in Exendin-4, and Y is a bivalent connecting chemical group connecting C* with the Insulinotropic agent, and C* is a bivalent polar separating chemical group where 50-20% of the heavy atoms are either O or N, and f is 0 or 1 and Q is selected from

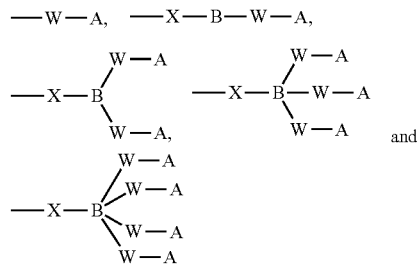

wherein

A is a polar chemical group of a single molecular size (monodisperse) or of several molecular sizes (polydisperse) where 50-20% of the heavy atoms are independently oxygen or nitrogen, and W is a bivalent chemical group whereby A is connected, and X is a bivalent connecting chemical group whereby B is connected, and B is a connecting or branching chemical group.

In another aspect the present invention relates to a compound having the structure of the formula (I):

Insulinotropic agent(-Y—C*)$_f$-Q                  (I)

wherein

Insulinotropic agent is a radical derived from an insulinotropic peptide which binds to the human GLP-1 receptor, or a radical derived from a peptide in which 22 positions out of the first 30 are identical to those found in corresponding positions in GLP-1 or found in corresponding positions in Exendin-4, with the proviso that the C-terminal amino acid residue of said insulinotropic agent is not cysteine, and Y is a bivalent connecting chemical group connecting C* with the Insulinotropic agent, and C* is a bivalent polar separating chemical group where 50-20% of the heavy atoms are either O or N, and f is 0 or 1 and Q is selected from

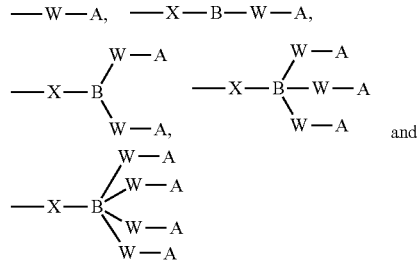

wherein

A is a polar chemical group of a single molecular size (monodisperse) or of several molecular sizes (polydisperse) where 50-20% of the heavy atoms are independently oxygen or nitrogen, and W is a bivalent chemical group whereby A is connected, and X is a bivalent connecting chemical group whereby B is connected, and B is a connecting or branching chemical group.

The general formula (I) and the encompassed peptide radical is to be understood as follows.

The following compound is encompassed by formula (I): N$^{\epsilon 37}$-(3-(mPEGyl)propionyl)[Aib$^{8,22,35}$,Lys$^{37}$]GLP-1(7-37) amide wherein mPEGyl is polydisperse and has a molecular weight of approximately 2 kDa

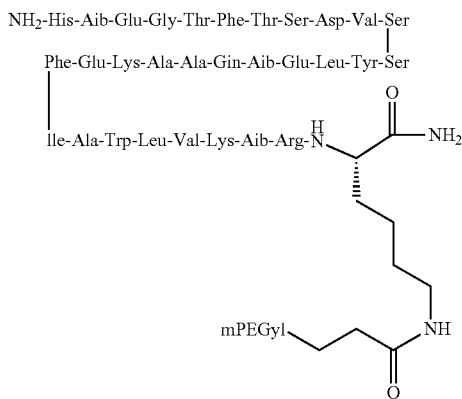

The insulinotropic agent is the radical comprising the peptide including the four methylene groups in the lysine residue in position 37. The group A is the mPEGyl-CH$_2$CH$_2$— wherein mPEGyl has a molecular weight of approximately 2 kDa. The bivalent chemical group W whereby mPEGyl-CH$_2$CH$_2$— is connected to the radical derived from the insulinotropic peptide is the amide —C(O)—NH—.

In one embodiment of the invention A is a monodisperse or polydisperse chemical group having the structure —(CH$_2$)$_l$O[(CH$_2$)$_n$O]$_m$(CH$_2$)$_p$—H, where l, n and p independently are an integer in the range from 1 to 10, m is an integer in the range from 1 to 5000, and where m multiplied by n+1 is less than 10000.

In another embodiment of the invention A is a monodisperse or polydisperse chemical group having the structure —(CH$_2$)$_l$C(=O)[(CH$_2$)$_n$O]$_m$(CH$_2$)$_p$—H, where l, n and p independently are an integer in the range from 1 to 10, m is an integer in the range from 1 to 5000, and where m multiplied by n+1 is less than 10000.

In another embodiment of the invention n is 2 or 3.

In another embodiment of the invention m is in the range from 10-1000, or in the range from 20-250.

In another embodiment of the invention A is a monodisperse or polydisperse chemical group having the structure —(Z$^1$(CH$_2$)$_l$O[(CH$_2$)$_2$O]$_m$(CH$_2$)$_p$—NR$^1$)$_q$—Z$^2$, where Z$^1$ is —CO— or —CO—(CH$_2$)$_n$—CO—NH—, and Z$^2$ is —R$^1$, —CO—(CH$_2$)$_n$—R$^1$, —(CH$_2$)$_l$O[(CH$_2$)$_2$O]$_m$(CH$_2$)$_p$—R$^1$ wherein l and n and p independently are integers in the range from 1 to 10, and R$^1$ is —OH, —NH$_2$, —NH—R$^2$, —NH(—R$^2$)—R$^2$, —COOH, C$_{1-6}$-alkyl, or —NH—CH(R$^2$)—COOH, and where m and q are independently integers in the range from 1 to 20, and where l, n and p are independently integers in the range from 1 to 6, and R$^2$ is hydrogen or C$_{1-6}$-alkyl.

In another embodiment of the invention A is mPEGyl.

In another embodiment of the invention A is mPEGyl-C(=O)—(CH$_2$)$_r$—, wherein r is an integer in the range from 1-10.

In another embodiment of the invention A is monodisperse, i.e. it is made up of only one component.

In another embodiment of the invention A has a polydispersity index from 1.00 to 1.10.

In another embodiment of the invention A is polydisperse and preferably having a polydispersity index which is less than 1.2, less than 1.1, less than 1.05, less than 1.03, less than 1.02, less than 1.010, less than 1.008, less than 1.005 or less than 1.0025.

In another embodiment of the invention the branching chemical group B is selected from

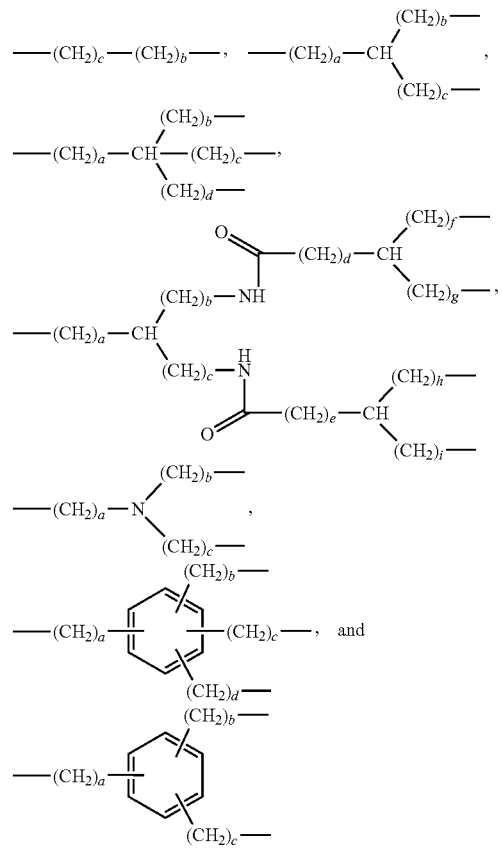

wherein a, b, c, d, e, f, g, h, i are integers independently selected from the range from 0 to 24.

In another embodiment of the invention the branching group B is

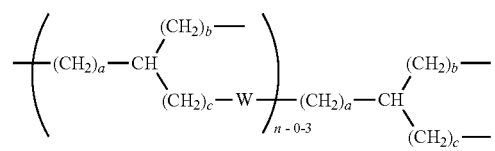

wherein a, b, c are integers independently selected from the range from 0 to 24.

In another embodiment of the invention the branching chemical group B is selected from

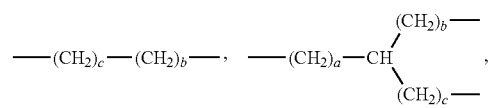

-continued

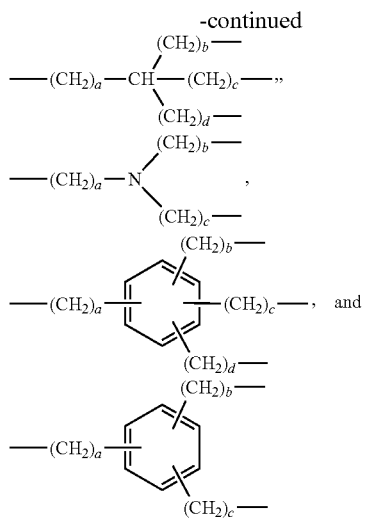

wherein a, b, c, d, e, f, g, h, i are integers independently selected from the range from 0 to 24.

In another embodiment of the invention the insulinotropic agent is attached to B via the left hand terminal of B.

In another embodiment of the invention a+b is less than 6 or a+b+c is less than 14 or a+b+c+d+e+f+g+h+l is less than 16.

In another embodiment of the invention a is 0 or 1 and b, c, d, e, f, h and i are all in the range from 0 to 5.

In another embodiment of the invention a, c, d, e, g and i are all 0 and b, f and h are all in the range from 1 to 4.

In another embodiment of the invention a, c, d, e, g and l are all 0 and b, f and h are all in the range from 1 to 4.

In another embodiment of the invention, W and X are independently selected from the bi-valent connecting chemical groups comprising amides: —C(O)—NR—, where R is hydrogen or $C_{1-6}$-alkyl,
amines: —NR—, where R is hydrogen or $C_{1-6}$-alkyl,
thioethers: —S—, —S—$(CH_2)_2$—$SO_2$— or

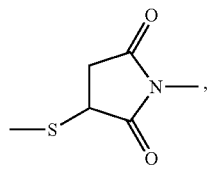

ethers: —O—,
urethanes: —N($R^1$)—CO—N($R^2$)—, where $R^1$ and $R^2$ independently is hydrogen or $C_{1-6}$-alkyl,
carbamates: —O—CO—N(R)—, where R is hydrogen or $C_{1-6}$-alkyl,
hydrazines:

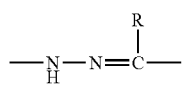

where R is hydrogen or $C_{1-6}$-alkyl,
oximes: —O—N=C(—R)—, where R is hydrogen or $C_{1-6}$-alkyl,
oxazolidines or thiazolidines:

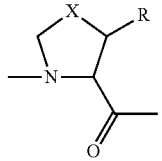

R=H or $CH_3$, X=S or O, and

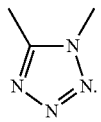

The hydrazine derivatives of the formula,

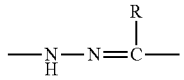

where R is hydrogen or $C_{1-6}$-alkyl may be formed by reaction of an aldehyde derivative (—CO—H) or a ketone derivative (—CO—R) with
  hydrazine derivatives (—NH—$NH_2$) or
  hydrazine carboxylate derivatives (—O—C(O)—NH—$NH_2$) or
  semicarbazide derivatives (—NH—C(O)—NH—$NH_2$) or
  thiosemicarbazide derivatives (—NH—C(S)—NH—$NH_2$) or
  carbonic acid dihydrazide derivatives (—NHC(O)—NH—NH—C(O)—NH—$NH_2$) or
  carbazide derivatives (—NH—NH—C(O)—NH—$NH_2$) or
  thiocarbazide derivatives (—NH—NH—C(S)—NH—$NH_2$) or
  aryl hydrazide derivatives (—NH—C(O)—$C_6H_4$—NH—$NH_2$) or
  hydrazide derivatives (—C(O)—NH—$NH_2$).

The oximes of the formula —O—N=C(—R)—, where R is hydrogen or $C_{1-6}$-alkyl and may be formed by reaction of an aldehyde (—CO—H) or a ketone (—CO—R) with
  oxylamine (—O—$NH_2$) or
  —C(O)—O—$NH_2$ or
  —NH—C(O)—O—$NH_2$ or
  —NH—C(S)—O—$NH_2$.

In another embodiment of the invention W is —C(O)—NR—, where R is hydrogen or $C_{1-6}$-alkyl.

In another embodiment of the invention the insulinotropic agent is attached to W via the left hand terminal (the carbon) of W.

In another embodiment of the invention the insulinotropic agent is attached to W via the right hand terminal (the nitrogen) of W.

In another embodiment of the invention, f is 0.

In another embodiment of the invention C* is —$(CH_2)_{n1}$O[$(CH_2)_{n2}$O]$_{n3}$$(CH_2)_{n4}$—, where n1, n2 and n4 independently is an integer in the range from 1 to 10, n3 is an integer in the range from 1 to 5000, and where n3 multiplied by n2+1 is less than 10000.

In another embodiment of the invention n2 is 2 or 3.
In another embodiment of the invention n3 is in the range from 1-20.

In another embodiment of the invention C* is —$(CH_2)_{n5}$—, where n5 is an integer in the range from 1 to 10.

In another embodiment of the invention Y is selected from the bi-valent connecting chemical groups comprising
amides: —C(O)—NR—, where R is hydrogen or $C_{1-6}$-alkyl,
amines: —NR—, where R is hydrogen or $C_{1-6}$-alkyl,
thioethers: —S—, —S—$(CH_2)_2$—$SO_2$— or

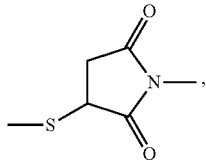

ethers: —O—,
urethanes: —N($R^1$)—CO—N($R^2$)—, where $R^1$ and $R^2$ independently is hydrogen or $C_{1-6}$-alkyl,
carbamates: —O—CO—N(R)—, where R is hydrogen or $C_{1-6}$-alkyl,
hydrazines:

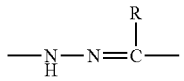

where R is hydrogen or $C_{1-6}$-alkyl,
oximes: —O—N=C(—R)—, where R is hydrogen or $C_{1-6}$-alkyl,
oxazolidines or thiazolidines:

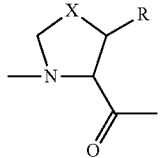

R=H or $CH_3$, X=S or O, and

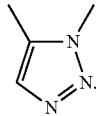

In another embodiment of the invention the insulinotropic agent is a DPPIV protected peptide.

In another embodiment of the invention the insulinotropic agent has an $EC_{50}$ of less than 1 nM as determined by the functional receptor assay disclosed herein.

In another embodiment of the invention the insulinotropic agent has an $EC_{50}$ of less than 300 pM, less than 200 pM or less than 100 pM as determined by the functional receptor assay disclosed herein.

In another embodiment of the invention the insulinotropic agent is derived from a peptide having a length between 27 and 45 amino acid residues in which 22 out of the first 28 amino acid residues are identical to those found in corresponding positions in GLP-1(7-37) (SEQ ID No. 1) or in corresponding positions in Exendin-4(1-39) (SEQ ID No. 2).

In another embodiment of the invention the insulinotropic agent is derived from a peptide having a length between 28 and 45 amino acid residues in which 22 out of the first 28 amino acid residues are identical to those found in corresponding positions in GLP-1(7-37) or in corresponding positions in Exendin-4(1-39).

In another embodiment of the invention the insulinotropic agent is selected from a peptide comprising the amino acid sequence of the formula (II):

Formula (II)
(SEQ ID No: 3)
$Xaa_7$-$Xaa_8$-Glu-Gly-Thr-Phe-Thr-Ser-Asp-$Xaa_{16}$-Ser- $Xaa_{18}$-$Xaa_{19}$-$Xaa_{20}$-Glu-$Xaa_{22}$-$Xaa_{23}$-Ala-$Xaa_{25}$-$Xaa_{26}$-

$Xaa_{27}$-Phe-Ile-$Xaa_{30}$-Trp-Leu-$Xaa_{33}$-$Xaa_{34}$-$Xaa_{35}$-$Xaa_{36}$-

$Xaa_{37}$-$Xaa_{38}$-$Xaa_{39}$-$Xaa_{40}$-$Xaa_{41}$-$Xaa_{42}$-$Xaa_{43}$-$Xaa_{44}$-

$Xaa_{45}$-$Xaa_{46}$ wherein
$Xaa_7$ is L-histidine, D-histidine, desamino-histidine, 2-amino-histidine, β-hydroxy-histidine, homohistidine, $N^α$-acetyl-histidine, α-fluoromethyl-histidine, α-methyl-histidine, 3-pyridylalanine, 2-pyridylalanine or 4-pyridylalanine;
$Xaa_8$ is Ala, D-Ala, Gly, Val, Leu, Ile, Lys, Aib, (1-aminocyclopropyl)carboxylic acid, (1-aminocyclobutyl)carboxylic acid, (1-aminocyclopentyl)carboxylic acid, (1-aminocyclohexyl)carboxylic acid, (1-aminocycloheptyl) carboxylic acid, or (1-aminocyclooctyl)carboxylic acid;
$Xaa_{16}$ is Val or Leu;
$Xaa_{18}$ is Ser, Lys or Arg;
$Xaa_{19}$ is Tyr or Gln;
$Xaa_{20}$ is Leu or Met;
$Xaa_{22}$ is Gly, Glu or Aib;
$Xaa_{23}$ is Gln, Glu, Lys or Arg;
$Xaa_{25}$ is Ala or Val;
$Xaa_{26}$ is Lys, Glu or Arg;
$Xaa_{27}$ is Glu or Leu;
$Xaa_{30}$ is Ala, Glu or Arg;
$Xaa_{33}$ is Val or Lys;
$Xaa_{34}$ is Lys, Glu, Asn or Arg;
$Xaa_{35}$ is Gly or Aib;
$Xaa_{36}$ is Arg, Gly or Lys;
$Xaa_{37}$ is Gly, Ala, Glu, Pro, Lys, amide or is absent;
$Xaa_{38}$ is Lys, Ser, amide or is absent.
$Xaa_{39}$ is Ser, Lys, amide or is absent;
$Xaa_{40}$ is Gly, amide or is absent;
$Xaa_{41}$ is Ala, amide or is absent;
$Xaa_{42}$ is Pro, amide or is absent;
$Xaa_{43}$ is Pro, amide or is absent;
$Xaa_{44}$ is Pro, amide or is absent;
$Xaa_{45}$ is Ser, amide or is absent;
$Xaa_{46}$ is amide or is absent;
provided that if $Xaa_{38}$, $Xaa_{39}$, $Xaa_{40}$, $Xaa_{41}$, $Xaa_{42}$, $Xaa_{43}$, $Xaa_{44}$, $Xaa_{45}$ or $Xaa_{46}$ is absent then each amino acid residue downstream is also absent.

In another embodiment of the invention the insulinotropic agent is a peptide comprising the amino acid sequence of formula (III):

Formula (III)
(SEQ ID No: 4)
$Xaa_7$-$Xaa_8$-Glu-Gly-Thr-Phe-Thr-Ser-Asp-Val-Ser- $Xaa_{18}$-Tyr-Leu-Glu-$Xaa_{22}$-$Xaa_{23}$-Ala-Ala-$Xaa_{26}$-Glu- Phe-Ile-$Xaa_{30}$-Trp-Leu-Val-$Xaa_{34}$-$Xaa_{35}$-$Xaa_{36}$-$Xaa_{37}$-

$Xaa_{38}$ wherein

Xaa$_7$ is L-histidine, D-histidine, desamino-histidine, 2-amino-histidine, β-hydroxy-histidine, homohistidine, N$^α$-acetyl-histidine, α-fluoromethyl-histidine, α-methyl-histidine, 3-pyridylalanine, 2-pyridylalanine or 4-pyridylalanine;

Xaa$_8$ is Ala, D-Ala, Gly, Val, Leu, Ile, Lys, Aib, (1-aminocyclopropyl)carboxylic acid, (1-aminocyclobutyl)carboxylic acid, (1-aminocyclopentyl)carboxylic acid, (1-aminocyclohexyl)carboxylic acid, (1-aminocycloheptyl) carboxylic acid, or (1-aminocyclooctyl)carboxylic acid;

Xaa$_{18}$ is Ser, Lys or Arg;

Xaa$_{22}$ is Gly, Glu or Aib;

Xaa$_{23}$ is Gln, Glu, Lys or Arg;

Xaa$_{26}$ is Lys, Glu or Arg;

Xaa$_{30}$ is Ala, Glu or Arg;

Xaa$_{34}$ is Lys, Glu or Arg;

Xaa$_{35}$ is Gly or Aib;

Xaa$_{36}$ is Arg or Lys;

Xaa$_{37}$ is Gly, Ala, Glu or Lys;

Xaa$_{38}$ is Lys, NH$_2$ or is absent.

In another embodiment of the invention the insulinotropic agent is selected from GLP-1(7-35), GLP-1(7-36), GLP-1(7-36)-amide, GLP-1(7-37), GLP-1(7-38), GLP-1(7-39), GLP-1(7-40), GLP-1(7-41) or an analogue thereof.

In another embodiment of the invention the insulinotropic agent comprises no more than fifteen amino acid residues which have been exchanged, added or deleted as compared to GLP-1(7-37) (SEQ ID No. 1), or no more than ten amino acid residues which have been exchanged, added or deleted as compared to GLP-1(7-37) (SEQ ID No. 1).

In another embodiment of the invention the insulinotropic agent comprises no more than six amino acid residues which have been exchanged, added or deleted as compared to GLP-1(7-37) (SEQ ID No. 1).

In another embodiment of the invention the insulinotropic agent comprises no more than 4 amino acid residues which are not encoded by the genetic code.

In another embodiment of the invention the insulinotropic agent comprises an Aib residue as the second amino acid residue from the N-terminal.

In another embodiment of the invention the N-terminal amino acid residue (position 7 in formulae II and III) of said insulinotropic agent is selected from the group consisting of D-histidine, desamino-histidine, 2-amino-histidine, β-hydroxy-histidine, homohistidine, N$^α$-acetyl-histidine, α-fluoromethyl-histidine, α-methyl-histidine, 3-pyridylalanine, 2-pyridylalanine and 4-pyridylalanine.

In another embodiment of the invention the insulinotropic agent is selected from the group consisting of [Arg$^{34}$]GLP-1(7-37), [Arg$^{26,34}$]GLP-1(7-37)Lys, [Lys$^{36}$Arg$^{26,34}$]GLP-1(7-36), [Aib$^{8,22,35}$]GLP-1(7-37), [Aib$^{8,35}$]GLP-1(7-37), [Aib$^{8,22}$]GLP-1(7-37), [Aib$^{8,22,35}$Arg$^{26,34}$]GLP-1(7-37)Lys, [Aib$^{8,35}$Arg$^{26,34}$]GLP-1(7-37)Lys, [Aib$^{8,22}$Arg$^{26,34}$]GLP-1(7-37)Lys, [Aib$^{8,22,35}$Arg$^{26,34}$]GLP-1(7-37)Lys, [Aib$^{8,35}$Arg$^{26,34}$]GLP-1(7-37)Lys, [Aib$^{8,22,35}$Arg$^{26}$]GLP-1(7-37)Lys, [Aib$^{8,35}$Arg$^{26}$]GLP-1(7-37)Lys, [Aib$^{8,22}$Arg$^{26}$]GLP-1(7-37)Lys, [Aib$^{8,22,35}$Arg$^{34}$]GLP-1(7-37)Lys, [Aib$^{8,35}$Arg$^{34}$]GLP-1(7-37)Lys, [Aib$^{8,22}$Arg$^{34}$]GLP-1(7-37)Lys, [Aib$^{8,22,35}$Ala$^{37}$]GLP-1(7-37)Lys, [Aib$^{8,35}$Ala$^{37}$]GLP-1(7-37)Lys, [Aib$^{8,22}$Ala$^{37}$]GLP-1(7-37)Lys, [Aib$^{8,22,35}$ Lys$^{37}$]GLP-1(7-37), [Aib$^{8,35}$Lys$^{37}$]GLP-1(7-37), [Aib$^{8,22}$Lys$^{37}$]GLP-1(7-37) or derivatives thereof which has been amidated on the C-terminal.

In another embodiment of the invention the insulinotropic agent comprises at least one Aib residue.

In another embodiment of the invention the insulinotropic agent contains two Aib residues.

In another embodiment of the invention the insulinotropic agent comprises a serine residue at position 18 relative to GLP-1(7-37) (SEQ ID. No. 1), corresponding to position 12 relative to Exendin-4(1-39).

In another embodiment of the invention the insulinotropic agent comprises a tyrosine residue at position 19 relative to GLP-1(7-37) (SEQ ID. No. 1), corresponding to position 13 relative to Exendin-4(1-39).

In another embodiment of the invention the insulinotropic agent comprises a glycine residue at position 22 relative to GLP-1(7-37) (SEQ ID. No. 1), corresponding to position 16 relative to Exendin-4(1-39).

In another embodiment of the invention the insulinotropic agent comprises a glutamine residue at position 23 relative to GLP-1(7-37) (SEQ ID. No. 1), corresponding to position 17 relative to Exendin-4(1-39).

In another embodiment of the invention the insulinotropic agent comprises a lysine residue at position 26 relative to GLP-1(7-37) (SEQ ID. No. 1), corresponding to position 20 relative to Exendin-4(1-39).

In another embodiment of the invention the insulinotropic agent comprises a glutamate residue at position 27 relative to GLP-1(7-37) (SEQ ID. No. 1), corresponding to position 21 relative to Exendin-4(1-39).

In another embodiment of the invention the insulinotropic agent is exendin-4(1-39).

In another embodiment of the invention the insulinotropic agent is ZP-10, i.e. [Ser$^{38}$Lys$^{39}$]Exendin-4(1-39)LysLysLysLysLys-amide (SEQ ID No. 5).

In another embodiment of the invention the insulinotropic agent is attached to Y—C*-Q or Q via the amino acid residue in position 25 to 45 relative to the amino acid sequence SEQ ID No 1.

In another embodiment of the invention the insulinotropic agent is attached to Y—C*-Q or Q via an amino acid residue selected from one of the 10 C-terminal amino acid residues.

In another embodiment of the invention the insulinotropic agent is attached to Y—C*-Q or Q via the amino acid residue in position 23, 26, 34, 36 or 38 relative to the amino acid sequence SEQ ID No:1.

In another embodiment of the invention the insulinotropic agent is attached to Y—C*-Q or Q via the amino acid residue in position 17, 20, 28, 30 or 32 relative to the amino acid sequence SEQ ID No:2.

In another embodiment of the invention the insulinotropic agent is attached to Y—C*-Q or Q via the C-terminal amino acid residue.

In another embodiment of the invention the insulinotropic agent is attached to Y—C*-Q or Q via a carboxyl group, an amino group, a keto group, a hydroxyl group, a thiol group or a hydrazide group.

In another embodiment of the invention the insulinotropic agent is attached to Y—C*-Q or Q via a the epsilon-amino group on a lysine residue.

In another embodiment of the invention the insulinotropic agent comprises only one lysine residue.

In another embodiment of the invention the insulinotropic agent comprises only one lysine residue which is the C-terminal amino acid residue of said insulinotropic agent.

In another embodiment the compound according to the present invention has an EC$_{50}$ of less than 1000 pM, less than 500 pM, less than 300 pM, less than 200 pM, less than 100 pM, less than 50 pM or less than 10 pM as determined by the functional receptor assay disclosed herein.

In another embodiment the compound according to the present invention is selected from the group consisting of $N^{\epsilon 37}$-((2S)-2,6-di-(mPEGylcarbonylamino)hexanoyl) [Aib$^{8,22,35}$,Lys$^{37}$]GLP-1(7-37) wherein mPEGyl is polydisperse and has a molecular weight of approximately 20 kDa, $N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 20 kDa, $N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 5 kDa, $N^{\epsilon 37}$-(3-(mPEGyl)propionyl)[Aib$^{8,22,35}$,Lys$^{37}$]GLP-1(7-37) amide wherein mPEGyl is polydisperse and has a molecular weight of approximately 2 kDa, $N^{\epsilon 26}$-(3-(mPEGyl)propionyl)[Aib$^{8}$,Glu$^{22,30}$,Lys$^{33}$,Asn$^{34}$,Gly$^{35,36}$,Pro$^{37}$]GLP-1(7-37)ylSerSerGlyAlaProProSer amide wherein mPEGyl is polydisperse and has a molecular weight of approximately 2 kDa, $N^{\alpha}$-[Aib$^{8,22,35}$]GLP-1-(7-37)yl(N$^{\epsilon}$-(3-(mPEGyl)propionyl) Lysinamide) wherein mPEGyl is polydisperse and has a molecular weight of approximately 750 Da, $N^{\epsilon}$-[Aib$^{8,22,35}$]GLP-1(7-37)yl(N$^{\epsilon}$-(1-mPEGylpropyl-2,5-dioxo-pyrrolidin-3-yl)Cysteinamide wherein mPEGyl is polydisperse and has a molecular weight of approximately 5000 Da, $N^{\alpha}$-(3-(3H-imidazol-4-yl)-propionyl [Aib$^{22,35}$,Arg$^{26,34}$] GLP-1-(8-37))yl(N$^{\epsilon}$-(3-(mPEGyl)propionyl)Lysinamide) wherein mPEGyl is polydisperse and has a molecular weight of approximately 2000 Da, $N^{\epsilon 26}$-(3-(mPEGyl)propionyl)[Arg$^{34}$]GLP-1-(7-37) wherein mPGyl is polydisperse and has a molecular weight of approximately 2 kDa, and (S)—N—((S)-5-(N—((S)-5-carbamoyl-5-(mPEGylpropionylamino)pentyl)carbamoyl)-5-(mPEGylpropionylamino)pentyl)-5-(N$^{\alpha 7}$-(3-(4-imidazolyl)propionyl) [Aib$^{22,35}$,Arg$^{26,34}$]GLP-1-(8-37)yl)-2-(mPEGylpropionylamino)hexanoic amide wherein mPEGyl is polydisperse and has a molecular weight of approximately 750 Da, In another embodiment the compound according to the present invention is selected from the group consisting of $N^{\epsilon 37}$-((2S)-2,6-di-(mPEGylcarbonylamino)hexanoyl) [Aib$^{8,22,35}$,Lys$^{37}$]GLP-1(7-37) wherein mPEGyl is polydisperse and has a molecular weight of approximately 2 kDa, $N^{\epsilon 37}$-((2S)-2,6-di-(mPEGylcarbonylamino)hexanoyl) [Aib$^{8,22,35}$,Lys$^{37}$]GLP-1(7-37) wherein mPEGyl is polydisperse and has a molecular weight of approximately 5 kDa, $N^{\epsilon 37}$-((2S)-2,6-di-(mPEGylcarbonylamino)hexanoyl) [Aib$^{8,22,35}$,Lys$^{37}$]GLP-1(7-37) wherein mPEGyl is polydisperse and has a molecular weight of approximately 20 kDa, $N^{\epsilon 37}$-((2S)-2,6-di-(mPEGylcarbonylamino)hexanoyl) [Aib$^{8,22,35}$,Lys$^{37}$]GLP-1(7-37) wherein mPEGyl is polydisperse and has a molecular weight of approximately 40 kDa, $N^{\epsilon 37}$-((2S)-2,6-di-(mPEGylcarbonylamino)hexanoyl) [Aib$^{8,22,35}$,Lys$^{37}$]GLP-1(7-37) amide wherein mPEGyl is polydisperse and has a molecular weight of approximately 2 kDa, $N^{\epsilon 37}$-((2S)-2,6-di-(mPEGylcarbonylamino)hexanoyl) [Aib$^{8,22,35}$,Lys$^{37}$]GLP-1(7-37) amide wherein mPEGyl is polydisperse and has a molecular weight of approximately 5 kDa, $N^{\epsilon 37}$-((2S)-2,6-di-(mPEGylcarbonylamino)hexanoyl) [Aib$^{8,22,35}$,Lys$^{37}$]GLP-1(7-37) amide wherein mPEGyl is polydisperse and has a molecular weight of approximately 20 kDa, $N^{\epsilon 37}$-((2S)-2,6-di-(mPEGylcarbonylamino)hexanoyl) [Aib$^{8,22,35}$,Lys$^{37}$]GLP-1(7-37) amide wherein mPEGyl is polydisperse and has a molecular weight of approximately 40 kDa, $N^{\epsilon 37}$-((2S)-2,6-di-(mPEGylcarbonylamino)hexanoyl) [Aib$^{8,22,35}$,Lys$^{37}$]GLP-1(7-37)Lys wherein mPEGyl is polydisperse and has a molecular weight of approximately 2 kDa, $N^{\epsilon 37}$-((2S)-2,6-di-(mPEGylcarbonylamino)hexanoyl) [Aib$^{8,22,35}$,Lys$^{37}$]GLP-1(7-37)Lys wherein mPEGyl is polydisperse and has a molecular weight of approximately 5 kDa, $N^{\epsilon 37}$-((2S)-2,6-di-(mPEGylcarbonylamino)hexanoyl) [Aib$^{8,22,35}$,Lys$^{37}$]GLP-1(7-37)Lys wherein mPEGyl is polydisperse and has a molecular weight of approximately 20 kDa, $N^{\epsilon 37}$-((2S)-2,6-di-(mPEGylcarbonylamino)hexanoyl) [Aib$^{8,22,35}$,Lys$^{37}$]GLP-1(7-37)Lys wherein mPEGyl is polydisperse and has a molecular weight of approximately 40 kDa, $N^{\epsilon 37}$-((2S)-2,6-di-(mPEGylcarbonylamino)hexanoyl) [Aib$^{8,22,35}$,Lys$^{37}$]GLP-1(7-37)Lys amide wherein mPEGyl is polydisperse and has a molecular weight of approximately 2 kDa, $N^{\epsilon 37}$-((2S)-2,6-di-(mPEGylcarbonylamino)hexanoyl) [Aib$^{8,22,35}$,Lys$^{37}$]GLP-1(7-37)Lys amide wherein mPEGyl is polydisperse and has a molecular weight of approximately 5 kDa, $N^{\epsilon 37}$-((2S)-2,6-di-(mPEGylcarbonylamino)hexanoyl) [Aib$^{8,22,35}$,Lys$^{37}$]GLP-1(7-37)Lys amide wherein mPEGyl is polydisperse and has a molecular weight of approximately 20 kDa, $N^{\epsilon 37}$-((2S)-2,6-di-(mPEGylcarbonylamino)hexanoyl) [Aib$^{8,22,35}$,Lys$^{37}$]GLP-1(7-37)Lys amide wherein mPEGyl is polydisperse and has a molecular weight of approximately 40 kDa, $N^{\epsilon 37}$-((2S)-2,6-di-(mPEGylcarbonylamino)hexanoyl) [Aib$^{8,22}$,Lys$^{37}$]GLP-1(7-37) wherein mPEGyl is polydisperse and has a molecular weight of approximately 2 kDa, $N^{\epsilon 37}$-((2S)-2,6-di-(mPEGylcarbonylamino)hexanoyl) [Aib$^{8,22}$,Lys$^{37}$]GLP-1(7-37) wherein mPEGyl is polydisperse and has a molecular weight of approximately 5 kDa, $N^{\epsilon 37}$-((2S)-2,6-di-(mPEGylcarbonylamino)hexanoyl) [Aib$^{8,22}$,Lys$^{37}$]GLP-1(7-37) wherein mPEGyl is polydisperse and has a molecular weight of approximately 20 kDa, $N^{\epsilon 37}$-((2S)-2,6-di-(mPEGylcarbonylamino)hexanoyl) [Aib$^{8,22}$,Lys$^{37}$]GLP-1(7-37) wherein mPEGyl is polydisperse and has a molecular weight of approximately 40 kDa, $N^{\epsilon 37}$-((2S)-2,6-di-(mPEGylcarbonylamino)hexanoyl) [Aib$^{8,22}$,Lys$^{37}$]GLP-1(7-37) amide wherein mPEGyl is polydisperse and has a molecular weight of approximately 2 kDa, $N^{\epsilon 37}$-((2S)-2,6-di-(mPEGylcarbonylamino)hexanoyl) [Aib$^{8,22}$,Lys$^{37}$]GLP-1(7-37) amide wherein mPEGyl is polydisperse and has a molecular weight of approximately 5 kDa, $N^{\epsilon 37}$-((2S)-2,6-di-(mPEGylcarbonylamino)hexanoyl) [Aib$^{8,22}$,Lys$^{37}$]GLP-1(7-37) amide wherein mPEGyl is polydisperse and has a molecular weight of approximately 20 kDa, $N^{\epsilon 37}$-((2S)-2,6-di-(mPEGylcarbonylamino)hexanoyl)[Aib$^{8,22}$,Lys$^{37}$]GLP-1(7-37) amide wherein mPEGyl is polydisperse and has a molecular weight of approximately 40 kDa, $N^{\epsilon 37}$-((2S)-2,6-di-(mPEGylcarbonylamino)hexanoyl)[Aib$^{8,22}$,Lys$^{37}$]GLP-1(7-37)Lys wherein mPEGyl is polydisperse and has a molecular weight of approximately 2 kDa, $N^{\epsilon 37}$-((2S)-2,6-di-(mPEGylcarbonylamino)hexanoyl)[Aib$^{8,22}$,Lys$^{37}$]GLP-1(7-37)Lys wherein mPEGyl is polydisperse and has a molecular weight of approximately 5 kDa, $N^{\epsilon 37}$-((2S)-2,6-di-(mPEGylcarbonylamino)hexanoyl)[Aib$^{8,22}$,Lys$^{37}$]GLP-1(7-37)Lys wherein mPEGyl is polydisperse and has a molecular weight of approximately 20 kDa, $N^{\epsilon 37}$-((2S)-2,6-di-(mPEGylcarbonylamino)hexanoyl)[Aib$^{8,22}$,Lys$^{37}$]GLP-1(7-37)Lys wherein mPEGyl is polydisperse and has a molecular weight of approximately 40 kDa, $N^{\epsilon 37}$-((2S)-2,6-di-(mPEGylcarbonylamino)hexanoyl)[Aib$^{8,22}$,Lys$^{37}$]GLP-1(7-37)Lys amide wherein mPEGyl is polydisperse and has a molecular weight of approximately 2 kDa, $N^{\epsilon 37}$-((2S)-2,6-di-(mPEGylcarbonylamino)hexanoyl)[Aib$^{8,22}$,Lys$^{37}$]GLP-1(7-37)Lys amide wherein mPEGyl is polydisperse and has a molecular weight of approximately 5 kDa, $N^{\epsilon 37}$-((2S)-2,6-di-(mPEGylcarbonylamino)hexanoyl)[Aib$^{8,22}$,Lys$^{37}$]GLP-1(7-37)Lys amide wherein mPEGyl is polydisperse and has a molecular weight of approximately 20 kDa, $N^{\epsilon 37}$-((2S)-2,6-di-(mPEGylcarbonylamino)hexanoyl)[Aib$^{8,22}$,Lys$^{37}$]GLP-1(7-37)Lys amide wherein mPEGyl is polydisperse and has a molecular weight of approximately 40 kDa, $N^{\epsilon 37}$-((2S)-2,6-di-(mPEGylcarbonylamino)hexanoyl)[Aib$^{8,35}$,Lys$^{37}$]GLP-1(7-37) wherein mPEGyl is polydisperse and has a molecular weight of approximately 2 kDa, $N^{\epsilon 37}$-((2S)-2,6-di-(mPEGylcarbonylamino)hexanoyl)[Aib$^{8,35}$,Lys$^{37}$]GLP-1(7-37) wherein mPEGyl is polydisperse and has a molecular weight of approximately 5 kDa, $N^{\epsilon 37}$-((2S)-2,6-di-(mPEGylcarbonylamino)hexanoyl)[Aib$^{8,35}$,Lys$^{37}$]GLP-1(7-37) wherein mPEGyl is polydisperse and has a molecular weight of approximately 20 kDa, $N^{\epsilon 37}$-((2S)-2,6-di-(mPEGylcarbonylamino)hexanoyl)[Aib$^{8,35}$,Lys$^{37}$]GLP-1(7-37) wherein mPEGyl is polydisperse and has a molecular weight of approximately 40 kDa, $N^{\epsilon 37}$-((2S)-2,6-di-(mPEGylcarbonylamino)hexanoyl)[Aib$^{8,35}$,Lys$^{37}$]GLP-1(7-37) amide wherein mPEGyl is polydisperse and has a molecular weight of approximately 2 kDa, $N^{\epsilon 37}$-((2S)-2,6-di-(mPEGylcarbonylamino)hexanoyl)[Aib$^{8,35}$,Lys$^{37}$]GLP-1(7-37) amide wherein mPEGyl is polydisperse and has a molecular weight of approximately 5 kDa, $N^{\epsilon 37}$-((2S)-2,6-di-(mPEGylcarbonylamino)hexanoyl)[Aib$^{8,35}$,Lys$^{37}$]GLP-1(7-37) amide wherein mPEGyl is polydisperse and has a molecular weight of approximately 20 kDa, $N^{\epsilon 37}$-((2S)-2,6-di-(mPEGylcarbonylamino)hexanoyl)[Aib$^{8,35}$,Lys$^{37}$]GLP-1(7-37) amide wherein mPEGyl is polydisperse and has a molecular weight of approximately 40 kDa, $N^{\epsilon 37}$-((2S)-2,6-di-(mPEGylcarbonylamino)hexanoyl)[Aib$^{8,35}$,Lys$^{37}$]GLP-1(7-37)Lys wherein mPEGyl is polydisperse and has a molecular weight of approximately 2 kDa, $N^{\epsilon 37}$-((2S)-2,6-di-(mPEGylcarbonylamino)hexanoyl)[Aib$^{8,35}$,Lys$^{37}$]GLP-1(7-37)Lys wherein mPEGyl is polydisperse and has a molecular weight of approximately 5 kDa, $N^{\epsilon 37}$-((2S)-2,6-di-(mPEGylcarbonylamino)hexanoyl)[Aib$^{8,35}$,Lys$^{37}$]GLP-1(7-37)Lys wherein mPEGyl is polydisperse and has a molecular weight of approximately 20 kDa, $N^{\epsilon 37}$-((2S)-2,6-di-(mPEGylcarbonylamino)hexanoyl)[Aib$^{8,35}$,Lys$^{37}$]GLP-1(7-37)Lys wherein mPEGyl is polydisperse and has a molecular weight of approximately 40 kDa, $N^{\epsilon 37}$-((2S)-2,6-di-(mPEGylcarbonylamino)hexanoyl)[Aib$^{8,35}$,Lys$^{37}$]GLP-1(7-37)Lys amide wherein mPEGyl is polydisperse and has a molecular weight of approximately 2 kDa, $N^{\epsilon 37}$-((2S)-2,6-di-(mPEGylcarbonylamino)hexanoyl)[Aib$^{8,35}$,Lys$^{37}$]GLP-1(7-37)Lys amide wherein mPEGyl is polydisperse and has a molecular weight of approximately 5 kDa, $N^{\epsilon 37}$-((2S)-2,6-di-(mPEGylcarbonylamino)hexanoyl)[Aib$^{8,35}$,Lys$^{37}$]GLP-1(7-37)Lys amide wherein mPEGyl is polydisperse and has a molecular weight of approximately 20 kDa, $N^{\epsilon 37}$-((2S)-2,6-di-(mPEGylcarbonylamino)hexanoyl)[Aib$^{8,35}$,Lys$^{37}$]GLP-1(7-37)Lys amide wherein mPEGyl is polydisperse and has a molecular weight of approximately 40 kDa, $N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 2 kDa, $N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 5 kDa, $N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 10 kDa, $N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 20 kDa, $N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 40 kDa, $N^{\epsilon 37}$-(3-(mPEGyl)propionyl)[Aib$^{8,22,35}$,Lys$^{37}$]GLP-1(7-37) amide wherein mPEGyl is polydisperse and has a molecular weight of approximately 2 kDa, $N^{\epsilon 37}$-(3-(mPEGyl)propionyl)[Aib$^{8,22,35}$,Lys$^{37}$]GLP-1(7-37) amide wherein mPEGyl is polydisperse and has a molecular weight of approximately 5 kDa, $N^{\epsilon 37}$-(3-(mPEGyl)propionyl)[Aib$^{8,22,35}$,Lys$^{37}$]GLP-1(7-37) amide wherein mPEGyl is polydisperse and has a molecular weight of approximately 10 kDa, $N^{\epsilon 37}$-(3-(mPEGyl)propionyl)[Aib$^{8,22,35}$,Lys$^{37}$]GLP-1(7-37) amide wherein mPEGyl is polydisperse and has a molecular weight of approximately 20 kDa, $N^{\epsilon 37}$-(3-(mPEGyl)propionyl)[Aib$^{8,22,35}$,Lys$^{37}$]GLP-1(7-37) amide wherein mPEGyl is polydisperse and has a molecular weight of approximately 40 kDa, $N^{\epsilon 37}$-(3-(mPEGyl)propionyl)[Aib$^{8,22,35}$,Lys$^{37}$]GLP-1(7-37)Lys wherein mPEGyl is polydisperse and has a molecular weight of approximately 2 kDa, $N^{\epsilon 37}$-(3-(mPEGyl)propionyl)[Aib$^{8,22,35}$,Lys$^{37}$]GLP-1(7-37) Lys wherein mPEGyl is polydisperse and has a molecular weight of approximately 5 kDa, $N^{\epsilon 37}$-(3-(mPEGyl)propionyl)[Aib$^{8,22,35}$,Lys$^{37}$]GLP-1(7-37) Lys wherein mPEGyl is polydisperse and has a molecular weight of approximately 10 kDa, $N^{\epsilon 37}$-(3-(mPEGyl)propionyl)[Aib$^{8,22,35}$,Lys$^{37}$]GLP-1(7-37) Lys wherein mPEGyl is polydisperse and has a molecular weight of approximately 20 kDa, $N^{\epsilon 37}$-(3-(mPEGyl)propionyl)[Aib$^{8,22,35}$,Lys$^{37}$]GLP-1(7-37) Lys wherein mPEGyl is polydisperse and has a molecular weight of approximately 40 kDa, $N^{\epsilon 37}$-(3-(mPEGyl)propionyl)[Aib$^{8,22,35}$,Lys$^{37}$]GLP-1(7-37) Lys amide wherein mPEGyl is polydisperse and has a molecular weight of approximately 2 kDa, $N^{\epsilon 37}$-(3-(mPEGyl)propionyl)[Aib$^{8,22,35}$,Lys$^{37}$]GLP-1(7-37) Lys amide wherein mPEGyl is polydisperse and has a molecular weight of approximately 5 kDa, $N^{\epsilon 37}$-(3-(mPEGyl)propionyl)[Aib$^{8,22,35}$,Lys$^{37}$]GLP-1(7-37) Lys amide wherein mPEGyl is polydisperse and has a molecular weight of approximately 10 kDa, $N^{\epsilon 37}$-(3-(mPEGyl)propionyl)[Aib$^{8,22,35}$,Lys$^{37}$]GLP-1(7-37) Lys amide wherein mPEGyl is polydisperse and has a molecular weight of approximately 20 kDa, $N^{\epsilon 37}$-(3-(mPEGyl)propionyl)[Aib$^{8,22,35}$,Lys$^{37}$]GLP-1(7-37) Lys amide wherein mPEGyl is polydisperse and has a molecular weight of approximately 40 kDa, $N^{\epsilon 37}$-(3-(mPEGyl)propionyl)[Aib$^{8,22}$,Lys$^{37}$]GLP-1(7-37) wherein mPEGyl is polydisperse and has a molecular weight of approximately 2 kDa, $N^{\epsilon 37}$-(3-(mPEGyl)propionyl)[Aib$^{8,22}$,Lys$^{37}$]GLP-1(7-37) wherein mPEGyl is polydisperse and has a molecular weight of approximately 5 kDa, $N^{\epsilon 37}$-(3-(mPEGyl)propionyl)[Aib$^{8,22}$,Lys$^{37}$]GLP-1(7-37) wherein mPEGyl is polydisperse and has a molecular weight of approximately 10 kDa, $N^{\epsilon 37}$-(3-(mPEGyl)propionyl)[Aib$^{8,22}$,Lys$^{37}$]GLP-1(7-37) wherein mPEGyl is polydisperse and has a molecular weight of approximately 20 kDa, $N^{\epsilon 37}$-(3-(mPEGyl)propionyl)[Aib$^{8,22}$,Lys$^{37}$]GLP-1(7-37) wherein mPEGyl is polydisperse and has a molecular weight of approximately 40 kDa, $N^{\epsilon 37}$-(3-(mPEGyl)propionyl)[Aib$^{8,22}$,Lys$^{37}$]GLP-1(7-37) amide wherein mPEGyl is polydisperse and has a molecular weight of approximately 2 kDa, $N^{\epsilon 37}$-(3-(mPEGyl)propionyl)[Aib$^{8,22}$,Lys$^{37}$]GLP-1(7-37) amide wherein mPEGyl is polydisperse and has a molecular weight of approximately 5 kDa, $N^{\epsilon 37}$-(3-(mPEGyl)propionyl)[Aib$^{8,22}$,Lys$^{37}$]GLP-1(7-37) amide wherein mPEGyl is polydisperse and has a molecular weight of approximately 10 kDa, $N^{\epsilon 37}$-(3-(mPEGyl)propionyl)[Aib$^{8,22}$,Lys$^{37}$]GLP-1(7-37) amide wherein mPEGyl is polydisperse and has a molecular weight of approximately 20 kDa, $N^{\epsilon 37}$-(3-(mPEGyl)propionyl)[Aib$^{8,22}$,Lys$^{37}$]GLP-1(7-37) amide wherein mPEGyl is polydisperse and has a molecular weight of approximately 40 kDa, $N^{\epsilon 37}$-(3-(mPEGyl)propionyl)[Aib$^{8,22}$,Lys$^{37}$]GLP-1(7-37) Lys wherein mPEGyl is polydisperse and has a molecular weight of approximately 2 kDa, $N^{\epsilon 37}$-(3-(mPEGyl)propionyl)[Aib$^{8,22}$,Lys$^{37}$]GLP-1(7-37) Lys wherein mPEGyl is polydisperse and has a molecular weight of approximately 5 kDa, $N^{\epsilon 37}$-(3-(mPEGyl)propionyl)[Aib$^{8,22}$,Lys$^{37}$]GLP-1(7-37) Lys wherein mPEGyl is polydisperse and has a molecular weight of approximately 10 kDa, $N^{\epsilon 37}$-(3-(mPEGyl)propionyl)[Aib$^{8,22}$,Lys$^{37}$]GLP-1(7-37) Lys wherein mPEGyl is polydisperse and has a molecular weight of approximately 20 kDa, $N^{\epsilon 37}$-(3-(mPEGyl)propionyl)[Aib$^{8,22}$,Lys$^{37}$]GLP-1(7-37) Lys wherein mPEGyl is polydisperse and has a molecular weight of approximately 40 kDa, $N^{\epsilon 37}$-(3-(mPEGyl)propionyl)[Aib$^{8,22}$,Lys$^{37}$]GLP-1(7-37) Lys amide wherein mPEGyl is polydisperse and has a molecular weight of approximately 2 kDa, $N^{\epsilon 37}$-(3-(mPEGyl)propionyl)[Aib$^{8,22}$,Lys$^{37}$]GLP-1(7-37) Lys amide wherein mPEGyl is polydisperse and has a molecular weight of approximately 5 kDa, $N^{\epsilon 37}$-(3-(mPEGyl)propionyl)[Aib$^{8,22}$,Lys$^{37}$]GLP-1(7-37) Lys amide wherein mPEGyl is polydisperse and has a molecular weight of approximately 10 kDa, $N^{\epsilon 37}$-(3-(mPEGyl)propionyl)[Aib$^{8,22}$,Lys$^{37}$]GLP-1(7-37) Lys amide wherein mPEGyl is polydisperse and has a molecular weight of approximately 20 kDa, $N^{\epsilon 37}$-(3-(mPEGyl)propionyl)[Aib$^{8,22}$,Lys$^{37}$]GLP-1(7-37) Lys amide wherein mPEGyl is polydisperse and has a molecular weight of approximately 40 kDa, $N^{\epsilon 37}$-(3-(mPEGyl)propionyl)[Aib$^{8,35}$,Lys$^{37}$]GLP-1(7-37) wherein mPEGyl is polydisperse and has a molecular weight of approximately 2 kDa, $N^{\epsilon 37}$-(3-(mPEGyl)propionyl)[Aib$^{8,35}$,Lys$^{37}$]GLP-1(7-37) wherein mPEGyl is polydisperse and has a molecular weight of approximately 5 kDa, $N^{\epsilon 37}$-(3-(mPEGyl)propionyl)[Aib$^{8,35}$,Lys$^{37}$]GLP-1(7-37) wherein mPEGyl is polydisperse and has a molecular weight of approximately 10 kDa, $N^{\epsilon 37}$-(3-(mPEGyl)propionyl)[Aib$^{8,35}$,Lys$^{37}$]GLP-1(7-37) wherein mPEGyl is polydisperse and has a molecular weight of approximately 20 kDa, $N^{\epsilon 37}$-(3-(mPEGyl)propionyl)[Aib$^{8,35}$,Lys$^{37}$]GLP-1(7-37) wherein mPEGyl is polydisperse and has a molecular weight of approximately 40 kDa, $N^{\epsilon 37}$-(3-(mPEGyl)propionyl)[Aib$^{8,35}$,Lys$^{37}$]GLP-1(7-37) amide wherein mPEGyl is polydisperse and has a molecular weight of approximately 2 kDa, $N^{\epsilon 37}$-(3-(mPEGyl)propionyl)[Aib$^{8,35}$,Lys$^{37}$]GLP-1(7-37) amide wherein mPEGyl is polydisperse and has a molecular weight of approximately 5 kDa, $N^{\epsilon 37}$-(3-(mPEGyl)propionyl)[Aib$^{8,35}$,Lys$^{37}$]GLP-1(7-37) amide wherein mPEGyl is polydisperse and has a molecular weight of approximately 10 kDa, $N^{\epsilon 37}$-(3-(mPEGyl)propionyl)[Aib$^{8,35}$,Lys$^{37}$]GLP-1(7-37) amide wherein mPEGyl is polydisperse and has a molecular weight of approximately 20 kDa, $N^{\epsilon 37}$-(3-(mPEGyl)propionyl)[Aib$^{8,35}$,Lys$^{37}$]GLP-1(7-37) amide wherein mPEGyl is polydisperse and has a molecular weight of approximately 40 kDa, $N^{\epsilon 37}$-(3-(mPEGyl)propionyl)[Aib$^{8,35}$,Lys$^{37}$]GLP-1(7-37) Lys wherein mPEGyl is polydisperse and has a molecular weight of approximately 2 kDa, $N^{\epsilon 37}$-(3-(mPEGyl)propionyl)[Aib$^{8,35}$,Lys$^{37}$]GLP-1-(7-37) Lys wherein mPEGyl is polydisperse and has a molecular weight of approximately 5 kDa, $N^{\epsilon 37}$-(3-(mPEGyl)propionyl)[Aib$^{8,35}$,Lys$^{37}$]GLP-1(7-37) Lys wherein mPEGyl is polydisperse and has a molecular weight of approximately 10 kDa, $N^{\epsilon 37}$-(3-(mPEGyl)propionyl)[Aib$^{8,35}$,Lys$^{37}$]GLP-1(7-37) Lys wherein mPEGyl is polydisperse and has a molecular weight of approximately 20 kDa, $N^{\epsilon 37}$-(3-(mPEGyl)propionyl)[Aib$^{8,35}$,Lys$^{37}$]GLP-1(7-37) Lys wherein mPEGyl is polydisperse and has a molecular weight of approximately 40 kDa, $N^{\epsilon37}$-(3-(mPEGyl)propionyl)[Aib$^{8,35}$,Lys$^{37}$]GLP-1(7-37) Lys amide wherein mPEGyl is polydisperse and has a molecular weight of approximately 2 kDa, $N^{\epsilon37}$-(3-(mPEGyl)propionyl)[Aib$^{8,35}$,Lys$^{37}$]GLP-1(7-37) Lys amide wherein mPEGyl is polydisperse and has a molecular weight of approximately 5 kDa, $N^{\epsilon37}$-(3-(mPEGyl)propionyl)[Aib$^{8,35}$,Lys$^{37}$]GLP-1(7-37) Lys amide wherein mPEGyl is polydisperse and has a molecular weight of approximately 10 kDa, $N^{\epsilon37}$-(3-(mPEGyl)propionyl)[Aib$^{8,35}$,Lys$^{37}$]GLP-1(7-37) Lys amide wherein mPEGyl is polydisperse and has a molecular weight of approximately 20 kDa, and $N^{\epsilon37}$-(3-(mPEGyl)propionyl)[Aib$^{8,35}$,Lys$^{37}$]GLP-1(7-37) Lys amide wherein mPEGyl is polydisperse and has a molecular weight of approximately 40 kDa.

In another embodiment the compound according to the present invention is selected from the group consisting of $N^{\epsilon37}$-(3-(mPEGyl)propionyl)[Lys$^{37}$]GLP-1-(7-37) where mPEGyl is polydisperse and is polydisperse and has a Mw of approx 750 Da, $N^{\epsilon37}$-(3-(mPEGyl)propionyl)[Lys$^{37}$]GLP-1-(7-37) amide where mPEGyl is polydisperse and has a Mw of approx 750 Da, GLP-1-(7-37)yl(N$^\epsilon$-(3-(mPEGyl)propionyl))Lysine where mPEGyl is polydisperse and has a Mw of approx 750 Da, GLP-1-(7-37)yl(N$^\epsilon$-(3-(mPEGyl)propionyl))Lysinamide where mPEGyl is polydisperse and has a Mw of approx 750 Da, $N^{\epsilon37}$-(3-(mPEGyl)propionyl)[Aib$^{35}$,Lys$^{37}$]GLP-1-(7-37) where mPEGyl is polydisperse and has a Mw of approx 750 Da, $N^{\epsilon37}$-(3-(mPEGyl)propionyl)[Aib$^{35}$,Lys$^{37}$]GLP-1-(7-37) amide where mPEGyl is polydisperse and has a Mw of approx 750 Da, $N^\alpha$-[Aib$^{35}$]GLP-1-(7-37)yl(N$^\epsilon$-(3-(mPEGyl)propionyl))Lysine where mPEGyl is polydisperse and has a Mw of approx 750 Da, $N^\alpha$-[Aib$^{35}$]GLP-1-(7-37)yl(N$^\epsilon$-(3-(mPEGyl)propionyl))Lysinamide where mPEGyl is polydisperse and has a Mw of approx 750 Da, $N^{\epsilon37}$-(3-(mPEGyl)propionyl)[Aib$^{22}$,Lys$^{37}$]GLP-1-(7-37) where mPEGyl is polydisperse and has a Mw of approx 750 Da, $N^{\epsilon37}$-(3-(mPEGyl)propionyl)[Aib$^{22}$,Lys$^{37}$]GLP-1-(7-37) amide where mPEGyl is polydisperse and has a Mw of approx 750 Da, $N^\alpha$-[Aib$^{22}$]GLP-1-(7-37)yl(N$^\epsilon$-(3-(mPEGyl)propionyl))Lysine where mPEGyl is polydisperse and has a Mw of approx 750 Da, $N^\alpha$-[Aib$^{22}$]GLP-1-(7-37)yl(N$^\epsilon$-(3-(mPEGyl)propionyl))Lysinamide where mPEGyl is polydisperse and has a Mw of approx 750 Da, $N^{\epsilon37}$-(3-(mPEGyl)propionyl)[Aib$^{8}$,Lys$^{37}$]GLP-1-(7-37) where mPEGyl is polydisperse and has a Mw of approx 750 Da, $N^{\epsilon37}$-(3-(mPEGyl)propionyl)[Aib$^{8}$,Lys$^{37}$]GLP-1-(7-37) amide where mPEGyl is polydisperse and has a Mw of approx 750 Da, $N^\alpha$-[Aib$^{8}$]GLP-1-(7-37)yl(N$^\epsilon$-(3-(mPEGyl)propionyl))Lysine where mPEGyl is polydisperse and has a Mw of approx 750 Da, $N^\alpha$-[Aib$^{8}$]GLP-1-(7-37)yl(N$^\epsilon$-(3-(mPEGyl)propionyl))Lysinamide where mPEGyl is polydisperse and has a Mw of approx 750 Da, $N^{\epsilon37}$-(3-(mPEGyl)propionyl)[Aib$^{8,35}$,Lys$^{37}$]GLP-1-(7-37) where mPEGyl is polydisperse and has a Mw of approx 750 Da, $N^{\epsilon37}$-(3-(mPEGyl)propionyl)[Aib$^{8,35}$,Lys$^{37}$]GLP-1-(7-37) amide where mPEGyl is polydisperse and has a Mw of approx 750 Da, $N^\alpha$-[Aib$^{8,35}$]GLP-1-(7-37)yl(N$^\epsilon$-(3-(mPEGyl)propionyl)) Lysine where mPEGyl is polydisperse and has a Mw of approx 750 Da, $N^\alpha$-[Aib$^{8,35}$]GLP-1-(7-37)yl(N$^\epsilon$-(3-(mPEGyl)propionyl)) Lysinamide where mPEGyl is polydisperse and has a Mw of approx 750 Da, $N^{\epsilon37}$-(3-(mPEGyl)propionyl)[Aib$^{22,35}$,Lys$^{37}$]GLP-1-(7-37) where mPEGyl is polydisperse and has a Mw of approx 750 Da, $N^{\epsilon37}$-(3-(mPEGyl)propionyl)[Aib$^{22,35}$,Lys$^{37}$]GLP-1-(7-37) amide where mPEGyl is polydisperse and has a Mw of approx 750 Da, $N^\alpha$-[Aib$^{22,35}$]GLP-1-(7-37)yl(N$^\epsilon$-(3-(mPEGyl)propionyl)) Lysine where mPEGyl is polydisperse and has a Mw of approx 750 Da, $N^\alpha$-[Aib$^{22,35}$]GLP-1-(7-37)yl(N$^\epsilon$-(3-(mPEGyl)propionyl)) Lysinamide where mPEGyl is polydisperse and has a Mw of approx 750 Da, $N^{\epsilon37}$-(3-(mPEGyl)propionyl)[Aib$^{8,35}$,Lys$^{37}$]GLP-1-(7-37) where mPEGyl is polydisperse and has a Mw of approx 750 Da, $N^{\epsilon37}$-(3-(mPEGyl)propionyl)[Aib$^{8,35}$,Lys$^{37}$]GLP-1-(7-37) amide where mPEGyl is polydisperse and has a Mw of approx 750 Da, $N^\alpha$-[Aib$^{8,35}$]GLP-1-(7-37)yl(N$^\epsilon$-(3-(mPEGyl)propionyl)) Lysine where mPEGyl is polydisperse and has a Mw of approx 750 Da, $N^\alpha$-[Aib$^{8,35}$]GLP-1-(7-37)yl(N$^\epsilon$-(3-(mPEGyl)propionyl)) Lysinamide where mPEGyl is polydisperse and has a Mw of approx 750 Da, $N^{\epsilon37}$-(3-(mPEGyl)propionyl)[Aib$^{8,22}$,Lys$^{37}$]GLP-1-(7-37) where mPEGyl is polydisperse and has a Mw of approx 750 Da, $N^{\epsilon37}$-(3-(mPEGyl)propionyl)[Aib$^{8,22}$,Lys$^{37}$]GLP-1-(7-37) amide where mPEGyl is polydisperse and has a Mw of approx 750 Da, $N^\alpha$-[Aib$^{8,22}$]GLP-1-(7-37)yl(N$^\epsilon$-(3-(mPEGyl)propionyl)) Lysine where mPEGyl is polydisperse and has a Mw of approx 750 Da, $N^\alpha$-[Aib$^{8,22}$]GLP-1-(7-37)yl(N$^\epsilon$-(3-(mPEGyl)propionyl)) Lysinamide where mPEGyl is polydisperse and has a Mw of approx 750 Da, $N^{\epsilon37}$-(3-(mPEGyl)propionyl)[Aib$^{8,22,35}$,Lys$^{37}$]GLP-1-(7-37) where mPEGyl is polydisperse and has a Mw of approx 750 Da, $N^{\epsilon37}$-(3-(mPEGyl)propionyl)[Aib$^{8,22,35}$,Lys$^{37}$]GLP-1-(7-37) amide where mPEGyl is polydisperse and has a Mw of approx 750 Da, $N^\alpha$-[Aib$^{8,22,35}$]GLP-1-(7-37)yl(N$^\epsilon$-(3-(m PEGyl)propionyl))Lysine where mPEGyl is polydisperse and has a Mw of approx 750 Da, $N^\alpha$-[Aib$^{8,22,35}$]GLP-1-(7-37)yl(N$^\epsilon$-(3-(mPEGyl)propionyl)) Lysinamide where mPEGyl is polydisperse and has a Mw of approx 750 Da, $N^\alpha$-[Aib$^{8}$,Arg$^{26,34}$]GLP-1-(7-37)yl(N$^\epsilon$-(3-(mPEGyl)propionyl))Lysine where mPEGyl is polydisperse and has a Mw of approx 750 Da, $N^\alpha$-[Aib$^{8}$,Arg$^{26,34}$]GLP-1-(7-37)yl(N$^\epsilon$-(3-(mPEGyl)propionyl))Lysinamide where mPEGyl is polydisperse and has a Mw of approx 750 Da $N^{\epsilon36}$-(3-(mPEGyl)propionyl)[Aib$^{8}$,Arg$^{26,34}$,Lys$^{36}$]GLP-1-(7-37) where mPEGyl is polydisperse and has a Mw of approx 750 Da, $N^{\epsilon36}$-(3-(mPEGyl)propionyl)[Aib$^8$,Arg$^{26,34}$,Lys$^{36}$]GLP-1-(7-37) amide where mPEGyl is polydisperse and has a Mw of approx 750 Da, $N^{\epsilon34}$-(3-(mPEGyl)propionyl)[Aib$^8$,Lys$^{26}$,Lys$^{34}$]GLP-1-(7-37) where mPEGyl is polydisperse and has a Mw of approx 750 Da, $N^{\epsilon34}$-(3-(mPEGyl)propionyl)[Aib$^8$,Lys$^{26}$,Lys$^{34}$]GLP-1-(7-37) amide where mPEGyl is polydisperse and has a Mw of approx 750 Da, $N^{\alpha}$-[Arg$^{26,34}$]GLP-1-(7-37)yl($N^{\epsilon}$-(3-(mPEGyl)propionyl))Lysine where mPEGyl is polydisperse and has a Mw of approx 750 Da, $N^{\alpha}$-[Arg$^{26,34}$]GLP-1-(7-37)yl($N^{\epsilon}$-(3-(mPEGyl)propionyl))Lysinamide where mPEGyl is polydisperse and has a Mw of approx 750 Da, $N^{\epsilon36}$-(3-(mPEGyl)propionyl)[Arg$^{26,34}$,Lys$^{36}$]GLP-1-(7-37) where mPEGyl is polydisperse and has a Mw of approx 750 Da, $N^{\epsilon36}$-(3-(mPEGyl)propionyl)[Arg$^{26,34}$,Lys$^{36}$]GLP-1-(7-37) amide where mPEGyl is polydisperse and has a Mw of approx 750 Da, $N^{\epsilon34}$-(3-(mPEGyl)propionyl)[Lys$^{26}$,Lys$^{34}$]GLP-1-(7-37) where mPEGyl is polydisperse and has a Mw of approx 750 Da, $N^{\epsilon34}$-(3-(mPEGyl)propionyl)[Lys$^{26}$,Lys$^{34}$]GLP-1-(7-37) amide where mPEGyl is polydisperse and has a Mw of approx 750 Da, $N^{\alpha}$-[Ala$^8$,Arg$^{26,34}$,]GLP-1-(7-37)yl($N^{\epsilon}$-(3-(mPEGyl)propionyl))Lysine where mPEGyl is polydisperse and has a Mw of approx 750 Da, $N^{\alpha}$-[Ala$^8$,Arg$^{26,34}$]GLP-1-(7-37)yl($N^{\epsilon}$-(3-(mPEGyl)propionyl))Lysinamide where mPEGyl is polydisperse and has a Mw of approx 750 Da, $N^{\epsilon36}$-(3-(mPEGyl)propionyl)[Ala$^8$,Arg$^{26,34}$,Lys$^{36}$]GLP-1-(7-37) where mPEGyl is polydisperse and has a Mw of approx 750 Da, $N^{\epsilon36}$-(3-(mPEGyl)propionyl)[Ala$^8$,Arg$^{26,34}$,Lys$^{36}$]GLP-1-(7-37) amide where mPEGyl is polydisperse and has a Mw of approx 750 Da, $N^{\epsilon34}$-(3-(mPEGyl)propionyl)[Ala$^8$,Lys$^{26}$,Lys$^{34}$]GLP-1-(7-37) where mPEGyl is polydisperse and has a Mw of approx 750 Da, $N^{\epsilon34}$-(3-(mPEGyl)propionyl)[Ala$^8$,Lys$^{26}$,Lys$^{34}$]GLP-1-(7-37) amide where mPEGyl is polydisperse and has a Mw of approx 750 Da, $N^{\epsilon20}$-(3-(mPEGyl)propionyl)[Lys$^{20}$]Exendin-4-(1-39) amide where mPEGyl is polydisperse and has a Mw of approx 750 Da, $N^{\epsilon32}$-(3-(mPEGyl)propionyl)[Lys$^{32}$]Exendin-4-(1-39) amide where mPEGyl is polydisperse and has a Mw of approx 750 Da, $N^{\epsilon20}$-(3-(mPEGyl)propionyl)[Lys$^{20}$,Arg$^{12,27}$]Exendin-4-(1-39) amide where mPEGyl is polydisperse and has a Mw of approx 750 Da, and $N^{\epsilon32}$-(3-(mPEGyl)propionyl)[Lys$^{32}$,Arg$^{12,27}$]Exendin-4-(1-39) amide where mPEGyl is polydisperse and has a Mw of approx 750 Da.

In another embodiment the compound according to the present invention is selected from the group consisting of $N^{\epsilon37}$-(3-(mPEGyl)propionyl)[Lys$^{37}$]GLP-1-(7-37) where mPEGyl is polydisperse and has a Mw of approx 2000 Da, $N^{\epsilon37}$-(3-(mPEGyl)propionyl)[Lys$^{37}$]GLP-1-(7-37) amide where mPEGyl is polydisperse and has a Mw of approx 2000 Da, GLP-1-(7-37)yl($N^{\epsilon}$-(3-(mPEGyl)propionyl))Lysine where mPEGyl is polydisperse and has a Mw of approx 2000 Da, GLP-1-(7-37)yl($N^{\epsilon}$-(3-(mPEGyl)propionyl))Lysinamide where mPEGyl is polydisperse and has a Mw of approx 2000 Da, $N^{\epsilon37}$-(3-(mPEGyl)propionyl)[Aib$^{35}$,Lys$^{37}$]GLP-1-(7-37) where mPEGyl is polydisperse and has a Mw of approx 2000 Da, $N^{\epsilon37}$-(3-(mPEGyl)propionyl)[Aib$^{35}$,Lys$^{37}$]GLP-1-(7-37) amide where mPEGyl is polydisperse and has a Mw of approx 2000 Da, $N^{\alpha}$-[Aib$^{35}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{35}$]GLP-1-(7-37)yl($N^{\epsilon}$-(3-(mPEGyl)propionyl))Lysinamide where mPEGyl is polydisperse and has a Mw of approx 2000 Da, $N^{\epsilon37}$-(3-(mPEGyl)propionyl)[Aib$^{22}$,Lys$^{37}$]GLP-1-(7-37) where mPEGyl is polydisperse and has a Mw of approx 2000 Da, $N^{\epsilon37}$-(3-(mPEGyl)propionyl)[Aib$^{22}$,Lys$^{37}$]GLP-1-(7-37) amide where mPEGyl is polydisperse and has a Mw of approx 2000 Da, $N^{\alpha}$-[Aib$^{22}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{22}$]GLP-1-(7-37)yl($N^{\epsilon}$-(3-(mPEGyl)propionyl))Lysinamide where mPEGyl is polydisperse and has a Mw of approx 2000 Da, $N^{\epsilon37}$-(3-(mPEGyl)propionyl)[Aib$^8$,Lys$^{37}$]GLP-1-(7-37) where mPEGyl is polydisperse and has a Mw of approx 2000 Da, $N^{\epsilon37}$-(3-(mPEGyl)propionyl)[Aib$^8$,Lys$^{37}$]GLP-1-(7-37) amide where mPEGyl is polydisperse and has a Mw of approx 2000 Da, $N^{\alpha}$-[Aib$^8$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^8$]GLP-1-(7-37)yl($N^{\epsilon}$-(3-(mPEGyl)propionyl))Lysinamide where mPEGyl is polydisperse and has a Mw of approx 2000 Da, $N^{\epsilon37}$-(3-(mPEGyl)propionyl)[Aib$^{8,35}$,Lys$^{37}$]GLP-1-(7-37) where mPEGyl is polydisperse and has a Mw of approx 2000 Da, $N^{\epsilon37}$-(3-(mPEGyl)propionyl)[Aib$^{8,35}$,Lys$^{37}$]GLP-1-(7-37) amide where mPEGyl is polydisperse and has a Mw of approx 2000 Da, $N^{\alpha}$-[Aib$^{8,35}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{8,35}$]GLP-1-(7-37)yl($N^{\epsilon}$-(3-(mPEGyl)propionyl))Lysinamide where mPEGyl is polydisperse and has a Mw of approx 2000 Da, $N^{\epsilon37}$-(3-(mPEGyl)propionyl)[Aib$^{22,35}$,Lys$^{37}$]GLP-1-(7-37) where mPEGyl is polydisperse and has a Mw of approx 2000 Da, $N^{\epsilon37}$-(3-(mPEGyl)propionyl)[Aib$^{22,35}$,Lys$^{37}$]GLP-1-(7-37) amide where mPEGyl is polydisperse and has a Mw of approx 2000 Da, $N^{\alpha}$-[Aib$^{22,35}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{22,35}$]GLP-1-(7-37)yl($N^{\epsilon}$-(3-(mPEGyl)propionyl))Lysinamide where mPEGyl is polydisperse and has a Mw of approx 2000 Da, $N^{\epsilon 37}$-(3-(mPEGyl)propionyl)[Aib$^{8,35}$,Lys$^{37}$]GLP-1-(7-37) where mPEGyl is polydisperse and has a Mw of approx 2000 Da, $N^{\epsilon 37}$-(3-(mPEGyl)propionyl)[Aib$^{8,35}$,Lys$^{37}$]GLP-1-(7-37) amide where mPEGyl is polydisperse and has a Mw of approx 2000 Da, $N^{\alpha}$-[Aib$^{8,35}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{8,35}$]GLP-1-(7-37)yl($N^{\epsilon}$-(3-(mPEGyl)propionyl))Lysinamide where mPEGyl is polydisperse and has a Mw of approx 2000 Da, $N^{\epsilon 37}$-(3-(mPEGyl)propionyl)[Aib$^{8,22}$,Lys$^{37}$]GLP-1-(7-37) where mPEGyl is polydisperse and has a Mw of approx 2000 Da, $N^{\epsilon 37}$-(3-(mPEGyl)propionyl)[Aib$^{8,22}$,Lys$^{37}$]GLP-1-(7-37) amide where mPEGyl is polydisperse and has a Mw of approx 2000 Da, $N^{\alpha}$-[Aib$^{8,22}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{8,22}$]GLP-1-(7-37)yl($N^{\epsilon}$-(3-(mPEGyl)propionyl))Lysinamide where mPEGyl is polydisperse and has a Mw of approx 2000 Da, $N^{\epsilon 37}$-(3-(mPEGyl)propionyl)[Aib$^{8,22,35}$,Lys$^{37}$]GLP-1-(7-37) where mPEGyl is polydisperse and has a Mw of approx 2000 Da, $N^{\epsilon 37}$-(3-(mPEGyl)propionyl)[Aib$^{8,22,35}$,Lys$^{37}$]GLP-1-(7-37) amide where mPEGyl is polydisperse and has a Mw of approx 2000 Da, $N^{\alpha}$-[Aib$^{8,22,35}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{8,22,35}$]GLP-1-(7-37)yl($N^{\epsilon}$-(3-(mPEGyl)propionyl))Lysinamide where mPEGyl is polydisperse and has a Mw of approx 2000 Da, $N^{\alpha}$-[Aib$^{8}$,Arg$^{26,34}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Aib$^{8}$,Arg$^{26,34}$]GLP-1-(7-37)yl($N^{\epsilon}$-(3-(mPEGyl)propionyl))Lysinamide where mPEGyl is polydisperse and has a Mw of approx 2000 Da $N^{\epsilon 36}$-(3-(mPEGyl)propionyl)[Aib$^{8}$,Arg$^{26,34}$,Lys$^{36}$]GLP-1-(7-37) where mPEGyl is polydisperse and has a Mw of approx 2000 Da, $N^{\epsilon 36}$-(3-(mPEGyl)propionyl)[Aib$^{8}$,Arg$^{26,34}$,Lys$^{36}$]GLP-1-(7-37) amide where mPEGyl is polydisperse and has a Mw of approx 2000 Da, $N^{\epsilon 34}$-(3-(mPEGyl)propionyl)[Aib$^{8}$,Lys$^{26}$,Lys$^{34}$]GLP-1-(7-37) where mPEGyl is polydisperse and has a Mw of approx 2000 Da, $N^{\epsilon 34}$-(3-(mPEGyl)propionyl)[Aib$^{8}$,Lys$^{26}$,Lys$^{34}$]GLP-1-(7-37) amide where mPEGyl is polydisperse and has a Mw of approx 2000 Da, $N^{\alpha}$-[Arg$^{26,34}$]GLP-1-(7-37)yl($N^{\epsilon}$-(3-(mPEGyl)propionyl))Lysine where mPEGyl is polydisperse and has a Mw of approx 2000 Da, $N^{\alpha}$-[Arg$^{26,34}$]GLP-1-(7-37)yl($N^{\epsilon}$-(3-(mPEGyl)propionyl))Lysinamide where mPEGyl is polydisperse and has a Mw of approx 2000 Da, $N^{\epsilon 36}$-(3-(mPEGyl)propionyl)[Arg$^{26,34}$,Lys$^{36}$]GLP-1-(7-37) where mPEGyl is polydisperse and has a Mw of approx 2000 Da, $N^{\epsilon 36}$-(3-(mPEGyl)propionyl)[Arg$^{26,34}$,Lys$^{36}$]GLP-1-(7-37) amide where mPEGyl is polydisperse and has a Mw of approx 2000 Da, $N^{\epsilon 34}$-(3-(mPEGyl)propionyl)[Lys$^{26}$,Lys$^{34}$]GLP-1-(7-37) where mPEGyl is polydisperse and has a Mw of approx 2000 Da, $N^{\epsilon 34}$-(3-(mPEGyl)propionyl)[Lys$^{26}$,Lys$^{34}$]GLP-1-(7-37) amide where mPEGyl is polydisperse and has a Mw of approx 2000 Da, $N^{\alpha}$-[Ala$^{8}$,Arg$^{26,34}$,]GLP-1-(7-37)yl($N^{\epsilon}$-(3-(mPEGyl)propionyl))Lysine where mPEGyl is polydisperse and has a Mw of approx 2000 Da, $N^{\alpha}$-[Ala$^{8}$,Arg$^{26,34}$]GLP-1-(7-37)yl($N^{\epsilon}$-(3-(mPEGyl)propionyl))Lysinamide where mPEGyl is polydisperse and has a Mw of approx 2000 Da, $N^{\epsilon 36}$-(3-(mPEGyl)propionyl)[Ala$^{8}$,Arg$^{26,34}$,Lys$^{36}$]GLP-1-(7-37) where mPEGyl is polydisperse and has a Mw of approx 2000 Da, $N^{\epsilon 36}$-(3-(mPEGyl)propionyl)[Ala$^{8}$,Arg$^{26,34}$,Lys$^{36}$]GLP-1-(7-37) amide where mPEGyl is polydisperse and has a Mw of approx 2000 Da, $N^{\epsilon 34}$-(3-(mPEGyl)propionyl)[Ala$^{8}$,Lys$^{26}$,Lys$^{34}$]GLP-1-(7-37) where mPEGyl is polydisperse and has a Mw of approx 2000 Da, $N^{\epsilon 34}$-(3-(mPEGyl)propionyl)[Ala$^{8}$,Lys$^{26}$,Lys$^{34}$]GLP-1-(7-37) amide where mPEGyl is polydisperse and has a Mw of approx 2000 Da, $N^{\epsilon 20}$-(3-(mPEGyl)propionyl)[Lys$^{20}$]Exendin-4-(1-39) amide where mPEGyl is polydisperse and has a Mw of approx 2000 Da, $N^{\epsilon 32}$-(3-(mPEGyl)propionyl)[Lys$^{32}$]Exendin-4-(1-39) amide where mPEGyl is polydisperse and has a Mw of approx 2000 Da, $N^{\epsilon 20}$-(3-(mPEGyl)propionyl)[Lys$^{20}$,Arg$^{12,27}$]Exendin-4-(1-39) amide where mPEGyl is polydisperse and has a Mw of approx 2000 Da, and $N^{\epsilon 32}$-(3-(mPEGyl)propionyl)[Lys$^{32}$,Arg$^{12,27}$]Exendin-4-(1-39) amide where mPEGyl is polydisperse and has a Mw of approx 2000 Da.

In another embodiment the compound according to the present invention is selected from the group consisting of $N^{\epsilon 37}$-(3-(mPEGyl)propionyl)[Lys$^{37}$]GLP-1-(7-37) where mPEGyl is polydisperse and has a Mw of approx 5000 Da, $N^{\epsilon 37}$-(3-(mPEGyl)propionyl)[Lys$^{37}$]GLP-1-(7-37) amide where mPEGyl is polydisperse and has a Mw of approx 5000 Da, GLP-1-(7-37)yl($N^{\epsilon}$-(3-(mPEGyl)propionyl))Lysine where mPEGyl is polydisperse and has a Mw of approx 5000 Da, GLP-1-(7-37)yl($N^{\epsilon}$-(3-(mPEGyl)propionyl))Lysinamide where mPEGyl is polydisperse and has a Mw of approx 5000 Da, $N^{\epsilon 37}$-(3-(mPEGyl)propionyl)[Aib$^{35}$,Lys$^{37}$]GLP-1-(7-37) where mPEGyl is polydisperse and has a Mw of approx 5000 Da, $N^{\epsilon 37}$-(3-(mPEGyl)propionyl)[Aib$^{35}$,Lys$^{37}$]GLP-1-(7-37) amide where mPEGyl is polydisperse and has a Mw of approx 5000 Da, $N^{\alpha}$-[Aib$^{35}$]GLP-1-(7-37)yl($N^{\epsilon}$-(3-(mPEGyl)propionyl))Lysine where mPEGyl is polydisperse and has a Mw of approx 5000 Da, $N^{\alpha}$-[Aib$^{\pm}$]GLP-1-(7-37)yl($N^{\epsilon}$-(3-(mPEGyl)propionyl))Lysinamide where mPEGyl is polydisperse and has a Mw of approx 5000 Da, $N^{\epsilon 37}$-(3-(mPEGyl)propionyl)[Aib$^{22}$,Lys$^{37}$]GLP-1-(7-37) where mPEGyl is polydisperse and has a Mw of approx 5000 Da, $N^{\epsilon37}$-(3-(mPEGyl)propionyl)[Aib$^{22}$,Lys$^{37}$]GLP-1-(7-37) amide where mPEGyl is polydisperse and has a Mw of approx 5000 Da, $N^{\alpha}$-[Aib$^{22}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{22}$]GLP-1-(7-37)yl(N$^{\epsilon}$-(3-(mPEGyl)propionyl))Lysinamide where mPEGyl is polydisperse and has a Mw of approx 5000 Da, $N^{\epsilon37}$-(3-(mPEGyl)propionyl)[Aib$^{8}$,Lys$^{37}$]GLP-1-(7-37) where mPEGyl is polydisperse and has a Mw of approx 5000 Da, $N^{\epsilon37}$-(3-(mPEGyl)propionyl)[Aib$^{8}$,Lys$^{37}$]GLP-1-(7-37) amide where mPEGyl is polydisperse and has a Mw of approx 5000 Da, $N^{\alpha}$-[Aib$^{8}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{8}$]GLP-1-(7-37)yl(N$^{\epsilon}$-(3-(mPEGyl)propionyl))Lysinamide where mPEGyl is polydisperse and has a Mw of approx 5000 Da, $N^{\epsilon37}$-(3-(mPEGyl)propionyl)[Aib$^{8,35}$,Lys$^{37}$]GLP-1-(7-37) where mPEGyl is polydisperse and has a Mw of approx 5000 Da, $N^{\epsilon37}$-(3-(mPEGyl)propionyl)[Aib$^{8,35}$,Lys$^{37}$]GLP-1-(7-37) amide where mPEGyl is polydisperse and has a Mw of approx 5000 Da, $N^{\alpha}$-[Aib$^{8,35}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{8,35}$]GLP-1-(7-37)yl(N$^{\epsilon}$-(3-(mPEGyl)propionyl))Lysinamide where mPEGyl is polydisperse and has a Mw of approx 5000 Da, $N^{\epsilon37}$-(3-(mPEGyl)propionyl)[Aib$^{22,35}$,Lys$^{37}$]GLP-1-(7-37) where mPEGyl is polydisperse and has a Mw of approx 5000 Da, $N^{\epsilon37}$-(3-(mPEGyl)propionyl)[Aib$^{22,35}$,Lys$^{37}$]GLP-1-(7-37) amide where mPEGyl is polydisperse and has a Mw of approx 5000 Da, $N^{\alpha}$-[Aib$^{22,35}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{22,35}$]GLP-1-(7-37)yl(N$^{\epsilon}$-(3-(mPEGyl)propionyl))Lysinamide where mPEGyl is polydisperse and has a Mw of approx 5000 Da, $N^{\epsilon37}$-(3-(mPEGyl)propionyl)[Aib$^{8,35}$,Lys$^{37}$]GLP-1-(7-37) where mPEGyl is polydisperse and has a Mw of approx 5000 Da, $N^{\epsilon37}$-(3-(mPEGyl)propionyl)[Aib$^{8,35}$,Lys$^{37}$]GLP-1-(7-37) amide where mPEGyl is polydisperse and has a Mw of approx 5000 Da, $N^{\alpha}$-[Aib$^{8,35}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{8,35}$]GLP-1-(7-37)yl(N$^{\epsilon}$-(3-(mPEGyl)propionyl))Lysinamide where mPEGyl is polydisperse and has a Mw of approx 5000 Da, $N^{\epsilon37}$-(3-(mPEGyl)propionyl)[Aib$^{8,22}$,Lys$^{37}$]GLP-1-(7-37) where mPEGyl is polydisperse and has a Mw of approx 5000 Da, $N^{\epsilon37}$-(3-(mPEGyl)propionyl)[Aib$^{8,22}$,Lys$^{37}$]GLP-1-(7-37) amide where mPEGyl is polydisperse and has a Mw of approx 5000 Da, $N^{\alpha}$-[Aib$^{8,22}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{8,22}$]GLP-1-(7-37)yl(N$^{\epsilon}$-(3-(mPEGyl)propionyl))Lysinamide where mPEGyl is polydisperse and has a Mw of approx 5000 Da, $N^{\epsilon37}$-(3-(mPEGyl)propionyl)[Aib$^{8,22,35}$,Lys$^{37}$]GLP-1-(7-37) where mPEGyl is polydisperse and has a Mw of approx 5000 Da, $N^{\epsilon37}$-(3-(mPEGyl)propionyl)[Aib$^{8,22,35}$,Lys$^{37}$]GLP-1-(7-37) amide where mPEGyl is polydisperse and has a Mw of approx 5000 Da, $N^{\alpha}$-[Aib$^{8,22,35}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{8,22,35}$]GLP-1-(7-37)yl(N$^{\epsilon}$-(3-(mPEGyl)propionyl))Lysinamide where mPEGyl is polydisperse and has a Mw of approx 5000 Da, $N^{\alpha}$-[Aib$^{8}$,Arg$^{26,34}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Aib$^{8}$,Arg$^{26,34}$]GLP-1-(7-37)yl(N$^{\epsilon}$-(3-(mPEGyl)propionyl))Lysinamide where mPEGyl is polydisperse and has a Mw of approx 5000 Da $N^{\epsilon36}$-(3-(mPEGyl)propionyl)[Aib$^{8}$,Arg$^{26,34}$,Lys$^{36}$]GLP-1-(7-37) where mPEGyl is polydisperse and has a Mw of approx 5000 Da, $N^{\epsilon36}$-(3-(mPEGyl)propionyl)[Aib$^{8}$,Arg$^{26,34}$,Lys$^{36}$]GLP-1-(7-37) amide where mPEGyl is polydisperse and has a Mw of approx 5000 Da, $N^{\epsilon34}$-(3-(mPEGyl)propionyl)[Aib$^{8}$,Lys$^{26}$,Lys$^{34}$]GLP-1-(7-37) where mPEGyl is polydisperse and has a Mw of approx 5000 Da, $N^{\epsilon34}$-(3-(mPEGyl)propionyl)[Aib$^{8}$,Lys$^{26}$,Lys$^{34}$]GLP-1-(7-37) amide where mPEGyl is polydisperse and has a Mw of approx 5000 Da, $N^{\alpha}$-[Arg$^{26,34}$]GLP-1-(7-37)yl(N$^{\epsilon}$-(3-(mPEGyl)propionyl))Lysine where mPEGyl is polydisperse and has a Mw of approx 5000 Da, $N^{\alpha}$-[Arg$^{26,34}$]GLP-1-(7-37)yl(N$^{\epsilon}$-(3-(mPEGyl)propionyl))Lysinamide where mPEGyl is polydisperse and has a Mw of approx 5000 Da, $N^{\epsilon36}$-(3-(mPEGyl)propionyl)[Arg$^{26,34}$,Lys$^{36}$]GLP-1-(7-37) where mPEGyl is polydisperse and has a Mw of approx 5000 Da, $N^{\epsilon36}$-(3-(mPEGyl)propionyl)[Arg$^{26,34}$,Lys$^{36}$]GLP-1-(7-37) amide where mPEGyl is polydisperse and has a Mw of approx 5000 Da, $N^{\epsilon34}$-(3-(mPEGyl)propionyl)[Lys$^{26}$,Lys$^{34}$]GLP-1-(7-37) where mPEGyl is polydisperse and has a Mw of approx 5000 Da, $N^{\epsilon34}$-(3-(mPEGyl)propionyl)[Lys$^{26}$,Lys$^{34}$]GLP-1-(7-37) amide where mPEGyl is polydisperse and has a Mw of approx 5000 Da, $N^{\alpha}$-[Ala$^{8}$,Arg$^{26,34}$,]GLP-1-(7-37)yl(N$^{\epsilon}$-(3-(mPEGyl)propionyl))Lysine where mPEGyl is polydisperse and has a Mw of approx 5000 Da, $N^{\alpha}$-[Ala$^{8}$,Arg$^{26,34}$]GLP-1-(7-37)yl(N$^{\epsilon}$-(3-(mPEGyl)propionyl))Lysinamide where mPEGyl is polydisperse and has a Mw of approx 5000 Da, $N^{\epsilon36}$-(3-(mPEGyl)propionyl)[Ala$^{8}$,Arg$^{26,34}$,Lys$^{36}$]GLP-1-(7-37) where mPEGyl is polydisperse and has a Mw of approx 5000 Da, $N^{\epsilon36}$-(3-(mPEGyl)propionyl)[Ala$^{8}$,Arg$^{26,34}$,Lys$^{36}$]GLP-1-(7-37) amide where mPEGyl is polydisperse and has a Mw of approx 5000 Da, $N^{\epsilon34}$-(3-(mPEGyl)propionyl)[Ala$^{8}$,Lys$^{26}$,Lys$^{34}$]GLP-1-(7-37) where mPEGyl is polydisperse and has a Mw of approx 5000 Da, $N^{\epsilon 34}$-(3-(mPEGyl)propionyl)[Ala$^8$,Lys$^{26}$,Lys$^{34}$]GLP-1-(7-37) amide where mPEGyl is polydisperse and has a Mw of approx 5000 Da, $N^{\epsilon 20}$-(3-(mPEGyl)propionyl)[Lys$^{20}$]Exendin-4-(1-39) amide where mPEGyl is polydisperse and has a Mw of approx 5000 Da, $N^{\epsilon 32}$-(3-(mPEGyl)propionyl)[Lys$^{32}$]Exendin-4-(1-39) amide where mPEGyl is polydisperse and has a Mw of approx 5000 Da, $N^{\epsilon 20}$-(3-(mPEGyl)propionyl)[Lys$^{20}$,Arg$^{12,27}$]Exendin-4-(1-39) amide where mPEGyl is polydisperse and has a Mw of approx 5000 Da, and $N^{\epsilon 32}$-(3-(mPEGyl)propionyl)[Lys$^{32}$,Arg$^{12,27}$]Exendin-4-(1-39) amide where mPEGyl is polydisperse and has a Mw of approx 5000 Da.

In another embodiment the compound according to the present invention is selected from the group consisting of $N^{\epsilon 37}$-(3-(mPEGyl)propionyl)[Lys$^{37}$]GLP-1-(7-37) where mPEGyl is polydisperse and has a Mw of approx 10 kDa, $N^{\epsilon 37}$-(3-(mPEGyl)propionyl)[Lys$^{37}$]GLP-1-(7-37) amide where mPEGyl is polydisperse and has a Mw of approx 10 kDa, GLP-1-(7-37)yl($N^{\epsilon}$-(3-(mPEGyl)propionyl))Lysine where mPEGyl is polydisperse and has a Mw of approx 10 kDa, GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^{35}$,Lys$^{37}$]GLP-1-(7-37) where mPEGyl is polydisperse and has a Mw of approx 10 kDa, $N^{\epsilon 37}$-(3-(mPEGyl)propionyl)[Aib$^{35}$,Lys$^{37}$]GLP-1-(7-37) amide where mPEGyl is polydisperse and has a Mw of approx 10 kDa, $N^{\alpha}$-[Aib$^{35}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^{35}$]GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^{22}$,Lys$^{37}$]GLP-1-(7-37) where mPEGyl is polydisperse and has a Mw of approx 10 kDa, $N^{\epsilon 37}$-(3-(mPEGyl)propionyl)[Aib$^{22}$,Lys$^{37}$]GLP-1-(7-37) amide where mPEGyl is polydisperse and has a Mw of approx 10 kDa, $N^{\alpha}$-[Aib$^{22}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^{22}$]GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^8$,Lys$^{37}$]GLP-1-(7-37) where mPEGyl is polydisperse and has a Mw of approx 10 kDa, $N^{\epsilon 37}$-(3-(mPEGyl)propionyl)[Aib$^8$,Lys$^{37}$]GLP-1-(7-37) amide where mPEGyl is polydisperse and has a Mw of approx 10 kDa, $N^{\alpha}$-[Aib$^8$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^8$]GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^{8,35}$,Lys$^{37}$]GLP-1-(7-37) where mPEGyl is polydisperse and has a Mw of approx 10 kDa, $N^{\epsilon 37}$-(3-(mPEGyl)propionyl)[Aib$^{8,35}$,Lys$^{37}$]GLP-1-(7-37) amide where mPEGyl is polydisperse and has a Mw of approx 10 kDa, $N^{\alpha}$-[Aib$^{8,35}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^{8,35}$]GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^{22,35}$,Lys$^{37}$]GLP-1-(7-37) where mPEGyl is polydisperse and has a Mw of approx 10 kDa, $N^{\epsilon 37}$-(3-(mPEGyl)propionyl)[Aib$^{22,35}$,Lys$^{37}$]GLP-1-(7-37) amide where mPEGyl is polydisperse and has a Mw of approx 10 kDa, $N^{\alpha}$-[Aib$^{22,35}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^{22,35}$]GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^{8,35}$,Lys$^{37}$]GLP-1-(7-37) where mPEGyl is polydisperse and has a Mw of approx 10 kDa, $N^{\epsilon 37}$-(3-(mPEGyl)propionyl)[Aib$^{8,35}$,Lys$^{37}$]GLP-1-(7-37) amide where mPEGyl is polydisperse and has a Mw of approx 10 kDa, $N^{\alpha}$-[Aib$^{8,35}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^{8,35}$]GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^{8,22}$,Lys$^{37}$]GLP-1-(7-37) where mPEGyl is polydisperse and has a Mw of approx 10 kDa, $N^{\epsilon 37}$-(3-(mPEGyl)propionyl)[Aib$^{8,22}$,Lys$^{37}$]GLP-1-(7-37) amide where mPEGyl is polydisperse and has a Mw of approx 10 kDa, $N^{\alpha}$-[Aib$^{8,22}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^{8,22}$]GLP-1-(7-37)yl($N^{\epsilon}$-(3-(mPEGyl)propionyl))Lysinamide where mPEGyl is polydisperse and has a Mw of approx 10 kDa, $N^{\epsilon 37}$-(3-(mPEGyl)propionyl)[Aib$^{8,22,35}$,Lys$^{37}$]GLP-1-(7-37) where mPEGyl is polydisperse and has a Mw of approx 10 kDa, $N^{\epsilon 37}$-(3-(mPEGyl)propionyl)[Aib$^{8,22,35}$,Lys$^{37}$]GLP-1-(7-37) amide where mPEGyl is polydisperse and has a Mw of approx 10 kDa, $N^{\alpha}$-[Aib$^{8,22,35}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^{8,22,35}$]GLP-1-(7-37)yl($N^{\epsilon}$-(3-(mPEGyl)propionyl))Lysinamide where mPEGyl is polydisperse and has a Mw of approx 10 kDa, $N^{\alpha}$-[Aib$^8$,Arg$^{26,34}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Aib$^8$,Arg$^{26,34}$]GLP-1-(7-37)yl($N^{\epsilon}$-(3-(mPEGyl)propionyl))Lysinamide where mPEGyl is polydisperse and has a Mw of approx 10 kDa $N^{\epsilon 36}$-(3-(mPEGyl)propionyl)[Aib$^8$,Arg$^{26,34}$,Lys$^{36}$]GLP-1-(7-37) where mPEGyl is polydisperse and has a Mw of approx 10 kDa, $N^{\epsilon 36}$-(3-(mPEGyl)propionyl)[Aib$^8$,Arg$^{26,34}$,Lys$^{36}$]GLP-1-(7-37) amide where mPEGyl is polydisperse and has a Mw of approx 10 kDa, $N^{\epsilon 34}$-(3-(mPEGyl)propionyl)[Aib$^8$,Lys$^{26}$,Lys$^{34}$]GLP-1-(7-37) where mPEGyl is polydisperse and has a Mw of approx 10 kDa, $N^{\epsilon 34}$-(3-(mPEGyl)propionyl)[Aib$^8$,Lys$^{26}$,Lys$^{34}$]GLP-1-(7-37) amide where mPEGyl is polydisperse and has a Mw of approx 10 kDa, $N^{\alpha}$-[Arg$^{26,34}$]GLP-1-(7-37)yl($N^{\epsilon}$-(3-(mPEGyl)propionyl))Lysine where mPEGyl is polydisperse and has a Mw of approx 10 kDa, $N^{\alpha}$-[Arg$^{26,34}$]GLP-1-(7-37)yl($N^{\epsilon}$-(3-(mPEGyl)propionyl))Lysinamide where mPEGyl is polydisperse and has a Mw of approx 10 kDa, $N^{\epsilon 36}$-(3-(mPEGyl)propionyl)[Arg$^{26,34}$,Lys$^{36}$]GLP-1-(7-37) where mPEGyl is polydisperse and has a Mw of approx 10 kDa, $N^{\epsilon 36}$-(3-(mPEGyl)propionyl)[Arg$^{26,34}$,Lys$^{36}$]GLP-1-(7-37) amide where mPEGyl is polydisperse and has a Mw of approx 10 kDa, $N^{\epsilon 34}$-(3-(mPEGyl)propionyl)[Lys$^{26}$,Lys$^{34}$]GLP-1-(7-37) where mPEGyl is polydisperse and has a Mw of approx 10 kDa, $N^{\epsilon 34}$-(3-(mPEGyl)propionyl)[Lys$^{26}$,Lys$^{34}$]GLP-1-(7-37) amide where mPEGyl is polydisperse and has a Mw of approx 10 kDa, $N^{\alpha}$-[Ala$^8$,Arg$^{26,34}$,]GLP-1-(7-37)yl($N^{\epsilon}$-(3-(mPEGyl)propionyl))Lysine where mPEGyl is polydisperse and has a Mw of approx 10 kDa, $N^{\alpha}$-[Ala$^8$,Arg$^{26,34}$]GLP-1-(7-37)yl($N^{\epsilon}$-(3-(mPEGyl)propionyl))Lysinamide where mPEGyl is polydisperse and has a Mw of approx 10 kDa, $N^{\epsilon 36}$-(3-(mPEGyl)propionyl)[Ala$^8$,Arg$^{26,34}$,Lys$^{36}$]GLP-1-(7-37) where mPEGyl is polydisperse and has a Mw of approx 10 kDa, $N^{\epsilon 36}$-(3-(mPEGyl)propionyl)[Ala$^8$,Arg$^{26,34}$,Lys$^{36}$]GLP-1-(7-37) amide where mPEGyl is polydisperse and has a Mw of approx 10 kDa, $N^{\epsilon 34}$-(3-(mPEGyl)propionyl)[Ala$^8$,Lys$^{26}$,Lys$^{34}$]GLP-1-(7-37) where mPEGyl is polydisperse and has a Mw of approx 10 kDa, $N^{\epsilon 34}$-(3-(mPEGyl)propionyl)[Ala$^8$,Lys$^{26}$,Lys$^{34}$]GLP-1-(7-37) amide where mPEGyl is polydisperse and has a Mw of approx 10 kDa, $N^{\epsilon 20}$-(3-(mPEGyl)propionyl)[Lys$^{20}$]Exendin-4-(1-39) amide where mPEGyl is polydisperse and has a Mw of approx 10 kDa, $N^{\epsilon 32}$-(3-(mPEGyl)propionyl)[Lys$^{32}$]Exendin-4-(1-39) amide where mPEGyl is polydisperse and has a Mw of approx 10 kDa, $N^{\epsilon 20}$-(3-(mPEGyl)propionyl)[Lys$^{20}$,Arg$^{12,27}$]Exendin-4-(1-39) amide where mPEGyl is polydisperse and has a Mw of approx 10 kDa, and $N^{\epsilon 32}$-(3-(mPEGyl)propionyl)[Lys$^{32}$,Arg$^{12,27}$]Exendin-4-(1-39) amide where mPEGyl is polydisperse and has a Mw of approx 10 kDa.

In another embodiment the compound according to the present invention is selected from the group consisting of
$N^{\epsilon 37}$-(3-(mPEGyl)propionyl)[Lys$^{37}$]GLP-1-(7-37) where mPEGyl is polydisperse and has a Mw of approx 20 kDa, $N^{\epsilon 37}$-(3-(mPEGyl)propionyl)[Lys$^{37}$]GLP-1-(7-37) amide where mPEGyl is polydisperse and has a Mw of approx 20 kDa, GLP-1-(7-37)yl($N^{\epsilon}$-(3-(mPEGyl)propionyl))Lysine where mPEGyl is polydisperse and has a Mw of approx 20 kDa, GLP-1-(7-37)yl($N^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{35}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{35}$,Lys$^{37}$]GLP-1-(7-37) amide where mPEGyl is polydisperse and has a Mw of approx 20 kDa, $N^{\alpha}$-[Aib$^{35}$]GLP-1-(7-37)yl($N^{\epsilon}$-(3-(mPEGyl)propionyl))Lysine where mPEGyl is polydisperse and has a Mw of approx 20 kDa, $N^{\alpha}$-[Aib$^{35}$]GLP-1-(7-37)yl($N^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{22}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{22}$,Lys$^{37}$]GLP-1-(7-37) amide where mPEGyl is polydisperse and has a Mw of approx 20 kDa, $N^{\alpha}$-[Aib$^{22}$]GLP-1-(7-37)yl($N^{\epsilon}$-(3-(mPEGyl)propionyl))Lysine where mPEGyl is polydisperse and has a Mw of approx 20 kDa, $N^{\alpha}$-[Aib$^{22}$]GLP-1-(7-37)yl($N^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{8}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{8}$,Lys$^{37}$]GLP-1-(7-37) amide where mPEGyl is polydisperse and has a Mw of approx 20 kDa, $N^{\alpha}$-[Aib$^{8}$]GLP-1-(7-37)yl($N^{\epsilon}$-(3-(mPEGyl)propionyl))Lysine where mPEGyl is polydisperse and has a Mw of approx 20 kDa, $N^{\alpha}$-[Aib$^{8}$]GLP-1-(7-37)yl($N^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{8,35}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{8,35}$,Lys$^{37}$]GLP-1-(7-37) amide where mPEGyl is polydisperse and has a Mw of approx 20 kDa, $N^{\alpha}$-[Aib$^{8,35}$]GLP-1-(7-37)yl($N^{\epsilon}$-(3-(mPEGyl)propionyl))Lysine where mPEGyl is polydisperse and has a Mw of approx 20 kDa, $N^{\alpha}$-[Aib$^{8,35}$]GLP-1-(7-37)yl($N^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{22,35}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{22,35}$,Lys$^{37}$]GLP-1-(7-37) amide where mPEGyl is polydisperse and has a Mw of approx 20 kDa, $N^{\alpha}$-[Aib$^{22,35}$]GLP-1-(7-37)yl($N^{\epsilon}$-(3-(mPEGyl)propionyl))Lysine where mPEGyl is polydisperse and has a Mw of approx 20 kDa, $N^{\alpha}$-[Aib$^{22,35}$]GLP-1-(7-37)yl($N^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{8,35}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{8,35}$,Lys$^{37}$]GLP-1-(7-37) amide where mPEGyl is polydisperse and has a Mw of approx 20 kDa, $N^{\alpha}$-[Aib$^{8,35}$]GLP-1-(7-37)yl(N$^{\epsilon}$-(3-(mPEGyl)propionyl))Lysine where mPEGyl is polydisperse and has a Mw of approx 20 kDa, $N^{\alpha}$-[Aib$^{8,35}$]GLP-1-(7-37)yl(N$^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{8,22}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{8,22}$,Lys$^{37}$]GLP-1-(7-37) amide where mPEGyl is polydisperse and has a Mw of approx 20 kDa, $N^{\alpha}$-[Aib$^{8,22}$]GLP-1-(7-37)yl(N$^{\epsilon}$-(3-(mPEGyl)propionyl))Lysine where mPEGyl is polydisperse and has a Mw of approx 20 kDa, $N^{\alpha}$-[Aib$^{8,22}$]GLP-1-(7-37)yl(N$^{\epsilon}$-(3-(mPEGyl)propionyl))Lysinamide where mPEGyl is polydisperse and has a Mw of approx 20 kDa, $N^{\epsilon 37}$-(3-(mPEGyl)propionyl)[Aib$^{8,22,35}$,Lys$^{37}$]GLP-1-(7-37) where mPEGyl is polydisperse and has a Mw of approx 20 kDa, $N^{\epsilon 37}$-(3-(mPEGyl)propionyl)[Aib$^{8,22,35}$,Lys$^{37}$]GLP-1-(7-37) amide where mPEGyl is polydisperse and has a Mw of approx 20 kDa, $N^{\alpha}$-[Aib$^{8,22,35}$]GLP-1-(7-37)yl(N$^{\epsilon}$-(3-(mPEGyl)propionyl))Lysine where mPEGyl is polydisperse and has a Mw of approx 20 kDa, $N^{\alpha}$-[Aib$^{8,22,35}$]GLP-1-(7-37)yl(N$^{\epsilon}$-(3-(mPEGyl)propionyl))Lysinamide where mPEGyl is polydisperse and has a Mw of approx 20 kDa, $N^{\alpha}$-[Aib$^{8}$,Arg$^{26,34}$]GLP-1-(7-37)yl(N$^{\epsilon}$-(3-(mPEGyl)propionyl))Lysine where mPEGyl is polydisperse and has a Mw of approx 20 kDa, $N^{\alpha}$-[Aib$^{8}$,Arg$^{26,34}$]GLP-1-(7-37)yl(N$^{\epsilon}$-(3-(mPEGyl)propionyl))Lysinamide where mPEGyl is polydisperse and has a Mw of approx 20 kDa $N^{\epsilon 36}$-(3-(mPEGyl)propionyl)[Aib$^{8}$,Arg$^{26,34}$,Lys$^{36}$]GLP-1-(7-37) where mPEGyl is polydisperse and has a Mw of approx 20 kDa, $N^{\epsilon 36}$-(3-(mPEGyl)propionyl)[Aib$^{8}$,Arg$^{26,34}$,Lys$^{36}$]GLP-1-(7-37) amide where mPEGyl is polydisperse and has a Mw of approx 20 kDa, $N^{\epsilon 34}$-(3-(mPEGyl)propionyl)[Aib$^{8}$,Lys$^{26}$,Lys$^{34}$]GLP-1-(7-37) where mPEGyl is polydisperse and has a Mw of approx 20 kDa, $N^{\epsilon 34}$-(3-(mPEGyl)propionyl)[Aib$^{8}$,Lys$^{26}$,Lys$^{34}$]GLP-1-(7-37) amide where mPEGyl is polydisperse and has a Mw of approx 20 kDa, $N^{\alpha}$-[Arg$^{26,34}$]GLP-1-(7-37)yl(N$^{\epsilon}$-(3-(mPEGyl)propionyl))Lysine where mPEGyl is polydisperse and has a Mw of approx 20 kDa, $N^{\alpha}$-[Arg$^{26,34}$]GLP-1-(7-37)yl(N$^{\epsilon}$-(3-(mPEGyl)propionyl))Lysinamide where mPEGyl is polydisperse and has a Mw of approx 20 kDa, $N^{\epsilon 36}$-(3-(mPEGyl)propionyl)[Arg$^{26,34}$,Lys$^{36}$]GLP-1-(7-37) where mPEGyl is polydisperse and has a Mw of approx 20 kDa, $N^{\epsilon 36}$-(3-(mPEGyl)propionyl)[Arg$^{26,34}$,Lys$^{36}$]GLP-1-(7-37) amide where mPEGyl is polydisperse and has a Mw of approx 20 kDa, $N^{\epsilon 34}$-(3-(mPEGyl)propionyl)[Lys$^{26}$,Lys$^{34}$]GLP-1-(7-37) where mPEGyl is polydisperse and has a Mw of approx 20 kDa, $N^{\epsilon 34}$-(3-(mPEGyl)propionyl)[Lys$^{26}$,Lys$^{34}$]GLP-1-(7-37) amide where mPEGyl is polydisperse and has a Mw of approx 20 kDa, $N^{\alpha}$-[Ala$^{8}$,Arg$^{26,34}$,]GLP-1-(7-37)yl(N$^{\epsilon}$-(3-(mPEGyl)propionyl))Lysine where mPEGyl is polydisperse and has a Mw of approx 20 kDa, $N^{\alpha}$-[Ala$^{8}$,Arg$^{26,34}$]GLP-1-(7-37)yl(N$^{\epsilon}$-(3-(mPEGyl)propionyl))Lysinamide where mPEGyl is polydisperse and has a Mw of approx 20 kDa, $N^{\epsilon 36}$-(3-(mPEGyl)propionyl)[Ala$^{8}$,Arg$^{26,34}$,Lys$^{36}$]GLP-1-(7-37) where mPEGyl is polydisperse and has a Mw of approx 20 kDa, $N^{\epsilon 36}$-(3-(mPEGyl)propionyl)[Ala$^{8}$,Arg$^{26,34}$,Lys$^{36}$]GLP-1-(7-37) amide where mPEGyl is polydisperse and has a Mw of approx 20 kDa, $N^{\epsilon 34}$-(3-(mPEGyl)propionyl)[Ala$^{8}$,Lys$^{26}$,Lys$^{34}$]GLP-1-(7-37) where mPEGyl is polydisperse and has a Mw of approx 20 kDa, $N^{\epsilon 34}$-(3-(mPEGyl)propionyl)[Ala$^{8}$,Lys$^{26}$,Lys$^{34}$]GLP-1-(7-37) amide where mPEGyl is polydisperse and has a Mw of approx 20 kDa, $N^{\epsilon 20}$-(3-(mPEGyl)propionyl)[Lys$^{20}$]Exendin-4-(1-39) amide where mPEGyl is polydisperse and has a Mw of approx 20 kDa, $N^{\epsilon 32}$-(3-(mPEGyl)propionyl)[Lys$^{32}$]Exendin-4-(1-39) amide where mPEGyl is polydisperse and has a Mw of approx 20 kDa, $N^{\epsilon 20}$-(3-(mPEGyl)propionyl)[Lys$^{20}$,Arg$^{12,27}$]Exendin-4-(1-39) amide where mPEGyl is polydisperse and has a Mw of approx 20 kDa, and $N^{\epsilon 32}$-(3-(mPEGyl)propionyl)[Lys$^{32}$,Arg$^{12,27}$]Exendin-4-(1-39) amide where mPEGyl is polydisperse and has a Mw of approx 20 kDa.

In another embodiment the compound according to the present invention is selected from the group consisting of $N^{\epsilon 37}$-(3-(mPEGyl)butanoyl)[Lys$^{37}$]GLP-1-(7-37) where mPEGyl is polydisperse and has a Mw of approx 30 kDa, $N^{\epsilon 37}$-(3-(mPEGyl)butanoyl)[Lys$^{37}$]GLP-1-(7-37) amide where mPEGyl is polydisperse and has a Mw of approx 30 kDa, GLP-1-(7-37)yl(N$^{\epsilon}$-(3-(mPEGyl)butanoyl))Lysine where mPEGyl is polydisperse and has a Mw of approx 30 kDa, GLP-1-(7-37)yl(N$^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{35}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{35}$,Lys$^{37}$]GLP-1-(7-37) amide where mPEGyl is polydisperse and has a Mw of approx 30 kDa, $N^{\alpha}$-[Aib$^{35}$]GLP-1-(7-37)yl(N$^{\epsilon}$-(3-(mPEGyl)butanoyl))Lysine where mPEGyl is polydisperse and has a Mw of approx 30 kDa, $N^{\alpha}$-[Aib$^{35}$]GLP-1-(7-37)yl(N$^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{22}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{22}$,Lys$^{37}$]GLP-1-(7-37) amide where mPEGyl is polydisperse and has a Mw of approx 30 kDa, $N^{\alpha}$-[Aib$^{22}$]GLP-1-(7-37)yl(N$^{\epsilon}$-(3-(mPEGyl)butanoyl))Lysine where mPEGyl is polydisperse and has a Mw of approx 30 kDa, $N^{\alpha}$-[Aib$^{22}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{8}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{8}$,Lys$^{37}$]GLP-1-(7-37) amide where mPEGyl is polydisperse and has a Mw of approx 30 kDa, $N^{\alpha}$-[Aib$^{8}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Aib$^{8}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{8,35}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{8,35}$,Lys$^{37}$]GLP-1-(7-37) amide where mPEGyl is polydisperse and has a Mw of approx 30 kDa, $N^{\alpha}$-[Aib$^{8,35}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Aib$^{8,35}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{22,35}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{22,35}$,Lys$^{37}$]GLP-1-(7-37) amide where mPEGyl is polydisperse and has a Mw of approx 30 kDa, $N^{\alpha}$-[Aib$^{22,35}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Aib$^{22,35}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{8,35}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{8,35}$,Lys$^{37}$]GLP-1-(7-37) amide where mPEGyl is polydisperse and has a Mw of approx 30 kDa, $N^{\alpha}$-[Aib$^{8,35}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Aib$^{8,35}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{8,22}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{8,22}$,Lys$^{37}$]GLP-1-(7-37) amide where mPEGyl is polydisperse and has a Mw of approx 30 kDa, $N^{\alpha}$-[Aib$^{8,22}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Aib$^{8,22}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 37}$-(3-(mPEGyl)butanoyl)[Aib$^{8,22,35}$,Lys$^{37}$]GLP-1-(7-37) where mPEGyl is polydisperse and has a Mw of approx 30 kDa, $N^{\epsilon 37}$-(3-(mPEGyl)butanoyl)[Aib$^{8,22,35}$,Lys$^{37}$]GLP-1-(7-37) amide where mPEGyl is polydisperse and has a Mw of approx 30 kDa, $N^{\alpha}$-[Aib$^{8,22,35}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Aib$^{8,22,35}$]GLP-1-(7-37)yl($N^{\epsilon}$-(3-(mPEGyl)butanoyl))Lysinamide where mPEGyl is polydisperse and has a Mw of approx 30 kDa, $N^{\alpha}$-[Aib$^{8}$,Arg$^{26,34}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Aib$^{8}$,Arg$^{26,34}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 36}$-(3-(mPEGyl)butanoyl)[Aib$^{8}$,Arg$^{26,34}$,Lys$^{36}$]GLP-1-(7-37) where mPEGyl is polydisperse and has a Mw of approx 30 kDa, $N^{\epsilon 36}$-(3-(mPEGyl)butanoyl)[Aib$^{8}$,Arg$^{26,34}$,Lys$^{36}$]GLP-1-(7-37) amide where mPEGyl is polydisperse and has a Mw of approx 30 kDa, $N^{\epsilon 34}$-(3-(mPEGyl)butanoyl)[Aib$^{8}$,Lys$^{26}$,Lys$^{34}$]GLP-1-(7-37) where mPEGyl is polydisperse and has a Mw of approx 30 kDa, $N^{\epsilon 34}$-(3-(mPEGyl)butanoyl)[Aib$^{8}$,Lys$^{26}$,Lys$^{34}$]GLP-1-(7-37) amide where mPEGyl is polydisperse and has a Mw of approx 30 kDa, $N^{\alpha}$-[Arg$^{26,34}$]GLP-1-(7-37)yl($N^{\epsilon}$-(3-(mPEGyl)butanoyl))Lysine where mPEGyl is polydisperse and has a Mw of approx 30 kDa, $N^{\alpha}$-[Arg$^{26,34}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 36}$-(3-(mPEGyl)butanoyl)[Arg$^{26,34}$,Lys$^{36}$]GLP-1-(7-37) where mPEGyl is polydisperse and has a Mw of approx 30 kDa, $N^{\epsilon 36}$-(3-(mPEGyl)butanoyl)[Arg$^{26,34}$,Lys$^{36}$]GLP-1-(7-37) amide where mPEGyl is polydisperse and has a Mw of approx 30 kDa, $N^{\epsilon 34}$-(3-(mPEGyl)butanoyl)[Lys$^{26}$,Lys$^{34}$]GLP-1-(7-37) where mPEGyl is polydisperse and has a Mw of approx 30 kDa, $N^{\epsilon 34}$-(3-(mPEGyl)butanoyl)[Lys$^{26}$,Lys$^{34}$]GLP-1-(7-37) amide where mPEGyl is polydisperse and has a Mw of approx 30 kDa, $N^{\alpha}$-[Ala$^{8}$,Arg$^{26,34}$,]GLP-1-(7-37)yl($N^{\epsilon}$-(3-(mPEGyl)butanoyl))Lysine where mPEGyl is polydisperse and has a Mw of approx 30 kDa, $N^{\alpha}$-[Ala$^{8}$,Arg$^{26,34}$]GLP-1-(7-37)yl($N^{\epsilon}$-(3-(mPEGyl)butanoyl))Lysinamide where mPEGyl is polydisperse and has a Mw of approx 30 kDa, $N^{\epsilon 36}$-(3-(mPEGyl)butanoyl)[Ala$^{8}$,Arg$^{26,34}$,Lys$^{36}$]GLP-1-(7-37) where mPEGyl is polydisperse and has a Mw of approx 30 kDa, $N^{\epsilon 36}$-(3-(mPEGyl)butanoyl)[Ala$^{8}$,Arg$^{26,34}$,Lys$^{36}$]GLP-1-(7-37) amide where mPEGyl is polydisperse and has a Mw of approx 30 kDa, $N^{\epsilon 34}$-(3-(mPEGyl)butanoyl)[Ala$^{8}$,Lys$^{26}$,Lys$^{34}$]GLP-1-(7-37) where mPEGyl is polydisperse and has a Mw of approx 30 kDa, $N^{\epsilon 34}$-(3-(mPEGyl)butanoyl)[Ala$^{8}$,Lys$^{26}$,Lys$^{34}$]GLP-1-(7-37) amide where mPEGyl is polydisperse and has a Mw of approx 30 kDa, $N^{\epsilon 20}$-(3-(mPEGyl)butanoyl)[Lys$^{20}$]Exendin-4-(1-39) amide where mPEGyl is polydisperse and has a Mw of approx 30 kDa, $N^{\epsilon 32}$-(3-(mPEGyl)butanoyl)[Lys$^{32}$]Exendin-4-(1-39) amide where mPEGyl is polydisperse and has a Mw of approx 30 kDa, $N^{\epsilon 20}$-(3-(mPEGyl)butanoyl)[Lys$^{20}$,Arg$^{12,27}$]Exendin-4-(1-39) amide where mPEGyl is polydisperse and has a Mw of approx 30 kDa, and $N^{\epsilon 32}$-(3-(mPEGyl)butanoyl)[Lys$^{32}$,Arg$^{12,27}$]Exendin-4-(1-39) amide where mPEGyl is polydisperse and has a Mw of approx 30 kDa.

In another embodiment the compound according to the present invention is selected from the group consisting of $N^{\epsilon 37}$-((2S)-2,6-di-(mPEGylcarbonylamino)hexanoyl) [Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl) [Lys$^{37}$]GLP-1-(7-37) amide where mPEGyl is polydisperse and has a Mw of approx 20 kDa, GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl) [Aib$^{35}$,Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl) [Aib$^{35}$,Lys$^{37}$]GLP-1-(7-37) amide where mPEGyl is polydisperse and has a Mw of approx 20 kDa, $N^{\alpha}$-[Aib$^{35}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{35}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl) [Aib$^{22}$,Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl) [Aib$^{22}$,Lys$^{37}$]GLP-1-(7-37) amide where mPEGyl is polydisperse and has a Mw of approx 20 kDa, $N^{\alpha}$-[Aib$^{22}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{22}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl)[Aib$^{8}$,Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl)[Aib$^{8}$,Lys$^{37}$]GLP-1-(7-37) amide where mPEGyl is polydisperse and has a Mw of approx 20 kDa, $N^{\alpha}$-[Aib$^{8}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{8}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl) [Aib$^{8,35}$,Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl) [Aib$^{8,35}$,Lys$^{37}$]GLP-1-(7-37) amide where mPEGyl is polydisperse and has a Mw of approx 20 kDa, $N^{\alpha}$-[Aib$^{8,35}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{8,35}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl) [Aib$^{22,35}$,Lys$^{37l}$$^{GLP}$-1-(7-37) where mPEGyl is polydisperse and has a Mw of approx 20 kDa, $N^{\epsilon 37}$-((2S)-2,6-di-(mPEGylcarbonylamino)hexanoyl) [Aib$^{22,35}$,Lys$^{37}$]GLP-1-(7-37) amide where mPEGyl is polydisperse and has a Mw of approx 20 kDa, $N^{\alpha}$-[Aib$^{22,35}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{22,35}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl) [Aib$^{8,35}$,Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl) [Aib$^{8,35}$,Lys$^{37}$]GLP-1-(7-37) amide where mPEGyl is polydisperse and has a Mw of approx 20 kDa, $N^{\alpha}$-[Aib$^{8,35}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{8,35}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl) [Aib$^{8,22}$,Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl) [Aib$^{8,22}$,Lys$^{37}$]GLP-1-(7-37) amide where mPEGyl is polydisperse and has a Mw of approx 20 kDa, $N^{\alpha}$-[Aib$^{8,22}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{8,22}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 37}$-((2S)-2,6-di-(mPEGylcarbonylamino)hexanoyl) [Aib$^{8,22,35}$,Lys$^{37}$]GLP-1-(7-37) where mPEGyl is polydisperse and has a Mw of approx 20 kDa, $N^{\epsilon 37}$-((2S)-2,6-di-(mPEGylcarbonylamino)hexanoyl) [Aib$^{8,22,35}$,Lys$^{37}$]GLP-1-(7-37) amide where mPEGyl is polydisperse and has a Mw of approx 20 kDa, $N^{\alpha}$-[Aib$^{8,22,35}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{8,22,35}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\alpha}$-[Aib$^{8}$,Arg$^{28,34}$]GLP-1-(7-37)yl(N$^{\epsilon}$-((2S)-2,6-di-(mPEGylcarbonylamino)hexanoyl))Lysine where mPEGyl is polydisperse and has a Mw of approx 20 kDa, $N^{\alpha}$-[Aib$^{8}$,Arg$^{28,34}$]GLP-1-(7-37)yl(N$^{\epsilon}$-((2S)-2,6-di-(mPEGylcarbonylamino)hexanoyl))Lysinamide where mPEGyl is polydisperse and has a Mw of approx 20 kDa, $N^{\epsilon 36}$-((2S)-2,6-di-(mPEGylcarbonylamino)hexanoyl)[Aib$^{8}$,Arg$^{26,34}$,Lys$^{36}$]GLP-1-(7-37) where mPEGyl is polydisperse and has a Mw of approx 20 kDa, $N^{\epsilon 36}$-((2S)-2,6-di-(mPEGylcarbonylamino)hexanoyl)[Aib$^{8}$,Arg$^{26,34}$,Lys$^{36}$]GLP-1-(7-37) amide where mPEGyl is polydisperse and has a Mw of approx 20 kDa, $N^{\epsilon34}$-((2S)-2,6-di-(mPEGylcarbonylamino)hexanoyl)[Aib$^8$, Lys$^{28}$,Lys$^{34}$]GLP-1-(7-37) where mPEGyl is polydisperse and has a Mw of approx 20 kDa, $N^{\epsilon34}$-((2S)-2,6-di-(mPEGylcarbonylamino)hexanoyl)[Aib$^8$, Lys$^{28}$,Lys$^{34}$]GLP-1-(7-37) amide where mPEGyl is polydisperse and has a Mw of approx 20 kDa, $N^{\alpha}$-[Arg$^{28,34}$]GLP-1-(7-37)yl($N^{\epsilon}$-((2S)-2,6-di-(mPEGylcarbonylamino)hexanoyl))Lysine where mPEGyl is polydisperse and has a Mw of approx 20 kDa, $N^{\alpha}$-[Arg$^{28,34}$]GLP-1-(7-37)yl($N^{\epsilon}$-((2S)-2,6-di-(mPEGylcarbonylamino)hexanoyl))Lysinamide where mPEGyl is polydisperse and has a Mw of approx 20 kDa, $N^{\epsilon36}$-((2S)-2,6-di-(mPEGylcarbonylamino)hexanoyl)[Arg$^{26,34}$,Lys$^{36}$]GLP-1-(7-37) where mPEGyl is polydisperse and has a Mw of approx 20 kDa, $N^{\epsilon36}$-((2S)-2,6-di-(mPEGylcarbonylamino)hexanoyl)[Arg$^{26,34}$,Lys$^{36}$]GLP-1-(7-37) amide where mPEGyl is polydisperse and has a Mw of approx 20 kDa, $N^{\epsilon34}$-((2S)-2,6-di-(mPEGylcarbonylamino)hexanoyl)[Lys$^{26}$,Lys$^{34}$]GLP-1-(7-37) where mPEGyl is polydisperse and has a Mw of approx 20 kDa, $N^{\epsilon34}$-((2S)-2,6-di-(mPEGylcarbonylamino)hexanoyl)[Lys$^{26}$,Lys$^{34}$]GLP-1-(7-37) amide where mPEGyl is polydisperse and has a Mw of approx 20 kDa, $N^{\alpha}$-[Ala$^8$,Arg$^{26,34}$,]GLP-1-(7-37)yl($N^{\epsilon}$-((2S)-2,6-di-(mPEGylcarbonylamino)hexanoyl))Lysine where mPEGyl is polydisperse and has a Mw of approx 20 kDa, $N^{\alpha}$-[Ala$^8$,Arg$^{26,34}$]GLP-1-(7-37)yl($N^{\epsilon}$-((2S)-2,6-di-(mPEGylcarbonylamino)hexanoyl))Lysinamide where mPEGyl is polydisperse and has a Mw of approx 20 kDa, $N^{\epsilon36}$-((2S)-2,6-di-(mPEGylcarbonylamino)hexanoyl)[Ala$^8$, Arg$^{26,34}$,Lys$^{36}$]GLP-1-(7-37) where mPEGyl is polydisperse and has a Mw of approx 20 kDa, $N^{\epsilon36}$-((2S)-2,6-di-(mPEGylcarbonylamino)hexanoyl)[Ala$^8$, Arg$^{26,34}$,Lys$^{36}$]GLP-1-(7-37) amide where mPEGyl is polydisperse and has a Mw of approx 20 kDa, $N^{\epsilon34}$-((2S)-2,6-di-(mPEGylcarbonylamino)hexanoyl)[Ala$^8$, Lys$^{26}$,Lys$^{34}$]GLP-1-(7-37) where mPEGyl is polydisperse and has a Mw of approx 20 kDa, $N^{\epsilon34}$-((2S)-2,6-di-(mPEGylcarbonylamino)hexanoyl)[Ala$^8$, Lys$^{26}$,Lys$^{34}$]GLP-1-(7-37) amide where mPEGyl is polydisperse and has a Mw of approx 20 kDa, $N^{\epsilon20}$-((2S)-2,6-di-(mPEGylcarbonylamino)hexanoyl)[Lys$^{20}$]Exendin-4-(1-39) amide where mPEGyl is polydisperse and has a Mw of approx 20 kDa, $N^{\epsilon32}$-((2S)-2,6-di-(mPEGylcarbonylamino)hexanoyl)[Lys$^{32}$]Exendin-4-(1-39) amide where mPEGyl is polydisperse and has a Mw of approx 20 kDa, $N^{\epsilon20}$-((2S)-2,6-di-(mPEGylcarbonylamino)hexanoyl)[Lys$^{20}$,Arg$^{12,27}$]Exendin-4-(1-39) amide where mPEGyl is polydisperse and has a Mw of approx 20 kDa, and $N^{\epsilon32}$-((2S)-2,6-di-(mPEGylcarbonylamino)hexanoyl)[Lys$^{32}$,Arg$^{12,27}$]Exendin-4-(1-39) amide where mPEGyl is polydisperse and has a Mw of approx 20 kDa.

In another embodiment the compound according to the present invention is selected from the group consisting of $N^{\epsilon37}$-(4-(1,3-bis(mPEGylethylaminocarbonyloxy)prop-2-yloxy)butanoyl)[Lys$^{37}$]GLP-1-(7-37) where mPEGyl is polydisperse and has a Mw of approx 20 kDa, $N^{\epsilon37}$-(4-(1,3-bis(mPEGylethylaminocarbonyloxy)prop-2-yloxy)butanoyl)[Lys$^{37}$]GLP-1-(7-37) amide where mPEGyl is polydisperse and has a Mw of approx 20 kDa, GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{35}$,Lys$^{37}$]GLP-1-(7-37) where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{35}$,Lys$^{37}$]GLP-1-(7-37) amide where mPEGyl is polydisperse and has a Mw of approx 20 kDa, $N^{\alpha}$-[Aib$^{35}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{35}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{22}$,Lys$^{37}$]GLP-1-(7-37) where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{22}$,Lys$^{37}$]GLP-1-(7-37) amide where mPEGyl is polydisperse and has a Mw of approx 20 kDa, $N^{\alpha}$-[Aib$^{22}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{22}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^8$,Lys$^{37}$]GLP-1-(7-37) where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^8$,Lys$^{37}$]GLP-1-(7-37) amide where mPEGyl is polydisperse and has a Mw of approx 20 kDa, $N^{\alpha}$-[Aib$^8$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^8$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{8,35}$,Lys$^{37}$]GLP-1-(7-37) where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{8,35}$,Lys$^{37}$]GLP-1-(7-37) amide where mPEGyl is polydisperse and has a Mw of approx 20 kDa, $N^{\alpha}$-[Aib$^{8,35}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{8,35}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{22,35}$,Lys$^{37}$]GLP-1-(7-37) where mPEGyl is polydisperse and has a Mw of approx 20 kDa, $N^{\epsilon37}$-(4-(1,3-bis(mPEGylethylaminocarbonyloxy)prop-2-yloxy)butanoyl)[Aib$^{22,35}$,Lys$^{37}$]GLP-1-(7-37) amide where mPEGyl is polydisperse and has a Mw of approx 20 kDa, $N^{\alpha}$-[Aib$^{22,35}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{22,35}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon 37}$-(4-(1,3-bis(mPEGylethylaminocarbonyloxy)prop-2-yloxy)butanoyl)[Aib$^{8,35}$,Lys$^{37}$]GLP-1-(7-37) where mPEGyl is polydisperse and has a Mw of approx 20 kDa, $N^{\epsilon 37}$-(4-(1,3-bis(mPEGylethylaminocarbonyloxy)prop-2-yloxy)butanoyl)[Aib$^{8,35}$,Lys$^{37}$]GLP-1-(7-37) amide where mPEGyl is polydisperse and has a Mw of approx 20 kDa, $N^{\alpha}$-[Aib$^{8,35}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{8,35}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon 37}$-(4-(1,3-bis(mPEGylethylaminocarbonyloxy)prop-2-yloxy)butanoyl)[Aib$^{8,22}$,Lys$^{37}$]GLP-1-(7-37) where mPEGyl is polydisperse and has a Mw of approx 20 kDa, $N^{\epsilon 37}$-(4-(1,3-bis(mPEGylethylaminocarbonyloxy)prop-2-yloxy)butanoyl)[Aib$^{8,22}$,Lys$^{37}$]GLP-1-(7-37) amide where mPEGyl is polydisperse and has a Mw of approx 20 kDa, $N^{\alpha}$-[Aib$^{8,22}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{8,22}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon 37}$-(4-(1,3-bis(mPEGylethylaminocarbonyloxy)prop-2-yloxy)butanoyl)[Aib$^{8,22,35}$,Lys$^{37}$]GLP-1-(7-37) where mPEGyl is polydisperse and has a Mw of approx 20 kDa, $N^{\epsilon 37}$-(4-(1,3-bis(mPEGylethylaminocarbonyloxy)prop-2-yloxy)butanoyl)[Aib$^{8,22,35}$,Lys$^{37}$]GLP-1-(7-37) amide where mPEGyl is polydisperse and has a Mw of approx 20 kDa, $N^{\alpha}$-[Aib$^{8,22,35}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{8,22,35}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\alpha}$-[Aib$^{8}$,Arg$^{26,34}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Aib$^{8}$,Arg$^{26,34}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon 36}$-(4-(1,3-bis(mPEGylethylaminocarbonyloxy)prop-2-yloxy)butanoyl)[Aib$^{8}$,Arg$^{26,34}$,Lys$^{36}$]GLP-1-(7-37) where mPEGyl is polydisperse and has a Mw of approx 20 kDa, $N^{\epsilon 36}$-(4-(1,3-bis(mPEGylethylaminocarbonyloxy)prop-2-yloxy)butanoyl)[Aib$^{8}$,Arg$^{26,34}$,Lys$^{36}$]GLP-1-(7-37) amide where mPEGyl is polydisperse and has a Mw of approx 20 kDa, $N^{\epsilon 34}$-(4-(1,3-bis(mPEGylethylaminocarbonyloxy)prop-2-yloxy)butanoyl)[Aib$^{8}$,Lys$^{26}$,Lys$^{34}$]GLP-1-(7-37) where mPEGyl is polydisperse and has a Mw of approx 20 kDa, $N^{\epsilon 34}$-(4-(1,3-bis(mPEGylethylaminocarbonyloxy)prop-2-yloxy)butanoyl)[Aib$^{8}$,Lys$^{26}$,Lys$^{34}$]GLP-1-(7-37) amide where mPEGyl is polydisperse and has a Mw of approx 20 kDa, $N^{\alpha}$-[Arg$^{26,34}$]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Arg$^{26,34}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon 36}$-(4-(1,3-bis(mPEGylethylaminocarbonyloxy)prop-2-yloxy)butanoyl)[Arg$^{26,34}$,Lys$^{36}$]GLP-1-(7-37) where mPEGyl is polydisperse and has a Mw of approx 20 kDa, $N^{\epsilon 36}$-(4-(1,3-bis(mPEGylethylaminocarbonyloxy)prop-2-yloxy)butanoyl)[Arg$^{26,34}$,Lys$^{36}$]GLP-1-(7-37) amide where mPEGyl is polydisperse and has a Mw of approx 20 kDa, $N^{\epsilon 34}$-(4-(1,3-bis(mPEGylethylaminocarbonyloxy)prop-2-yloxy)butanoyl)[Lys$^{26}$,Lys$^{34}$]GLP-1-(7-37) where mPEGyl is polydisperse and has a Mw of approx 20 kDa, $N^{\epsilon 34}$-(4-(1,3-bis(mPEGylethylaminocarbonyloxy)prop-2-yloxy)butanoyl)[Lys$^{26}$,Lys$^{34}$]GLP-1-(7-37) amide where mPEGyl is polydisperse and has a Mw of approx 20 kDa, $N^{\alpha}$-[Ala$^{8}$,Arg$^{26,34}$,]GLP-1-(7-37)yl($N^{\epsilon}$-(4-(1,3-bis(mPEGylethylaminocarbonyloxy)prop-2-yloxy)butanoyl))Lysine where mPEGyl is polydisperse and has a Mw of approx 20 kDa, $N^{\alpha}$-[Ala$^{8}$,Arg$^{26,34}$]GLP-1-(7-37)yl($N^{\epsilon}$-(4-(1,3-bis(mPEGylethylaminocarbonyloxy)prop-2-yloxy)butanoyl))Lysinamide where mPEGyl is polydisperse and has a Mw of approx 20 kDa, $N^{\epsilon 36}$-(4-(1,3-bis(mPEGylethylaminocarbonyloxy)prop-2-yloxy)butanoyl)[Ala$^{8}$,Arg$^{26,34}$,Lys$^{36}$]GLP-1-(7-37) where mPEGyl is polydisperse and has a Mw of approx 20 kDa, $N^{\epsilon 36}$-(4-(1,3-bis(mPEGylethylaminocarbonyloxy)prop-2-yloxy)butanoyl)[Ala$^{8}$,Arg$^{26,34}$,Lys$^{36}$]GLP-1-(7-37) amide where mPEGyl is polydisperse and has a Mw of approx 20 kDa, $N^{\epsilon 34}$-(4-(1,3-bis(mPEGylethylaminocarbonyloxy)prop-2-yloxy)butanoyl)[Ala$^{8}$,Lys$^{26}$,Lys$^{34}$]GLP-1-(7-37) where mPEGyl is polydisperse and has a Mw of approx 20 kDa, $N^{\epsilon 34}$-(4-(1,3-bis(mPEGylethylaminocarbonyloxy)prop-2-yloxy)butanoyl)[Ala$^{8}$,Lys$^{26}$,Lys$^{34}$]GLP-1-(7-37) amide where mPEGyl is polydisperse and has a Mw of approx 20 kDa, $N^{\epsilon 20}$-(4-(1,3-bis(mPEGylethylaminocarbonyloxy)prop-2-yloxy)butanoyl)[Lys$^{20}$]Exendin-4-(1-39) amide where mPEGyl is polydisperse and has a Mw of approx 20 kDa, $N^{\epsilon 32}$-(4-(1,3-bis(mPEGylethylaminocarbonyloxy)prop-2-yloxy)butanoyl)[Lys$^{32}$]Exendin-4-(1-39) amide where mPEGyl is polydisperse and has a Mw of approx 20 kDa, $N^{\epsilon 20}$-(4-(1,3-bis(mPEGylethylaminocarbonyloxy)prop-2-yloxy)butanoyl)[Lys$^{20}$,Arg$^{12,27}$]Exendin-4-(1-39) amide where mPEGyl is polydisperse and has a Mw of approx 20 kDa, $N^{\epsilon 32}$-(4-(1,3-bis(mPEGylethylaminocarbonyloxy)prop-2-yloxy)butanoyl)[Lys$^{32}$,Arg$^{12,27}$]Exendin-4-(1-39) amide where mPEGyl is polydisperse and has a Mw of approx 20 kDa, The compounds of the present invention can be produced by classical peptide synthesis, e.g. solid phase peptide synthesis using t-Boc or Fmoc chemistry or other well established techniques, see e.g. Green and Wuts, "Protecting Groups in Organic Synthesis", John Wiley & Sons, 1999.

These methods are preferred when the insulinotropic agent is a peptide comprising non-natural amino acid residues.

When the insulinotropic agent is a polypeptide comprising only amino acid residues encoded by the genetic code, the polypeptides can also be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture and then derivatized to the compound of formula (I).

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration. For extracellular products the proteinaceous components of the supernatant are isolated by filtration, column chromatography or precipitation, e.g. microfiltration, ultrafiltration, isoelectric precipitation, purification by a variety of chromatographic procedures, e.g. ion exchange chromatography, hydrophobic interaction chromatography, gel filtration chromatography, affinity chromatography, or the like, dependent on the type of polypeptide in question. For intracellular or periplasmic products the cells isolated from the culture medium are disintegrated or permeabilised and extracted to recover the product polypeptide or precursor thereof.

The DNA sequence encoding the therapeutic polypeptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoramidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the polypeptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the polypeptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate. For large scale manufacture the selectable marker preferably is not antibiotic resistance, e.g. antibiotic resistance genes in the vector are preferably excised when the vector is used for large scale manufacture. Methods for eliminating antibiotic resistance genes from vectors are known in the art, see e.g. U.S. Pat. No. 6,358,705 which is incorporated herein by reference.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

Pharmaceutical compositions containing a compound according to the present invention may be prepared by conventional techniques, e.g. as described in *Remington's Pharmaceutical Sciences,* 1985 or in *Remington: The Science and Practice of Pharmacy,* 19$^{th}$ edition, 1995.

One object of the present invention is to provide a pharmaceutical formulation comprising a compound according to the present invention which is present in a concentration from about 0.1 mg/ml to about 25 mg/ml, and wherein said formulation has a pH from 2.0 to 10.0. The formulation may further comprise a buffer system, preservative(s), isotonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 2.0 to about 10.0.

In another embodiment of the invention the pH of the formulation is from about 7.0 to about 9.5. In another embodiment of the invention the pH of the formulation is from about 3.0 to about 7.0. In another embodiment of the invention the pH of the formulation is from about 5.0 to about 7.5. In another embodiment of the invention the pH of the formulation is from about 7.5 to about 9.0. In another embodiment of the invention the pH of the formulation is from about 7.5 to about 8.5. In another embodiment of the invention the pH of the formulation is from about 6.0 to about 7.5. In another embodiment of the invention the pH of the formulation is from about 6.0 to about 7.0.

In another embodiment of the invention the pH of the formulation is from about 3.0 to about 9.0, and said pH is at least 2.0 pH units from the isoelectric pH of compound of the present invention.

In a further embodiment of the invention the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thimerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof.

In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a $C_4$-$C_8$ hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabiliser. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or DL isomer) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include S-ethyl homocysteine and S-butyl homocysteine and suitable cystein analogues include S-methyl-L cystein. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphur containing amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabiliser selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lecitins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)- derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, Nα-acylated derivatives of lysine, arginine or histidine, or side-chain acylated derivatives of lysine or arginine, Nα-acylated derivatives of dipeptides comprising any combination of lysine, arginine or histidine and a neutral or acidic amino acid, Nα-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quarternary ammonium bases) (e.g. cetyl-trimethylammonium bromide, cetylpyridinium chloride), non-ionic surfactants (eg. dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

In one aspect the present invention relates to a pharmaceutical composition comprising a compound according to Formula (I), and a pharmaceutically acceptable excipient.

In one embodiment the pharmaceutical composition is suited for pulmonary administration.

In another aspect the present invention relates to the use of a compound of formula (I) for the preparation of a pulmonary medicament.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the compound, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenization, encapsulation, spray drying, microencapsulation, coacervation, phase separation, solvent evaporation to produce microspheres, extrusion and supercritical fluid processes. General reference is made to Handbook of Pharmaceutical Controlled Release (Wise, D. L., ed.

Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the compound according to the present invention in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound according to the present invention is stable for more than 6 weeks of usage and for more than 3 years of storage.

In another embodiment of the invention the pharmaceutical formulation comprising the compound according to the present invention is stable for more than 4 weeks of usage and for more than 3 years of storage.

In a further embodiment of the invention the pharmaceutical formulation comprising the compound according to the present invention is stable for more than 4 weeks of usage and for more than two years of storage.

In an even further embodiment of the invention the pharmaceutical formulation comprising the compound is stable for more than 2 weeks of usage and for more than two years of storage.

In another aspect the present invention relates to the use of a compound according to the invention for the preparation of a medicament.

In one embodiment a compound according to the invention is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

In another embodiment a compound according to the invention is used for the preparation of a medicament for delaying or preventing disease progression in type 2 diabetes.

In another embodiment a compound according to the invention is used for the preparation of a medicament for decreasing food intake, decreasing β-cell apoptosis, increasing β-cell function and β-cell mass, and/or for restoring glucose sensitivity to β-cells.

The treatment with a compound according to the present invention may also be combined with combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists.

It should be understood that any suitable combination of the compounds according to the invention with one or more of the above-mentioned compounds and optionally one or more further pharmacologically active substances are considered to be within the scope of the present invention.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Abbreviations Used:
r.t retention time
TFE trifluoroethanol
DIEA diisopropylethylamine
$H_2O$ water
$CH_3CN$ acetonitrile
DMF NN dimethylformamide
HBTU 2-(1H-Benzotriazol-1-yl-)-1,1,3,3 tetramethyluronium hexafluorophosphate
HATU O-(7-Azabenzotriazol-1-yl)-N,N,N',N'-Tetramethyluronium Hexafluorophosphate
ImPr 3-(1-Imidazol-4-yl)-propionyl
Adoc 1-Adamantyloxycarbonyl
Fmoc 9 H-fluoren-9-ylmethoxycarbonyl
Boc tert butyloxycarbonyl
OtBu tert butyl ester
tBu tert butyl
Trt triphenylmethyl
Pmc 2,2,5,7,8-Pentamethyl-chroman-6-sulfonyl
Dde 1-(4,4-Dimethyl-2,6-dioxocyclohexylidene)ethyl
ivDde 1-(4,4-Dimethyl-2,6-dioxocyclohexylidene)-3-Methylbutyl
DCM dichloromethane
TIS triisopropylsilane)
TFA: trifluoroacetic acid
$Et_2O$: diethylether
NMP 1-Methyl-pyrrolidin-2-one
Aib α-aminoisobutyric acid
Analysis HPLC analysis by the methods A1, B1 and B6 was performed on a Waters 2690 Separation Module equipped with a Waters 996 diode array detector. A Vydac 218TP54 4.6 mm×250 mm 5 μm C-18 silica column (The Separations Group, Hesperia) was used and detection was by UV at 214 nm, 254 nm, 280 nm and 301 nm.

HPLC analysis by the method 01_B4_2 was performed on a Waters 600S system fitted with a Waters 996 diode array detector. A Symmetry300 C18, 5 μm, 3.9 mm×150 mm column (Waters) was used and detection was by UV at 214 nm and 254 nm.

In method A1 the column was equilibrated with 0.05 M $NH_4SO_4$ pH 3.5 and eluted by a gradient of 0 to 60% $CH_3CN$ in 0.05 M $(NH_4)_2SO_4$ pH 3.5 over 50 min at 42° C., with a flow of 0.5 ml/min.

In method B1 the column was equilibrated with 0.1% TFA/$H_2O$ and eluted by a gradient of 0 to 60% $CH_3CN$ against 0.1% TFA/$H_2O$ over 50 min at 42° C., with a flow of 0.5 ml/min.

In method B6 the column was equilibrated with 0.1% TFA/$H_2O$ and eluted by a gradient of 0 to 90% $CH_3CN$ against 0.1% TFA/$H_2O$ over 50 min at 42° C., with a flow of 0.5 ml/min.

In method 01_B4_2 the column was equilibrated with 5% acetonitrile in water with 0.05% TFA and eluted by a gradient of 5 to 65% $CH_3CN$ against 0.05% TFA/$H_2O$ over 15 min at 42° C., with a flow of 1 ml/min.

Protein amount was calculated by comparing the UV detector response of the sample with the detector response from at of from a hGH standard for which the amount has been determined by amino acid analysis.

LC-MS analysis was performed on a PE-Sciex API 100 mass spectrometer equipped with two Perkin Elmer Series 200 Micropumps, a Perkin Elmer Series 200 autosampler, a Applied Biosystems 785A UV detector and a Sedex 75 Evaporative Light scattering detector. A Waters Xterra 3.0 mm×50 mm 5μ C-18 silica column was eluted at 1.5 ml/min at room temperature. It was equilibrated with 5% CH$_3$CN/ 0.1% TFA/H$_2$O and eluted for 1.0 min with 5% CH$_3$CN/ 0.1% TFA/H$_2$O and then with a linear gradient to 90% CH$_3$CN/0.1% TFA/H$_2$O over 7 min. Detection was by UV detection at 214 nm and Evaporative light Scattering. A fraction of the column eluate was introduced into the ion-spray interface of a PE-Sciex API 100 mass spectrometer. The mass range 300-2000 amu was scanned every 2 seconds during the run.

Maldi TOF MS analysis was performed on a Bruker Autoflex instrument in linear mode. Samples a prepared by the thin layer dried droplet method using α-cyano-4-hydroxycinnamic acid as the matrix.

Example 1

Preparation of N$^{\epsilon 37}$-(3-(mPEGyl)propionyl)[Aib$^{8,22,}$ $_{35}$,Lys$^{37}$]GLP-1(7-37) amide wherein mPEGyl is polydisperse and has a molecular weight of approximately 2 kDa

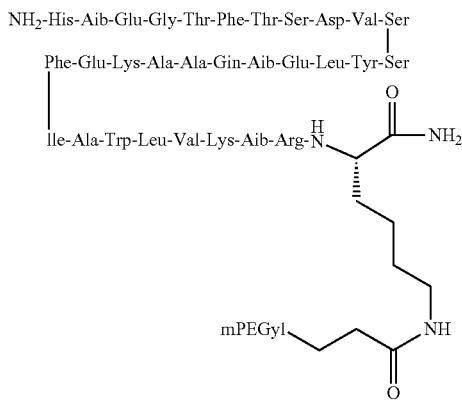

1.a Synthesis of the Protected Peptidyl Resin.

Boc-His(Boc)-Aib-Glu(OtBu)-Gly-Thr(tBu)-Phe-Thr (tBu)-Ser(tBu)-Asp(OtBu)-Val-Ser(tBu)-Ser(tBu)-Tyr (tBu)-Leu-Glu(OtBu)-Aib-Gln(Trt)-Ala-Ala-Lys(Boc)-Glu (OtBu)-Phe-Ile-Ala-Trp(Boc)-Leu-Val-Lys(Boc)-Aib-Arg (Pmc)-Lys(Dde)-Rink amide resin was prepared according to the Fmoc strategy on an Applied Biosystems 433A peptide synthesizer in 0.25 mmol scale using the manufacturer supplied FastMoc UV protocols which employ HBTU mediated couplings in NMP, and UV monitoring of the deprotection of the Fmoc protection group. To improve the coupling efficiency, Aib residues and residues following Aib, these residues were coupled using HATU instead of HBTU as the coupling reagent. The starting resin (438 mg) used for the synthesis was 4-(2',4'-Dimethoxyphenyl-Fmoc-aminomethyl)-phenoxy resin (Rink amide resin) (Merck Biosciences GmbH, Germany. cat. #: 01-12-0013) with a substitution capacity of 0.57 mmol/g. The protected amino acid derivatives used were (2S)-6-[1-(4,4-Dimethyl-2,6-dioxocyclohexylidene)-ethylamino]-2-(9H-fluoren-9-ylmethoxycarbonylamino)-hexanoic acid (Fmoc-Lys(Dde)-OH), Fmoc-Arg (Pmc)-OH, Fmoc-Aib-OH, Fmoc-Lys(Boc)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Gln(Trt)-OH, Fmoc-Tyr(tBu)-OH, Fmoc-Ser(tBu)-OH, Fmoc-Asp(OtBu)-OH, Fmoc-Thr(tBu)-OH, Fmoc-Gly-OH and Boc-His(Boc)-OH The yield was 1.37 g of dry peptidyl resin.

1.b Characterisation of the Peptidyl Resin.

The resin was characterized by cleaving off the crude peptide from 50 mg of this resin by treating it for 2 hours with a mixture of 14 μl TIS, 14 μl H$_2$O and 0.5 ml TFA. The resin was removed by filtration and the crude peptide was isolated by precipitation and wash with Et$_2$O. HPLC and LC-MS analysis was performed on the dry precipitate.

Analytical Results:

| Analytical method | Result |
|---|---|
| HPLC A1 | r.t.: 37.41 min., |
| LC-MS | r.t. 3.48 min., Mass for (M + 3H$^+$)/3: 1221.3 Da, (calc.: 1220 Da) |

1.c Deprotection of Dde

The protected peptidyl resin resulting from (1.a) (1.35 g, 250 μmol) was washed in NMP:DCM 1:1 (15 ml) twice. A freshly prepared solution of hydrazine hydrate 2% in NMP (20 ml) was added. The reaction mixture was shaken for 12 min at room temperature, and then filtered. The hydrazine treatment was repeated twice. After this the resin was washed extensively with NMP, DCM and NMP.

1.d Pegylation

The Dde deprotected resin was suspended in NMP (20 ml). 3-(mPEGyl)propionic acid 2,5-dioxo-pyrrolidin-1-yl ester (2.0 g, 1 mmol, 4 eq.) and DIEA (344 μl, 2 mmol, 8 eq.) was added and the suspension was shaken overnight. Then the resin was isolated by filtration and washed extensively with NMP, DCM, 2-propanol, methanol and Et$_2$O and dried in vacuo.

1.e Cleavage of the Product

The resin from 1.d was stirred for 3 h at room temperature with a mixture of 350 μl TIS, 350 μl H$_2$O and 14 ml TFA. The resin was removed by filtration and washed with 3 ml TFA. The collected filtrates were concentrated in vacuo. to 5 ml and the crude product was precipitated by addition of 40 ml Et$_2$O followed by centrifugation. The pellet was washed with 40 ml Et$_2$O two times and then air dried.

Results from HPLC of the dry precipitate:

| Analytical method | Result |
|---|---|
| HPLC A1 | r.t: 36.15 min., |
| HPLC B6 | r.t.: 28.573 min. estimated purity: 64% |

1.f Purification of Product.

The crude peptide was dissolved in H$_2$O/AcOH (40:4) (40 ml) and purified by semipreparative HPLC in 2 runs on a 25 mm×250 mm column packed with 7μ C-18 silica. The column was eluted with a gradient of CH$_3$CN from 40 to 62% against 0.1% TFA/H$_2$O at 10 ml/min at a temperature of 40° C. for 47 min. The peptide containing fractions are collected, diluted with 3 volumes of H$_2$O and lyophilized. The final product obtained was characterized by HPLC.

| Analytical method | Result |
|---|---|
| HPLC A1 | r.t: 36.15 min., |

Example 2

$N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 5 kDa

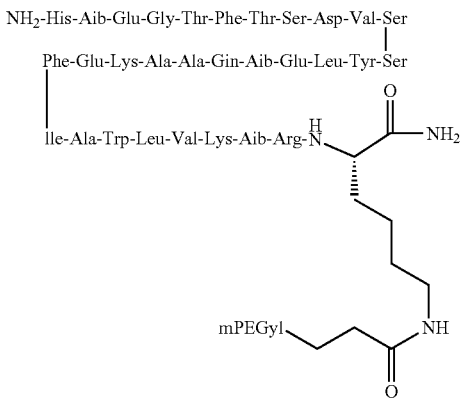

2.a Synthesis of the Protected Peptidyl Resin

The protected peptidyl resin Boc-His(Boc)-Aib-Glu (OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Aib-Gln(Trt)-Ala-Ala-Lys(Boc)-Glu(OtBu)-Phe-Ile-Ala-Trp(Boc)-Leu-Val-Lys(Boc)- Aib-Arg(Pmc)-Lys(Dde)-2-Chlorotrityl resin was synthesized using the procedures in example 1.a. with the exception that the starting resin was 337 mg of (2S)-6-[1-(4,4-Dimethyl-2,6-dioxocyclohexylidene)ethylamino]-2-(((9H-fluoren-9-yl)methoxycarbonyl)amino) hexanoyl 2-Chlorotrityl resin (Fmoc-Lys(Dde)-2-ClTrt resin). This Fmoc-Lys(Dde)-2-ClTrt resin was prepared by suspending 1 g of 2-Chlorotrityl chloride resin (Bachem, Switzerland. cat. #: D-1965), having a substitution capacity of 1.15 mmol/g in a mixture of 10 ml DCM and 100 μl DMF. To this was added 533 mg Fmoc-Lys(Dde)-OH (Merck Biosciences, Germany cat. #04-12-1121) and 684 μl DIEA and the mixture was stirred for 2 hours. The resin was isolated by filtration and then washed three times with 10 ml of DCM/MeOH/DIEA 17:2:1, three times with 10 ml DCM, two times with 10 ml NMP, two times with 10 ml DCM and then finally dried in vacuo. The synthesis resulted in approximately 1.2 g of protected peptidyl resin (air dried).

2.b Deprotection of Dde and Cleavage of Protected Peptide.

1.0 g of the protected peptidyl resin from 2.a was treated with 25 ml 2% hydrazine hydrate in DMF for 25 min and the resin was isolated by filtration. This was repeated further two times and after this the resin was thoroughly washed sequentially with DMF, DCM, 2-propanol, methanol Et$_2$O ether and then dried in vacuo.

This resin which was characterized as in example 1.b. analytical results:

| Analytical method | Result |
|---|---|
| HPLC A1 | r.t.: 41.12 min., |
| HPLC B6 | r.t.: 29.89 min. |
| LC-MS | r.t. 3.18 min., Mass for (M + 3H$^+$)/3: 1166.6 Da, (calc.: 1166.6 Da) |

The dry resin was stirred with 25 ml of a mixture of Acetic acid/TFE/DCM 1:1:3 for 2 h and then filtered and washed thoroughly with further 25 ml of this mixture. The pooled filtrates were concentrated to an oil in vacuo. and the oil was stripped 5 times with heptane to remove residual acetic acid.

2.c Pegylation and Final Deprotection.

To 100 mg of crude protected peptide from 2.b was dissolved in 1 ml TFE at 45° C. and 8.5 μl DIEA was added. A solution of 100 mg mPEG-5000-SPA (mPEG-SPA m.w. 5.000 Lot. PT-09B-12, Shearwater, Ala., USA) in 100 μl H$_2$O and 900 μl NMP was added and the mixture was stirred overnight at r.t. After this 48 ml Et$_2$O was added and the precipitate was collected and washed two times 50 ml Et$_2$O and dried in vacuo. The dried material was then stirred for 1 h. with a mixture of 2 ml TFA, 50 μl TIS and 50 μl H$_2$O and the crude pegylated peptide was isolated by precipitation with 50 ml Et$_2$O and washed three times with 50 ml Et$_2$O and then dried in vacuo. The crude peptide was dissolved in 20 ml H$_2$O and characterized as follows:

| Analytical method | Result |
|---|---|
| HPLC A1 | r.t.: 41.41 min. |
| HPLC B6 | r.t.: 30.06 min. |

2.d Purification

The crude peptide in solution from 2.c was purified by semipreparative HPLC in one run on a 25 mm×250 mm column packed with 7 μm C-18 silica. The column was eluted with a gradient of 30 to 65% CH$_3$CN in 0.1% TFA/H$_2$O at 10 ml/min at a temperature of 40° C. for 47 min. The peptide containing fractions corresponding to the major peak was collected, diluted to 30 ml with approximately 3 volumes of H$_2$O and lyophilized. The final product obtained was characterized as follows:

| Analytical method | Result |
|---|---|
| HPLC A1 | r.t.: 41.12 min., |
| HPLC B6 | r.t.: 29.89 min., yield 47.9 mg. |
| LC-MS | A broad peak at 3.45 min having a mass spectrum with a very large number of mass peaks. |
| Maldi TOF MS | The mass spectrum displays a cluster of peaks with an average mass of 8875 Da. This is in agreement with the expected structure of the target compound. |

Example 3

$N^{\epsilon 37}$-(3-(mPEGyl)propionyl)[Aib$^{8,22,35}$,Lys$^{37}$]GLP-1(7-37) wherein mPEGyl is polydisperse and has a molecular weight of approximately 20 kDa

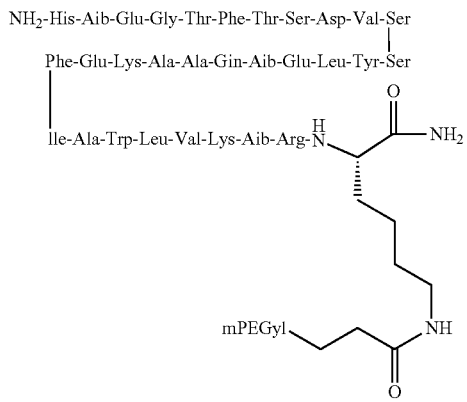

This compound was prepared from 100 mg of crude protected peptide from 2.b using procedures similar to those in example 2.c and 2.b with the major exception that 400 mg 100 mg mPEG-20000-SPA (mPEG-SPA m.w. 20.000 Lot PT-05C-11, Shearwater, Ala., USA) was used for the pegylation.

The final product obtained was characterized as follows:

| Analytical method | Result |
| --- | --- |
| HPLC A1 | r.t.: 47.62 min. |
| HPLC B6 | r.t.: 34.47 min. |
| Maldi TOF MS | The mass spectrum displays a cluster of peaks with an average mass of 25304 Da. This is in agreement with the expected structure of the target compound. |

Example 4

$N^{\epsilon 37}$-((2S)-2,6-di-(mPEGylcarbonylamino)hexanoyl)[Aib$^{8,22,35}$,Lys$^{37}$]GLP-1(7-37) wherein mPEGyl is polydisperse and has a molecular weight of approximately 20 kDa

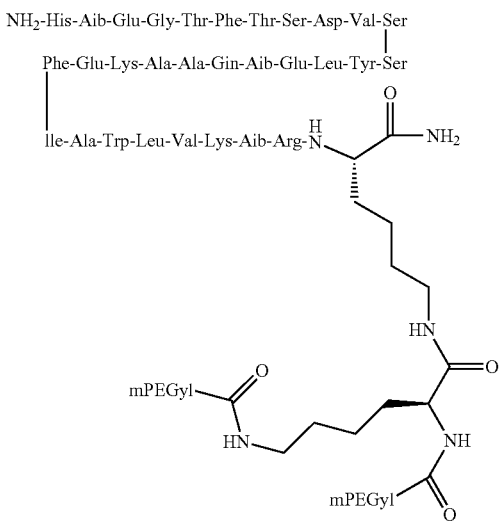

This compound was prepared from 100 mg of crude protected peptide from 2.b using procedures similar to those in example 2.c and 2.b with the major exception that 800 mg mPEG2-40000-NHS ester (mPEG2-NHS ester m.w. 40.000 Lot. PT-11C-06, Shearwater, Ala., USA) was used for the pegylation.

The final product obtained was characterized as follows:

| Analytical method | Result |
| --- | --- |
| HPLC B6 | r.t.: 30.99 min., yield 3.07 mg. conjugate |
| NMR | $^1$H-NMR showed that the 3.07 mg conjugate isolated was contaminated with approximately 7 mg hydrolysed pegylation reagent. |

Example 5

$N^{\epsilon 26}$-(3-(mPEGyl)propionyl)[Aib$^8$,Glu$^{22,30}$,Lys$^{33}$, Asn$^{34}$,Gly$^{35,36}$,Pro$^{37}$]GLP-1(7-37)ylSerSerGlyAl-aProProProSer amide wherein mPEGyl is polydisperse and has a molecular weight of approximately 2 kDa

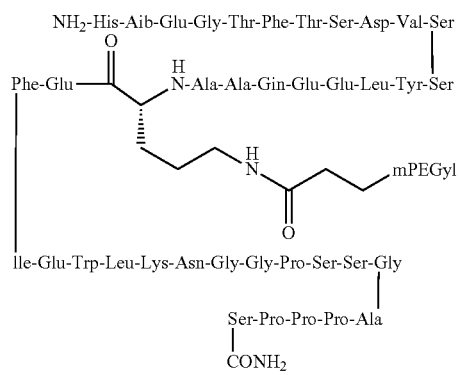

The fully protected peptidyl resin Boc-His(Boc)-Aib-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Glu(OtBu)-Gln-Ala-Ala-Lys(Dde)-Glu(OtBu)-Phe-Ile-Glu(OtBu)-Trp(Boc)-Leu- Lys(Boc)-Asn(Trt)-Gly-Gly-Pro-Ser(tBu)-Ser(tBu)-Gly-Ala-Pro-Pro-Pro-Ser(tBu)-Rink amide resin was prepared using procedures similar to those used in example 1a. from 0.25 mmol Rink amide resin having a substitution capacity of 0.61 mmol/g. The yield was 1.4 g.

Analytical results from characterization of the resin as in Example 1.b were:

| Analytical method | Result |
| --- | --- |
| HPLC A1 | r.t.: 34.99 min., |
| LC-MS | r.t. 3.29 min., Mass for (M + 3H$^+$)/3: 1432.8 Da, (calc.: 1433.2 Da) |

The Dde protection was then removed from 350 mg of this fully protected peptidyl resin using the procedures of example 1.c. and the resulting resin was then pegylated using the procedure of example 1.d using (mPEGyl)propionic acid 2,5-dioxo-pyrrolidin-1-yl ester (Shearwater cat. no. 2M4M0D01, mPEG-SPA, MW 2,000) (0.5 g, 0.25 mmol, 4 eq.) and DIEA (43 µl, 0.25 mmol, 4 eq.)

The pegylated peptide was then cleaved from the resin using procedures similar to those of example 1.e. and purified using a procedures similar to those of example 1.f The yield was 0.125 mg and the results from HPLC and LC-MS analysis:

| Analytical method | Result |
| --- | --- |
| HPLC B6 | r.t.: 37.45 min. estimated purity: 96.5% |
| LC-MS | r.t. 3.44 min., Average mass for (M + 2H$^+$)/2: 3074 Da |

Example 6

N$^\alpha$-[Aib$^{8,22,35}$]GLP-1-(7-36)yl(N$^\epsilon$-(3-(mPEGyl) propionyl)Lysinamide) wherein mPEGyl is polydisperse and has a molecular weight of approximately 750 Da

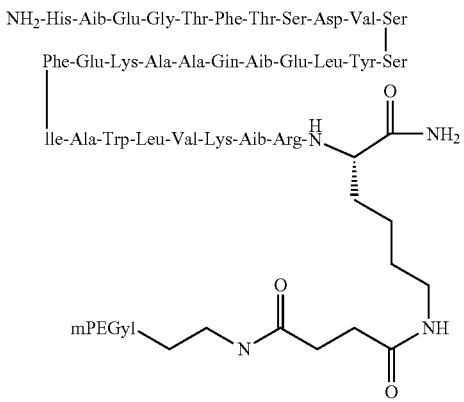

The fully protected peptidyl resin Boc-His(Boc)-Aib-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Aib-Gln(Trt)-Ala-Ala-Lys(Boc)-Glu(OtBu)-Phe-Ile-Ala-Trp(Boc)-Leu-Val-Lys(Boc)-Aib-Arg(Pmc)-Lys(ivDde)-PAL-PEG-PS resin was prepared using procedures similar to those used in example 1a. from 0.25 mmol PAL-PEG-PS resin (Applied Biosystem Cat. no. GEN 913398) having a substitution capacity of 0.38 mmol/g. The yield was 1.935 g.

The ivDde protection was removed from the protected peptidyl resin as follows. The resin (382 mg, 90 μmol) was washed in NMP. A freshly prepared solution of hydrazine hydrate 2% in NMP (20 ml) was added and the reaction mixture was shaken for 12 min at room temperature, and then filtered. The hydrazine treatment was repeated twice. After this the resin was washed extensively with NMP and coupled with (N-(2-mPEGyl-ethyl)-4-(2,5-dioxo-pyrrolidin-1-yl)-4-oxo-butyramide (α-Methoxy-ω-NHS ester PEG, Rapp Polymere GmbH, Tübingen, FRG, cat no. 12 750-35) (0.27 g, 0.36 mmol, 4 eq.) using the procedures of example 1.d.

The pegylated peptide was then cleaved and characterized from the resin using procedures similar to those of example 1.e.

Results from HPLC and LC-MS analysis of the dry precipitate:

| Analytical method | Result |
| --- | --- |
| HPLC A1 | r.t.: 37.90 min., |
| LC-MS | r.t. 3.46 min., Average mass for (M + 3H$^+$)/3: 1410 Da |

The crude peptide was finally purified using the procedures similar to those of example 1.f. The yield was 26 mg product which was characterized by HPLC and LC-MS

| Analytical method | Result |
| --- | --- |
| HPLC A1 | r.t.: 37.90 min., |
| HPLC B1 | r.t.: 39.46 min. estimated purity: 98% |
| LC-MS | r.t. 3.48 min., Average mass for (M + 3H$^+$)/3: 1410 Da |

Example 7

N$^\alpha$-[Aib$^{8,22,35}$]GLP-1(7-37)yl(S$^\epsilon$-(1-mPEGylpropyl-2,5-dioxo-pyrrolidin-3-yl)Cysteinamide wherein mPEGyl is polydisperse and has a molecular weight of approximately 5000 Da

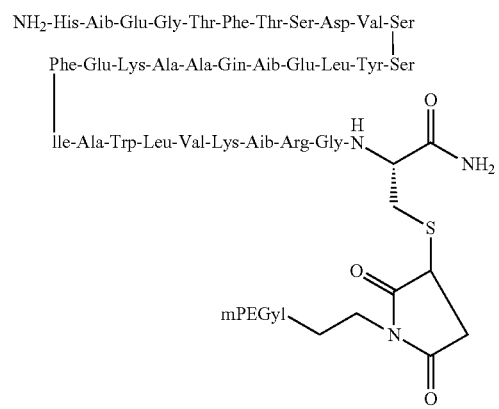

The crude peptide His-Aib-Glu-Gly-Thr-Phe-Thr-Ser-Asp-Val-Ser-Ser-Tyr-Leu-Glu-Aib-Gln-Ala-Ala-Lys-Glu-Phe-Ile-Ala-Trp-Leu-Val-Lys-Aib-Arg-Gly-Cys(H) amide was prepared using procedures similar to those used in example 1a., and 1.e from 0.25 mmol Rink amide resin having a substitution capacity of 0.61 mmol/g. The yield was 121 mg Results from HPLC and LC-MS analysis of the dry precipitate of crude peptide:

| Analytical method | Result |
| --- | --- |
| HPLC A1 | r.t.: 36.15 min., |
| LC-MS | r.t. 3.51 min., Mass for (M + 3H$^+$)/3: 1177.1.3 Da, (calc.: 1176 Da) |

A fraction of the crude peptide (10 mg, 3 μmol) was dissolved in phosphate buffer (15 ml) and pH was adjusted to 6.5 and mPEG-Mal 5000 (Shearwater cat. no. 2D2M0H01, mPEG-MAL, MW 5,000) (28 mg, 6 μmol) was added and the mixture was stirred for 30 min. The final product was isolated from this mixture using procedures similar to those of example 1.f.

The yield was 2.2 mg and the results from HPLC and LC-MS analysis:

| Analytical method | Result |
|---|---|
| HPLC A1 | r.t.: 37.41 min., |
| LC-MS | r.t. 3.56 min., Average mass for (M + 6H$^+$)/6: 1058.1 Da, |

Example 8

N$^\alpha$-(3-(3H-imidazol-4-yl)-propionyl [Aib$^{22,35}$, Arg$^{26,34}$]GLP-1-(8-37))yl(N$^\epsilon$-(3-(mPEGyl)propionyl)Lysinamide) wherein mPEGyl is polydisperse and has a molecular weight of approximately 2000 Da

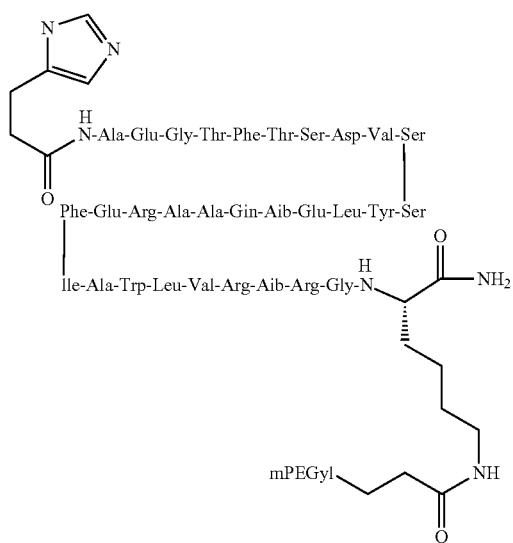

The fully protected peptidyl resin ImPr(Adoc)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Aib-Gln-Ala-Ala-Arg(Pmc)-Glu(OtBu)-Phe-Ile-Ala-Trp(Boc)-Leu-Val-Arg(Pmc)- Aib-Arg(Pmc)-Gly-Lys(Boc)-Rink amide resin using procedures similar to those used in example 1a in 1 mmol scale, with the exception that HATU was used as the coupling agent throughout the synthesis. The resin used was a hydrophilic Rink amide resin (HypoGel® 200 RAM) (Rapp Polymere cat. # SP200 110150 230) resin having a substitution capacity of 0.61 mmol/g.

Cleavage and purification was carried out as in the examples 1e and 1f. The yield was 210 mg and the results from HPLC and LC-MS analysis:

Analytical method. Result: HPLC A1 r.t.: 36.51 min., LC-MS r.t. 3.69 min., mass for (M+3H$^+$) 13: 1194.4 Da, (calc.: 1193.4 Da)

The pegylation was performed as follows. 20 mg of the unprotected peptide was dissolved in 600 μl water and 100 mg of the pegylation reagent (mPEGyl)propionic acid 2,5-dioxo-pyrrolidin-1-yl ester) (Shearwater cat. no. 2M4M0D01, mPEG-SPA, MW 2,000) was added together with 9 μl DIEA and stirred for 24 h. The final product was isolated from this mixture using procedures similar to those of example 1.f. The yield was 3.7 mg of the title compound and results from HPLC and MALDI analysis were:

Analytical method. Result: HPLC 01_B4_2 r.t.: 10.96 min., MALDI-TOF Average mass for (M$^+$): 5724 Da Example 9

Preparation of N$^{\epsilon 26}$-(3-(mPEGyl)propionyl)[Arg$^{34}$]GLP-1-(7-37) wherein mPEGyl is polydisperse and has a molecular weight of approximately 2 kDa

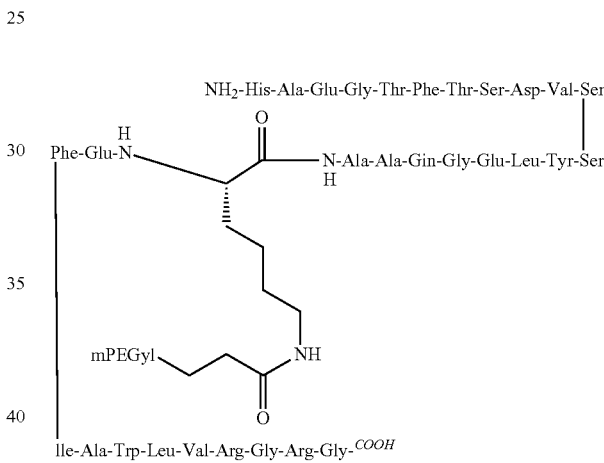

This compound was prepared by acylation in solution of unprotected [Arg$^{34}$]GLP-1-(7-37) which was obtained by expression in yeast. [Arg34]GLP-1-(7-37) peptide (0.3 g, 30% peptide content) was dissolved in water containing DIEA (101 μl, 20 e.q.) and acylated with mPEG SPA 2000 (Shearwater Cat. no. 2M4M0D01, mPEG-SPA, MW 2,000) (89 mg, 1.5 e.q.) for 1 h at room temperature. The final product was isolated from this mixture using procedures similar to those of example 1.f. The yield of the title compound was 61 mg and the results from HPLC and Maldi TOF MS analysis were:

| Analytical method | Result |
|---|---|
| HPLC 02_B4_2 | r.t.: 8.48 min., |
| MALDI-TOF | Average mass for (M$^+$): 5587.3 Da |

Example 10

(S)—N—((S)-5-(N—((S)-5-carbamoyl-5-(mPEGyl-propionylamino)pentyl)carbamoyl)-5-(mPEGylpropionylamino)pentyl)-5-(N$^{\alpha 7}$-(3-(4-imidazolyl)propionyl)[Aib$^{22,35}$,Arg$^{26,34}$]GLP-1-(8-37)yl)-2-(mPEGylpropionylamino)hexanoic amide wherein mPEGyl is polydisperse and has a molecular weight of approximately 750 Da The fully protected peptidyl resin Boc-Lys(Boc-Lys(Boc-Lys(ImPr(Adoc)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Aib-Gln(Trt)-Ala-Ala-Arg(Pmc)-Glu(OtBu)-Phe-Ile-Ala- Trp(Boc)-Leu-Val-Arg(Pmc)-Aib-Arg(Pmc))))-Rink amide resin was synthesized using the procedures in example 1.a. ImPr(Adoc)-OH was used for the introduction of the N-terminal 3-(4-Imidazolyl)propionyl group and Boc-Lys(Fmoc)-OH was used for introducing three side chain linked Lys residues in the C-terminal of the sequence.

The corresponding unprotected peptide, H-Lys(H-Lys(H-Lys(ImPr-Ala-Glu-Gly-Thr-Phe-Thr-Ser-Asp-Val-Ser-Ser-Tyr-Leu-Glu-Aib-Gln-Ala-Ala-Arg-Glu-Phe-Ile-Ala-Trp-Leu-Val-Arg-Aib-Arg))) amide, was cleaved from the resin using procedures similar to those of example 1.e. and purified using procedures similar to those in example 1.f.

The results from the characterization of this intermediate peptide were:

| Analytical method | Result |
| --- | --- |
| HPLC A1 | r.t.: 35.39 min., |
| HPLC B1 | r.t.: 36.50 min. |
| LC-MS | r.t. 3.85 min., Mass for (M + 3H+)/3: 1279.8 Da, (calc.: 1279.8 Da) |

3.84 mg this purified peptide dissolved it in 0.4 ml NMP and pegylated by stirring at room temperature for 4 h with 8 mg with (N-(2-mPEGyl-ethyl)-4-(2,5-dioxo-pyrrolidin-1-yl)-4-oxo-butyramide (α-Methoxy-ω-NHS ester PEG, Rapp Polymere GmbH, Tübingen, FRG, cat no. 12 750-35) and 7 μl DIEA.

The title compound was finally purified using procedures similar to those in example 1.f.

The results from the characterization were:

| Analytical method | Result |
| --- | --- |
| HPLC A1 | r.t.: 41.62 min., |
| HPLC B1 | r.t.: 43.02 min., yield 6.5 mg. |
| LC-MS | A broad peak at 4.24 min having a mass spectrum with a very large number of mass peaks. |
| Maldi TOF MS | The mass spectrum displays a cluster of peaks with an average mass of 6000 Da. This is in agreement with the expected structure of the target compound. |

Example 11

Method for Measuring Pulmonary Bioavailability

The present protocol describes the methods and materials used in the development of an anaesthetized rat model for pulmonal delivery of aerosols. The aerosols are generated by use of a nebulizer catheter with a well defined droplet/particle size (mean mass aerodynamic diameter, MMAD). The nebulizer catheter is an extruded multi-lumen catheter that provides fine-particle, baffle-free, aerosols. It incorporates multiple (typically 4-6) gas-lumens around one liquid lumen. Each lumen extends the length of the catheter which tapers to a fine (~0.5 mm diameter) nozzle with tiny orifices at the distal tip. The intimate contact between the gas and liquid at the tip produces a fine aerosol without baffling. The nebulizer catheter is guided through an endotracheal tube and is placed just above the main bronchial branch. The aerosol is deposited in pulses managed from a control unit.

Equipment

The equipment for pulmonary delivery is obtained from Trudell Medical International (London, Ontario, Canada).

Nebulizer Catheters

Nebulizer catheters (Aeroprobe®) are supplied from the manufacturer in a number of different configurations and lengths. These different designs will accommodate a variety of different fluid and flow-rates, as well as provide aerosol particle-sizes that may be as low as 5 µm MMAD (mean mass aerodynamic diameter). In the present experiments a catheter with the following dimensions is used: Outer lumens gas flow of 1.4 L/min, inner lumen liquid flow of 0.7 ml/min, and MMAD of about 7-8 μm (PN 104504-050) with a length of 50 cm (1).

Control Unit

LABNeb® Catheter control system (CCS). The Aeroprobe catheter is connected to the control system according to (2).

Air with a pressure of 100 psi is used as supporting gas and maximal fluid pressure, usually 98 psi. A 100 μl syringe is used as reservoir. The LABNeb CCS used a pulse time of 80 msec and a gas delay of 20 msec. Thus, 2.3 ml air and 0.93 μl test solution are delivered in each pulse.

Animals

Sprague Dawley ♂ rats weighing between 250 and 350 g. The animals are housed under standardised conditions with free access to food (Altromine 1324) and drinking water. On the experimental day the animals are used in their fed state.

Solution for Anaesthesia

Hypnorm® (fentanyl 0.2 mg/ml, fluansol 10 mg/ml) is diluted with sterile water 1+1. Dormicum® (midazolam 5 mg/ml) is diluted with sterile water 1+1. The two solutions are mixed 1+1.

Surgical Procedures and Intratracheal Administration

Anaesthesia is induced by injecting subcutaneously the prepared Hyponorm/Dormicum solution 0.25 ml/100 g BW. An endotracheal tube (PE 240, Becton Dickinson) is inserted and guided to a position about ½ cm above the branch of the two main bronchii. Any heat loss is minimised by wrapping a plastic shield round the rat.

Before applying the test solution into the lungs, it is secured that the syringe and catheter system is free of air bubbles. Before applying the test solution endotracheally, it is sprayed into a vial to test subsequently the amount of substance administered by the catheter. Then, the catheter is guide through the endotracheal tube leaving 1-2 mm of the catheter tip free of the tube end and the test solution is aerosolised into the lungs of the anaesthetised rat.

The invention claimed is:

1. A compound having a structure of formula (I)

Insulinotropic agent(-Y—C*)$_f$-Q    (I)

wherein

Insulinotropic agent is a radical comprising an insulinotropic peptide wherein said peptide comprises the amino acid sequence of formula (III):

Xaa7-Xaa8-Glu-Gly-Thr-Phe-Thr-Ser-Asp-Val-Ser-Xaa18-Tyr-Leu-Glu-Xaa22-Xaa23-Ala-Ala-Xaa26-Glu-Phe-Ile-Xaa30-Trp-Leu-Val-Xaa34-Xaa35-Xaa36-Xaa37-Xaa38    Formula (III)(SEQ ID NO: 4)

wherein
Xaa7 is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
Xaa8 is Ala, D-Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa18 is Ser, Lys or Arg;
Xaa22 is Gly, Glu or Aib;
Xaa23 is Gln, Glu, Lys or Arg;
Xaa26 is Lys, Glu or Arg;
Xaa30 is Ala, Glu or Arg;
Xaa34 is Lys, Glu or Arg;
Xaa35 is Gly or Aib;
Xaa36 is Arg or Lys;
Xaa37 is Gly, Ala, Glu or Lys;
Xaa38 is Lys, NH2 or is absent,
wherein said insulinotropic agent contains one or more Aib residues and
wherein
Y is a bivalent connecting chemical group connecting C* with the Insulinotropic agent, and
C* is a bivalent polar separating chemical group where 20-50% of the heavy atoms are either O or N, and
f is 0 or 1 and
Q is selected from

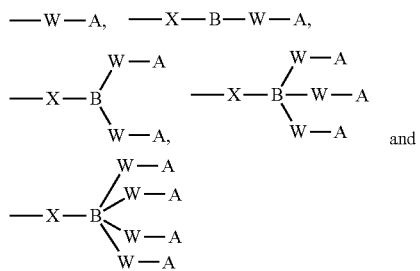

wherein
A is mPEGyl or A is mPEGyl-C(=O)—(CH2)r—, wherein r is an integer in the range from 1-10, and
W is a bivalent chemical group whereby A is connected, and
X is a bivalent connecting chemical group whereby B is connected, and
B is a connecting or branching chemical group.

2. The compound according to claim 1, wherein A is monodisperse.

3. The compound according to claim 1, wherein A is polydisperse.

4. The compound according to claim 1, wherein the branching chemical group B is selected from

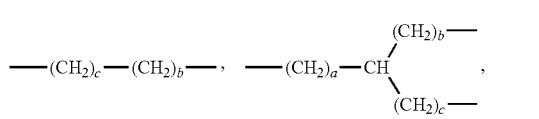

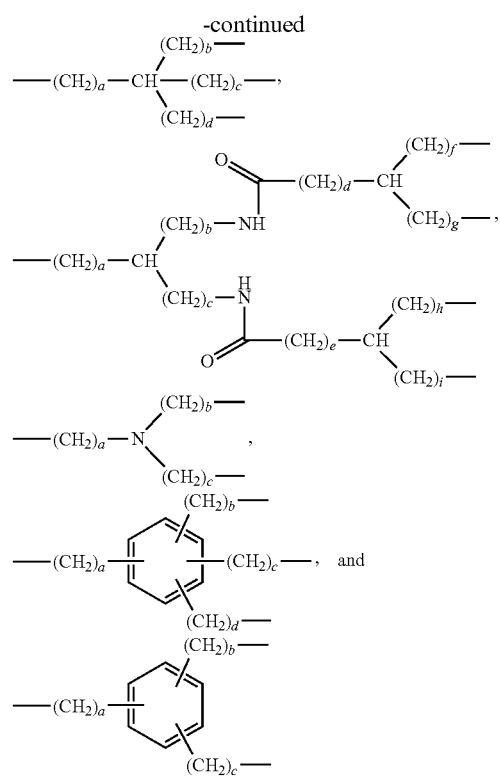

wherein a, b, c, d, e, f, g, h, i are integers independently selected from the range from 0 to 24.

5. The compound according to claim 1, wherein the branching group B is

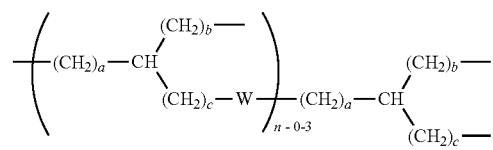

wherein a, b, c are integers independently selected from the range from 0 to 24.

6. The compound according to claim 4, wherein the branching chemical group B is selected from

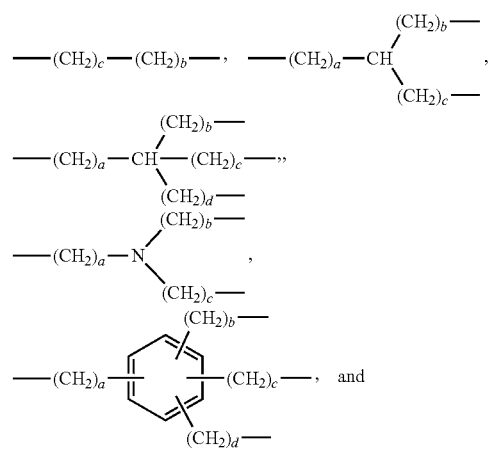

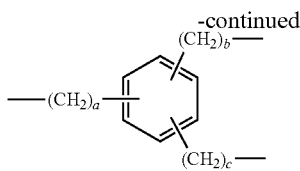

wherein a, b, c, d, e, f, g, h, i are integers independently selected from the range from 0 to 24.

7. The compound according to claim 4, wherein a+b is less than 6 or a+b+c is less than 14 or a+b+c+d+e+f+g+h+l is less than 16.

8. The compound according to claim 4, wherein a is 0 or 1 and b, c, d, e, f, h and i are all in the range from 0 to 5.

9. The compound according to claim 4, wherein a, c, d, e, g and i are all 0 and b, f and h are all in the range from 1 to 4.

10. The compound according to claim 1, wherein a, c, d, e, g and l are all 0 and b, f and h are all in the range from 1 to 4.

11. The compound according to any claim 1, wherein W and X are independently selected from the bivalent connecting chemical groups comprising amides: —C(O)—NR—, where R is hydrogen or $C_{1-6}$-alkyl,
amine: —NR—, where R is hydrogen or $C_{1-6}$-alkyl,
thioethers: —S—, —S—$(CH_2)_2$—$SO_2$— or

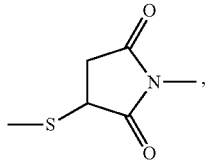

ethers: —O—,
urethanes: —N($R^1$)—CO—N($R^2$)—, where $R^1$ and $R^2$ independently is hydrogen or $C_{1-6}$-alkyl,
carbamates: —O—CO—N(R)—, where R is hydrogen or $C_{1-6}$-alkyl,
hydrazines:

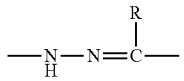

where R is hydrogen or $C_{1-6}$-alkyl,
oximes: —O—N=C(—R)—, where R is hydrogen or $C_{1-6}$-alkyl,
oxazolidines or thiazolidines:

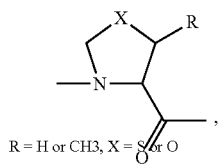

and

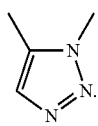

12. The compound according to claim 1, wherein W is: —C(O)—NR—, where R is hydrogen or $C_{1-6}$-alkyl.

13. The compound according to claim 12, wherein the insulinotropic agent is attached to W via the left hand terminal (the carbon) of W.

14. The compound according to claim 12, wherein the insulinotropic agent is attached to W via the right hand terminal (the nitrogen) of W.

15. The compound according to claim 1, wherein f is 0.

16. The compound according to claim 1, wherein C* is —$(CH_2)_{n1}O[(CH_2)_{n2}O]_{n3}(CH_2)_{n4}$—, where n1, n2 and n4 independently is an integer in the range from 1 to 10, n3 is an integer in the range from 1 to 5000, and where n3 multiplied by n2+1 is less than 10000.

17. The compound according to claim 16, wherein n2 is 2 or 3.

18. The compound according to claim 16, wherein n3 is in the range from 1-20.

19. The compound according to claim 1, wherein C* is —$(CH_2)_{n5}$—, where n5 is an integer in the range from 1 to 10.

20. The compound according to claim 1, wherein Y is selected from the bi-valent connecting chemical groups comprising amides: —C(O)—NR—, where R is hydrogen or $C_{1-6}$-alkyl,
amine: —NR—, where R is hydrogen or $C_{1-6}$-alkyl,
thioethers: —S—, —S—$(CH_2)_2$—$SO_2$— or

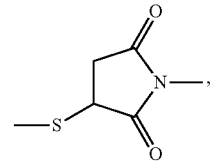

ethers: —O—,
urethanes: —N($R^1$)—CO—N($R^2$)—, where $R^1$ and $R^2$ independently is hydrogen or $C_{1-6}$-alkyl,
carbamates: —O—CO—N(R)—, where R is hydrogen or $C_{1-6}$-alkyl,
hydrazines:

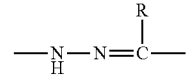

where R is hydrogen or $C_{1-6}$-alkyl,
oximes: —O—N=C(—R)—, where R is hydrogen or $C_{1-6}$-alkyl,
oxazolidines or thiazolidines:

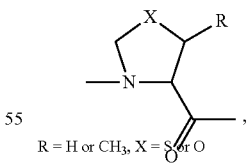

and

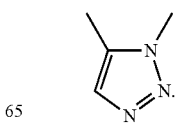

21. The compound according to claim 1, wherein said insulinotropic agent comprises no more than 4 amino acid residues which are not encoded by the genetic code.

22. The compound according to claim 1, wherein said insulinotropic agent comprises an Aib residue as the second amino acid residue from the N-terminal.

23. The compound according to claim 1, wherein $Xaa_7$ in SEQ ID NO: 4 of said insulinotropic agent is selected from the group consisting of D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine and 4-pyridylalanine.

24. The compound according to claim 1, wherein said insulinotropic agent is selected from the group consisting of [$Aib^{8,22,35}$]GLP-1(7-37), [$Aib^{8,35}$]GLP-1(7-37), [$Aib^{8,22}$]GLP-1(7-37), [$Aib^{8,22,35}Arg^{26,34}$]GLP-1(7-37)Lys, [$Aib^{8,35}Arg^{26,34}$]GLP-1(7-37)Lys, [$Aib^{8,22}Arg^{26,34}$]GLP-1(7-37)Lys, [$Aib^{8,22,35}Arg^{26,34}$]GLP-1(7-37)Lys, [$Aib^{8,35}Arg^{26,34}$]GLP-1(7-37)Lys, [$Aib^{8,22,35}Arg^{26}$]GLP-1(7-37)Lys, [$Aib^{8,35}$ $Arg^{26}$]GLP-1(7-37)Lys, [$Aib^{8,22}Arg^{26}$]GLP-1(7-37)Lys, [$Aib^{8,22,35}Arg^{34}$]GLP-1(7-37)Lys, [$Aib^{8,35}Arg^{34}$]GLP-1(7-37)Lys, [$Aib^{8,22}Arg^{34}$]GLP-1(7-37)Lys, [$Aib^{8,22,35}Ala^{37}$]GLP-1(7-37)Lys, [$Aib^{8,35}Ala^{37}$]GLP-1(7-37)Lys, [$Aib^{8,22}Ala^{37}$]GLP-1(7-37)Lys, [$Aib^{8,22,35}Lys^{37}$]GLP-1(7-37), [$Aib^{8,35}Lys^{37}$]GLP-1(7-37), [$Aib^{8,22}Lys^{37}$]GLP-1(7-37) or derivatives thereof which has been amidated on the C-terminal.

25. The compound according to claim 1, wherein said insulinotropic agent contains two Aib residues.

26. The compound according to claim 1, wherein said insulinotropic agent comprises a serine residue at $Xaa_{18}$ of SEQ ID NO: 4.

27. The compound according to claim 1, wherein said insulinotropic agent comprises a glycine residue at $Xaa_{22}$ of SEQ ID NO: 4.

28. The compound according to claim 1, wherein said insulinotropic agent comprises a glutamine residue at $Xaa_{23}$ of SEQ ID NO: 4.

29. The compound according to claim 1, wherein said insulinotropic agent comprises a lysine residue at $Xaa_{26}$ of SEQ ID NO: 4.

30. The compound according to claim 1, wherein said insulinotropic agent is attached to Y—C*-Q or Q via an amino acid residue selected from one of the 10 C-terminal amino acid residues.

31. The compound according to claim 1, wherein said insulinotropic agent is attached to Y—C*-Q or Q via $Xaa_{23}$, $Xaa_{26}$, $Xaa_{34}$, $Xaa_{36}$ or $Xaa_{38}$ of SEQ ID NO: 4.

32. The compound according to claim 1, wherein said insulinotropic agent is attached to Y—C*-Q or Q via the C-terminal amino acid residue.

33. The compound according to claim 1, wherein said insulinotropic agent is attached to Y—C*-Q or Q via a carboxyl group, an amino group, a keto group, a hydroxyl group, a thiol group or a hydrazide group.

34. The compound according to claim 1, wherein said insulinotropic agent is attached to Y—C*-Q or Q via the epsilon-amino group on a lysine residue.

35. The compound according to claim 34, wherein said insulinotropic agent comprises only one lysine residue.

36. The compound according to claim 35, wherein said lysine residue is the C-terminal amino acid residue of said insulinotropic agent.

37. A compound selected from the group consisting of
$N^{\epsilon 37}$-((2S)-2,6-di-(mPEGylcarbonylamino)hexanoyl) [$Aib^{8,22,35}$,$Lys^{37}$]GLP-1(7-37) wherein mPEGyl is polydisperse and has a molecular weight of approximately 20 kDa, $N^{\epsilon 37}$-(3-(mPEGyl)propionyl)[$Aib^{8,22,35}$,$Lys^{37}$]GLP-1(7-37) wherein mPEGyl is polydisperse and has a molecular weight of approximately 20 kDa, $N^{\epsilon 37}$-(3-(mPEGyl)propionyl)[$Aib^{8,22,35}$,$Lys^{37}$]GLP-1(7-37) wherein mPEGyl is polydisperse and has a molecular weight of approximately 5 kDa, $N^{\epsilon 37}$-(3-(mPEGyl)propionyl)[$Aib^{8,22,35}$,$Lys^{37}$]GLP-1(7-37) amide wherein mPEGyl is polydisperse and has a molecular weight of approximately 2 kDa, $N^{\epsilon 26}$-(3-(mPEGyl)propionyl)[$Aib^8$,$Glu^{22,30}$,$Lys^{33}$,$Asn^{34}$, $Gly^{35,36}$,$Pro^{37}$] GLP-1(7-37)ylSerSerGlyAlaProPro-ProSer amide wherein mPEGyl is polydisperse and has a molecular weight of approximately 2 kDa, $N^\alpha$-[$Aib^{8,22,35}$]GLP-1-(7-37)yl($N^\epsilon$-(3-(mPEGyl)propionyl)Lysinamide) wherein mPEGyl is polydisperse and has a molecular weight of approximately 750 Da, $N^\epsilon$-[$Aib^{8,22,35}$]GLP-1(7-37)yl($S^\epsilon$-(1-mPEGylpropyl-2,5-dioxo-pyrrolidin-3-yl)Cysteinamide wherein mPEGyl is polydisperse and has a molecular weight of approximately 5000 Da, $N^\alpha$-(3-(3 H-imidazol-4-yl)-propionyl [$Aib^{22,35}$, $Arg^{26,34}$] GLP-1-(8-37))yl($N^\epsilon$-(3-(mPEGyl)propionyl)Lysinamide) wherein mPEGyl is polydisperse and has a molecular weight of approximately 2000 Da,
and
(S)—N—((S)-5-(N—((S)-5-carbamoyl-5-(mPEGylpropionylamino)pentyl)carbamoyl)-5-(mPEGylpropionylamino)pentyl)-5-($N^{\alpha 7}$-(3-(4-imidazolyl)propionyl) [$Aib^{22,35}$,$Arg^{26,34}$]GLP-1-(8-37)yl)-2-(mPEGylpropionylamino)hexanoic amide wherein mPEGyl is polydisperse and has a molecular weight of approximately 750 Da.

38. A pharmaceutical composition comprising a compound according to claim 1 and a pharmaceutically acceptable excipient.

39. The pharmaceutical composition according to claim 38, which is suited for pulmonary administration.

40. A method for treating hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers, said method comprising administering to a subject in need of such treatment an effective amount of a pharmaceutical composition according to claim 38.

41. A method for delaying disease progression in type 2 diabetes in a subject, said method comprising administering to said subject an effective amount of a pharmaceutical composition according to claim 38.

42. A method for decreasing food intake, decreasing β-cell apoptosis, increasing β-cell function and β-cell mass, and/or for restoring glucose sensitivity to β-cells in a subject, said method comprising administering to said subject an effective amount of a pharmaceutical composition according to claim 38.

43. A compound having a structure of formula (I)

$$\text{Insulinotropic agent(-Y—C*)}_f\text{-Q} \tag{I}$$

wherein
Insulinotropic agent is a radical comprising an insulinotropic peptide selected from the group consisting of

[Arg³⁴]GLP-1(7-37), [Arg²⁶,³⁴]GLP-1(7-37)Lys, [Lys³⁶Arg²⁶,³⁴]GLP-1(7-36)

wherein
Y is a bivalent connecting chemical group connecting C* with the Insulinotropic agent, and
C* is a bivalent polar separating chemical group where 20-50% of the heavy atoms are either O or N, and
f is 0 or 1 and
Q is selected from

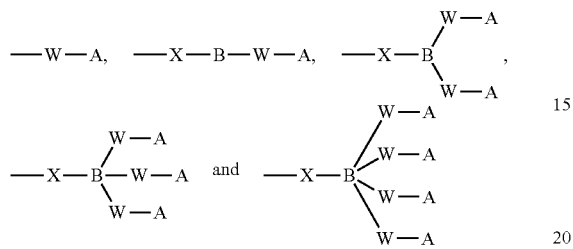

wherein
A is mPEGyl or A is mPEGyl-C(=O)—(CH$_2$)$_r$—, wherein r is an integer in the range from 1-10, and
W is a bivalent chemical group whereby A is connected, and
X is a bivalent connecting chemical group whereby B is connected, and B is a connecting or branching chemical group.

* * * * *